(12) United States Patent
Lobie et al.

(10) Patent No.: US 11,141,402 B2
(45) Date of Patent: Oct. 12, 2021

(54) COMPOUNDS USEFUL IN INHIBITING HUMAN TREFOIL FACTOR 3

(71) Applicants: NATIONAL UNIVERSITY OF SINGAPORE, Singapore (SG); UNIVERSITY OF MYSORE, Mysore (IN); BANGALORE UNIVERSITY, Bengaluru (IN)

(72) Inventors: Peter Edward Lobie, Singapore (SG); Vijay Kumar Pandey, Singapore (SG); Rangappa Kanchugarakoppal Subbegowda, Mysore (IN); Basappa, Bangalore (IN); Mohan Chakrabhavi Dhananjaya, Mysore (IN); Shobith Rangappa, Mysore (IN)

(73) Assignees: National University of Singapore, Singapore (SG); University of Mysore, Mysore (IN); Bangalore University, Bengaluru (IN)

( * ) Notice: Subject to any disclaimer, the term of this patent is extended or adjusted under 35 U.S.C. 154(b) by 0 days.

(21) Appl. No.: 16/619,218

(22) PCT Filed: Jun. 5, 2018

(86) PCT No.: PCT/SG2018/050277
§ 371 (c)(1),
(2) Date: Dec. 4, 2019

(87) PCT Pub. No.: WO2018/226155
PCT Pub. Date: Dec. 13, 2018

(65) Prior Publication Data
US 2020/0147039 A1 May 14, 2020

(30) Foreign Application Priority Data

Jun. 5, 2017 (SG) .......................... 10201704579V

(51) Int. Cl.
*A61K 31/37* (2006.01)
*A61K 31/4433* (2006.01)
*A61K 45/06* (2006.01)
*C07D 493/04* (2006.01)

(52) U.S. Cl.
CPC .......... *A61K 31/37* (2013.01); *A61K 31/4433* (2013.01); *A61K 45/06* (2013.01); *C07D 493/04* (2013.01)

(58) Field of Classification Search
CPC .... A61K 31/37; A61K 31/4433; A61K 45/06; C07D 493/04
See application file for complete search history.

(56) References Cited

FOREIGN PATENT DOCUMENTS

| CN | 102757446 A | 10/2012 |
|---|---|---|
| CN | 105801595 A | 7/2016 |
| WO | 2007119600 A1 | 10/2007 |
| WO | WO2016022465 A1 | 2/2016 |

OTHER PUBLICATIONS

Keerthy et al., 5(109) RSC Advances 89797-89808 (2015) (CAS Abstract) (Year: 2015).*
CAS RN 1015615-51-6, STN entry date Apr. 18, 2008.
CAS RN 1015615-19-6, STN entry date Apr. 18, 2008.
CAS RN 1015566-77-4, STN entry date Apr. 18, 2008.
CAS RN 1015566-43-4, STN entry date Apr. 18, 2008.
CAS RN 1015559-40-6, STN entry date Apr. 18, 2008.
CAS RN 1015615-35-6, STN entry date Apr. 18, 2008.
CAS RN 1015615-11-8, STN entry date Apr. 18, 2008.
CAS RN 1015584-17-4, STN entry date Apr. 18, 2008.
CAS RN 1015566-71-8, STN entry date Apr. 18, 2008.
CAS RN 1015566-64-9, STN entry date Apr. 18, 2008.
CAS RN 1015566-57-0, STN entry date Apr. 18, 2008.
CAS RN 1015566-50-3, STN entry date Apr. 18, 2008.
CAS RN 1015559-34-8, STN entry date Apr. 18, 2008.
CAS RN 1015559-28-0, STN entry date Apr. 18, 2008.
CAS RN 1015559-22-4, STN entry date Apr. 18, 2008.
Dehkordi, Mahvash Farajzadeh et al., "Multispectral studies of DNA binding, antioxidant and cytotoxic activities of a new pyranochromene derivative," Spectrochimica Acta Part A: Molecular and Biomolecular Spectroscopy (2015) 145, 353-359.
Kanakaraju, Sankari et al., "Design, Synthesis, and in Vitro Antimicrobial Evaluation of Fused Pyrano[3,2-e] tetrazolo[1,5-c]pyrimidines and Diazepines," ISRN Organic Chemistry (2013) 2013, 1-9.
Kannan, Nagarajan et al., "Trefoil Factor 3 is Oncogenic and Mediates Anti-Estrogen Resistance in Human Mammary Carcinoma," Neoplasia (Dec. 2010) 12(12), 1041-1062.
Keerthy, Hosadurga K. et al., "Molprint 2D-based identification and synthesis of novel chromene based small molecules that target PLA2: validation through chemo- and bioinformatics approaches," RSC Advances (2015) 5, 89797-89808.

(Continued)

*Primary Examiner* — Timothy R Rozof
(74) *Attorney, Agent, or Firm* — Eric D. Babych; Barnes & Thornburg LLP

(57) ABSTRACT

Disclosed herein are compounds of Formula I,

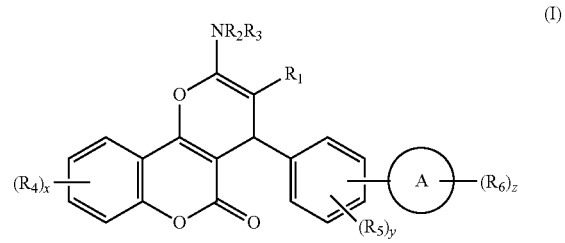

wherein A, $R_1$ to $R_6$, and x to z have the meanings given in the description.

19 Claims, 9 Drawing Sheets

(56) References Cited

OTHER PUBLICATIONS

Figures 1A, 1B:
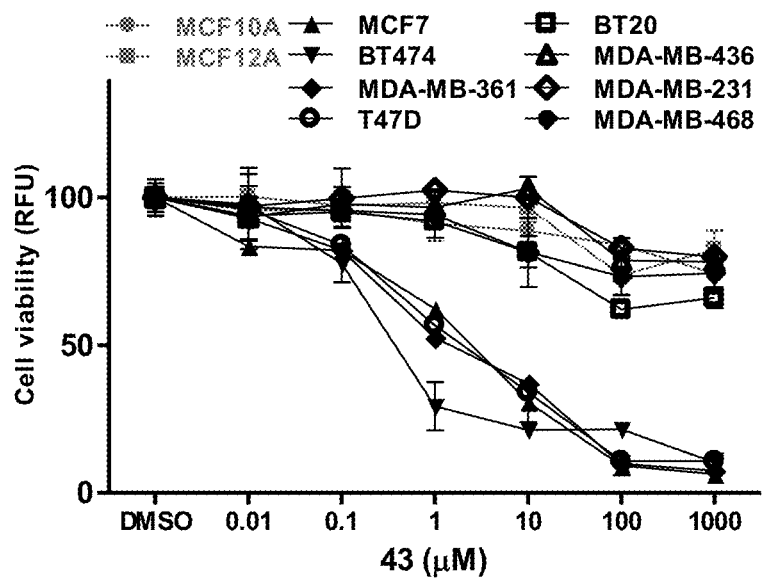

Keerthy, Hosadurga K. et al., "Synthesis and Characterization of Novel 2-Amino-Chromene-Nitriles that Target Bcl-2 in Acute Myeloid Leukemia Cell Lines," PLOS One (Sep. 2014) 9(9), e107118. 1-11.
Kovacikova, Lucia et al., "Synthesis of 3-phenyl-2H,5H-pyrano[3,2-c]chromen-2-one derivatives and their antineoplastic activity," ARKIVOC (Online Journal of Organic Chemistry) (2010) xi, 188-203.
Langer, Robert, "New Methods of Drug Delivery," Science (Sep. 28, 1990) 249(4976), 1527-1533.
Li, Jing et al., "Synthesis of biscoumarin and dihydropyran derivatives with promising antitumor and antibacterial activities," Bioorganic & Medicinal Chemistry Letters (2015) 25, 5520-5523.
Maleki, Behrooz, "Green Synthesis of bis-Coumarin and Dihydropyrano[3,2-c]chromene Derivatives Catalyzed by o-Benzenedisulfonimide," Organic Preparations and Procedures International (2016) 48(3), 303-318.
Montagut-Romans, Adrien et al., "3-Methylene-2,4-chromandione in situ trapping: introducing molecular diversity on 4-hydroxycoumarin," RSC Advances (2016) 6, 4540-4544.
Pandey, Vijay et al., "Artemin Stimulates Oncogenicity and Invasiveness of Human Endometrial Carcinoma Cells," Endocrinology (Mar. 2010) 151(3), 909-920.
Pandey, Vijay et al., "Autocrine Human Growth Hormone Stimulates Oncogenicity of Endometrial Carcinoma Cells," Endocrinology (Aug. 2008) 149(8), 3909-3919.
Pandey, Vijay et al., "Trefoil factor 3 promotes metastatic seeding and predicts poor survival outcome of patients with mammary carcinoma," Breast Cancer Research (2014) 16, 429, 1-20.
Perera, Omesha et al., "Trefoil factor 3 (TFF3) enhances the oncogenic characteristics of prostate carcinoma cells and reduces sensitivity to ionising radiation," Cancer Letters (2015) 361, 104-111.
Sui, Yun-Peng et al., "Antibacterial and Antitumor Activities of Biscoumarin and Dihydropyran Derivatives," Molecules (2015) 20, 17614-17626.
Wanqiu, Zhang, "The Role of TFF3 in Cytotoxic Drug Resistance of Breast Cancer," Department of Pharmacology, National University of Singapore, Thesis (2013) 1-128.
Zhang, Zhanyi et al., "A novel and efficient one-pot four-component tandem approach for the synthesis of pyran derivatives," Molecular Diversity (2012) 16, 423-430.
Zhou, Hai-Yu et al., "Antitumor activities of biscoumarin and dihydropyran derivatives," Bioorganic & Medicinal Chemistry Letters (2016) 26, 3876-3880.
PCT International Search Report for PCT/SG2018/050277, dated Sep. 20, 2018, 5 pages.
PCT Written Opinion of the International Searching Authority for PCT/SG2018/050277, dated Sep. 20, 2018, 7 pages.
Extended European Search Report for EP App 18813214.6, dated Oct. 28, 2020, 9 pages.
Ahmed, R.H et al. "TFF3 Is a Normal Breast Epithelial Protein and Is Associated with Differentiated Phenotype in Early Breast Cancer but Predisposes to Invasion and Metastasis in Advanced Disease," The American Journal of Pathology (Mar. 2012) 180(3), 904-916.
Babyatsky, Mark et al. "Trefoil factor-3 expression in human colon cancer liver metastasis," Clinical & Experimental Metastasis (2009) 26, 143-151.
Chen, Yi-Hua et al. "Transcription Factor NF-κB Signals Antianoikic Function of Trefoil Factor 3 on Intestinal Epithelial Cells," Biochemical and Biophysical Research Communications (2000) 274(3), 576-582.
Czabotar, P.E et al. "Bax activation by Bim?" Cell Death and Differentiation (2009) 16, 1187-1191.
Garraway, Isla P. et al. "Trefoil Factor 3 Is Overexpressed in Human Prostate Cancer," The Prostate (2004) 61, 209-214.
Khurana, Jitender M. et al. "DBU: a highly efficient catalyst for one-pot synthesis of substituted 3,4-dihydropyrano[3,2-c]chromenes, dihydropyrano[4,3-b]pyranes, 2-amino-4H-benzo[h]chromenes 2-amino-4H benzo[g]chromenes in aqueous medium," Tetrahedron (2010) 66, 5637-5641.
Kinoshita, Koichi et al. "Distinct Pathways of Cell Migration and Antiapoptotic Response to Epithelial Injury: Structure-Function Analysis of Human Intestinal Trefoil Factor," Molecular and Cellular Biology (Jul. 2000) 20(13), 4680-4590.
Muskett, Frederick W. et al. "Solution Structure of the Disulfide-Linked Dimer of Human Intestinal Trefoil Factor (TFF3): The Intermolecular Orientation and Interactions Are Markedly Different from Those of Other Dimeric Trefoil Proteins," Biochemistry (2003)42(51), 15139-15147.
Poulsen, Steen Seier et al. "Luminal and parenteral TFF2 and TFF3 dimer and monomer in two models of experimental colitis in the rat," Regulatory Peptides (2005) 126,163-171.
Rivat, Christine et al. "Implication of STAT3 Signaling in Human Colonic Cancer Cells during Intestinal Trefoil Factor 3 (TFF3)— and Vascular Endothelial Growth Factor-Mediated Cellular Invasion and Tumor Growth," Cancer Research (Jan. 1, 2005) 65(1), 195-202.
Taupin, D.R. et al. "Intestinal trefoil factor confers colonic epithelial resistance to apoptosis," PNAS (Proceedings of the National Academy of Sciences) (Jan. 18, 2000) 97(2), 799-804.
Taupin, Douglas et al. "The trefoil gene family are coordinately expressed immediate-early genese: EGF receptor—and MAP kinase-dependent interrugulation," The Journal of Clinical Investigation (1999) 103(9), R31-R38.
Weigelt, B. et al. "Marker genes for circulating tumour cells predict survival in metastasized breast cancer patients," British Journal of Cancer (2003) 88(7), 1091-1094.
Wong, W.M. et al. "Trefoil peptides," Gut (1999) 44, 890-895.
Xu, Xiu Qin et al. "Gene Expression Profiling to Identify Oncogenic Determinants of Autocrine Human Growth Hormone in Human Mammary Carcinoma," The Journal of Biological Chemistry (Jun. 24, 2005) 280(25), 23987-24003.
Yamachika, Takasuke et al. "Intestinal Trefoil Factor: A Marker of Poor Prognosis in Gastric Carcinoma," Clinical Cancer Research (May 2002) 8, 1092-1099.
Yip, K.W. et al. "Bcl-2 family proteins and cancer," Oncogene (2008) 27, 6398-6406.
Kirikoshi, Hiroyuki et al. "Expression of TFF1, TFF2, and TFF3 in gastric cancer," International Journal of Oncology (2002)21, 655-659.

\* cited by examiner

| Cells | | 43 (µM) | |
|---|---|---|---|
| | | IC$_{50}$ | ±SD |
| Normal | MCF10A | NV | NV |
| | MCF12A | NV | NV |
| TFF3-high | MCF7 | 3.21 | 1.84 |
| | T47D | 5.24 | 1.91 |
| | BT474 | 2.69 | 1.53 |
| | MDA-MB-361 | 1.61 | 0.85 |
| TFF3-low | BT20 | 467.9 | 22.81 |
| | MDA-MB-231 | 408.3 | 4.61 |
| | MDA-MB-436 | 395.7 | 32.82 |
| | MDA-MB-468 | NV | NV |

Footnote: NV, No value

COMPOUNDS USEFUL IN INHIBITING HUMAN TREFOIL FACTOR 3

CROSS-REFERENCE TO RELATED APPLICATIONS

This application is a national stage entry under 35 U.S.C. § 371 of PCT International Application No. PCT/SG2018/050277, filed Jun. 5, 2018, which claims priority to Singapore Patent Application No. 10201704579V, filed Jun. 5, 2017, the disclosures of both applications are expressly incorporated by reference in their entireties.

FIELD OF INVENTION

The current invention relates to compounds useful in inhibiting Human trefoil factor 3 and their uses.

BACKGROUND

The listing or discussion of an apparently prior-published document in this specification should not necessarily be taken as an acknowledgement that the document is part of the state of the art or is common general knowledge.

Human trefoil factor 3 (TFF3) is a small cysteine-rich protein belonging to the trefoil factor family (TFF) of proteins that share homology within a conserved trefoil domain of 42-43 amino acids with other members namely, TFF1 and TFF2. Structural analysis has determined that TFF3 forms a homodimer (through a disulfide linkage at Cys57) and the homodimer has been demonstrated to be required for bioactivity as compared to the monomeric form of TFF3.

Oestrogen responsive TFF3 has emerged as a clinically valuable and potent target in oncology. Specifically, TFF3 is absent or relatively low in normal tissues but significantly and prominently elevated in a wide-range of human malignancies, including mammary carcinoma (MC) where it is associated with the estrogen receptor (ER) positive (+) subtype. Moreover, increased levels of TFF3 protein were observed to be associated with advanced clinicopathological features of disease, such as tumor size, micro-vessel density, higher disease grade and metastases.

In addition, by both univariate and multivariate analyses, expression of TFF3 is significantly associated with poor prognosis of patients with various malignancies including MC, and is an independent prognostic factor. Whilst numerous other potential targets exhibit similar correlations, it is the significance of the associations for TFF3 that distinguish this target. For example, TFF3 (and TFF1) is the gene most significantly associated with micro-metastatic spread of MC to bone and TFF3 is the gene most significantly correlated with survival outcome of patients with ER+ MC treated with tamoxifen. Functionally, numerous experimental and clinical studies indicate a highly significant and potent role for TFF3 in the oncogenicity, proliferation and survival, angiogenesis and metastatic dissemination of various carcinoma derived cells. Conversely, siRNA-mediated depletion or polyclonal antibody based inhibition of TFF3 results in potent inhibition of cell survival both in in vitro and in vivo models.

One of the major survival mechanisms utilized by TFF3 is increased expression of BCL2, which is an anti-apoptotic protein, and decreased expression of BAX, which is a pro-apoptotic BCL2-family member. TFF3 function appears to be associated with multiple survival pathways including mitogen-activated protein kinase (MAPK), phosphatidylinositol-3-kinase-AKT (PI3K-AKT), STAT3 and nuclear factor kappa B (NF-κB). Enhanced BCL2 expression is most likely a consequence of combined activation of these survival pathways, resulting from increased TFF3 expression. TFF3 has recently been demonstrated to stimulate cellular invasion and metastasis of ER+MC cells in a Src-STAT3 dependent manner. Importantly, TFF3 reduces the sensitivity of ER+MC cells to anti-oestrogens (tamoxifen and fulvestrant) and depletion or inhibition of TFF3 restores tamoxifen sensitivity in tamoxifen resistant MC cell lines. In one cohort, TFF3 expression was observed in 44% of ER negative MC suggestive that TFF3 may also function in this recalcitrant subtype of MC.

A number of studies have determined that the homodimeric form of TFF3 is functionally active whereas the monomeric form is not. Homodimers of TFF3 are formed by use of the C-terminal cysteine residue (Cys57) of TFF3. Despite marked similarities in the primary sequence of members of the TFF family the tertiary structure of dimeric TFF3 is unique. The TFF3 dimer presents specific clusters of conserved surface hydrophobic residues which have been suggested to be critical for interaction with other proteins. Hence, there is an opportunity to develop small molecules specifically binding to or disrupting dimeric TFF3 (SMIT: small molecule inhibitor of TFF3) which would prevent interaction with secondary proteins and oncogenic signaling.

Thus, there is a need to develop better and efficient compounds/therapies for managing cancer by inhibiting dimerization and functions thereof. The present disclosure aims at providing such compounds.

DRAWINGS

In order that the disclosure may be readily understood and put into practical effect, reference will now be made to example embodiments as illustrated with reference to the accompanying figures. The figures together with the description serve to further illustrate the embodiments of the invention and explain various principles and advantages.

Figure 1C:
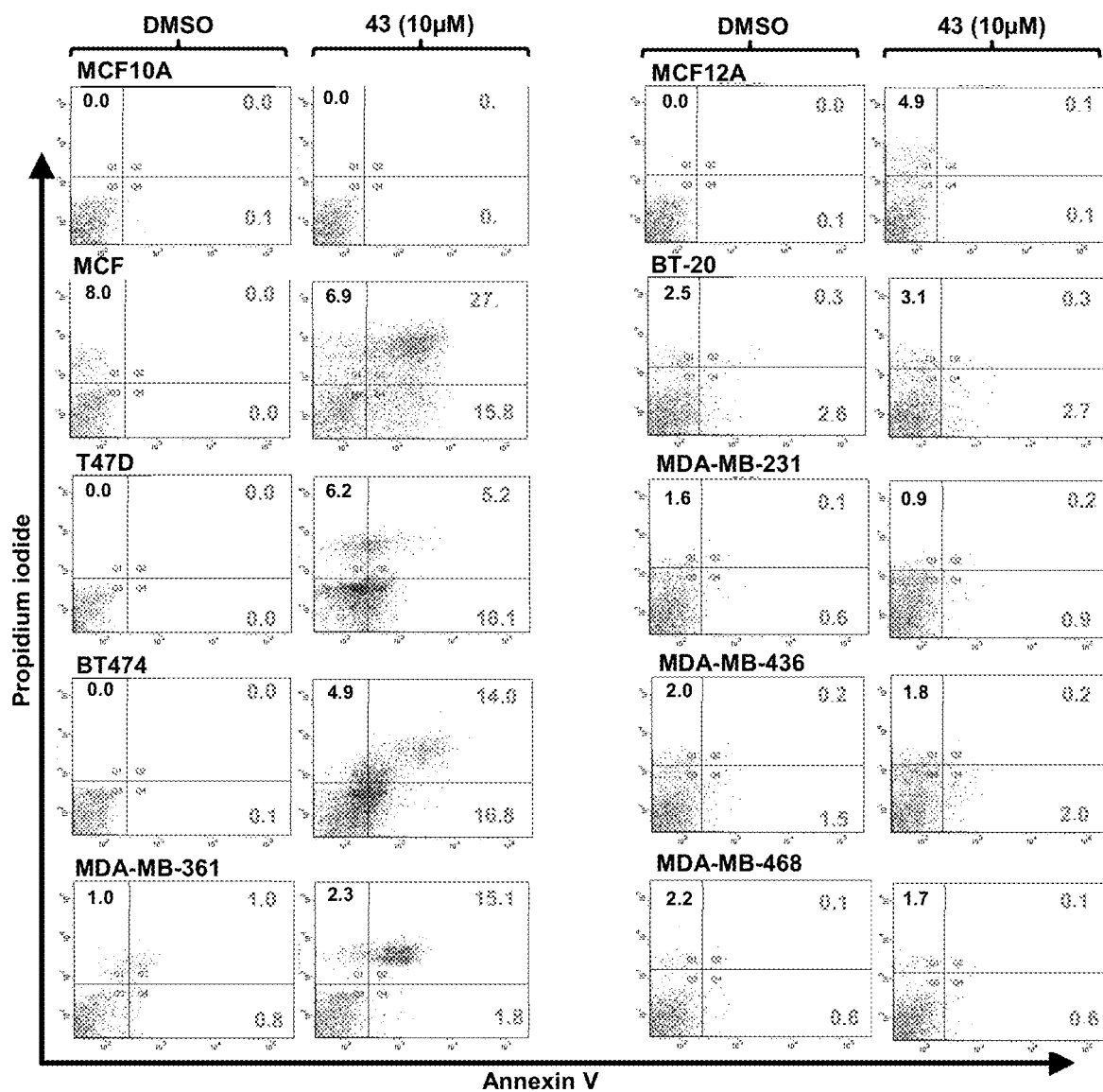
Figure 2A:
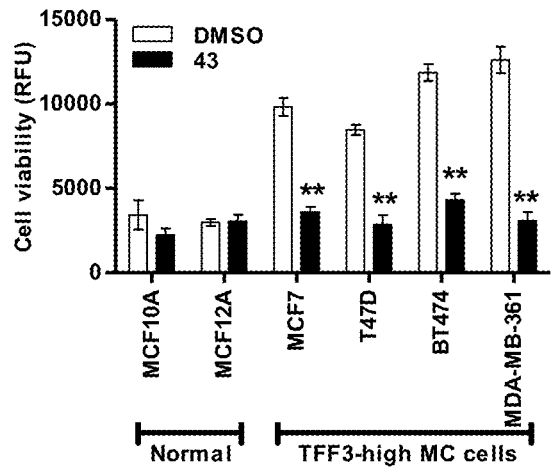
Figure 2B:
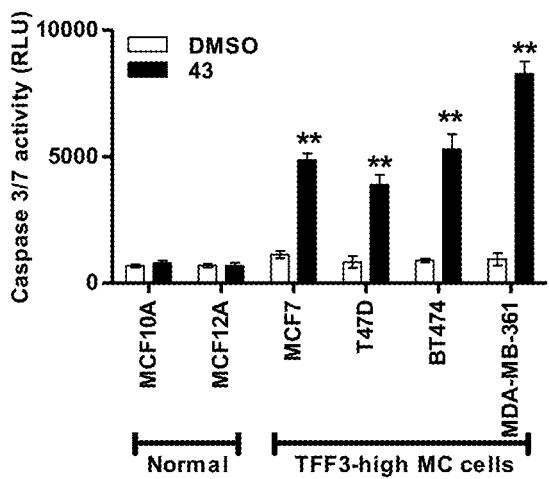
Figure 2C:
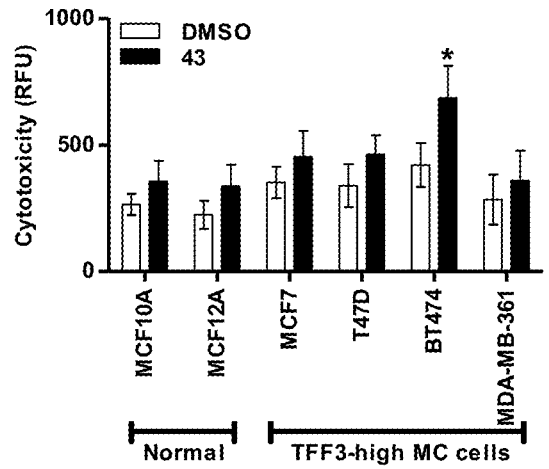
Figure 2D:
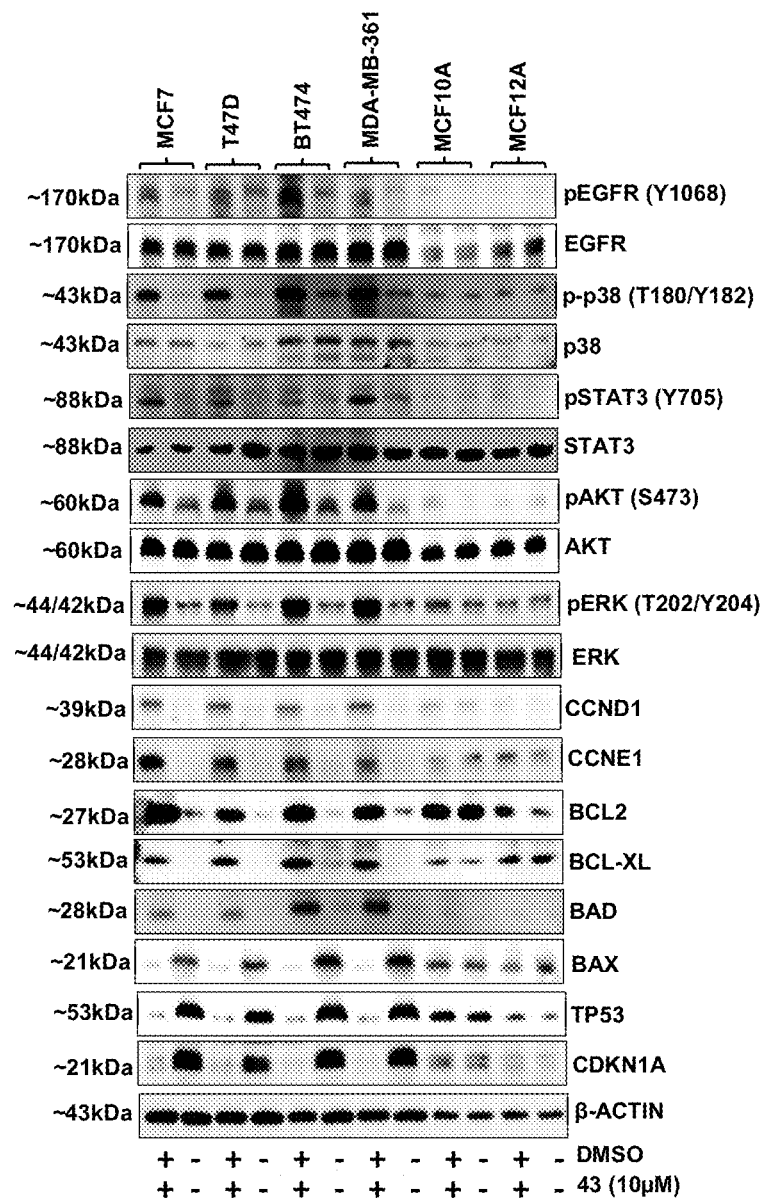

FIG. 1A-FIG. 1C: Compound 43 suppresses cell viability and stimulates apoptosis in TFF3-high expressing mammary carcinoma (MC) cell lines (FIG. 1A) Inhibitory concentration 50% (IC50) values for compound 43 in the MC cell lines are tabulated, using an AlamarBlue™ cell viability assay as previously described in Pandey V et al., Breast Cancer Res. 2014; 16(5):429. (FIG. 1B) Measured dose-dependent manner effect of compound 43 on the viability of MC cells (left-side, TFF3-high and right, TFF3-low) using AlamarBlue™ viability assay as previously described (ibid). (FIG. 1C) Apoptotic cell death of mammary carcinoma cell lines measured after treatment with 10 μM compound 43 using flow cytometry analysis at 24 hour as described previously in Keerthy HK et al., PloS one. 2014; 9(9):e107118. Annexin V-FITC staining is indicated on the X-axis and PI staining on the Y-axis. The lower left quadrant represents live cells, the lower right quadrant represents early apoptotic cells, the upper left quadrant represents necrotic cells and the upper right quadrants displays late apoptotic cells. Acquisition of Annexin V and PI data were represented as percentage (%) in each quadrant. Note: CM, conditioned media; MCF10A and MCF12A, non-transformed immortalized-mammary epithelial cell line. Points are mean of triplicate experiments; bars, ±SD. Statistical significance was assessed by using an unpaired two-tailed Student's t test (P<0.05 was considered as significant) using GraphPad Prism5. Columns are mean of triplicate experiments; bars, ±SD. **P <0.001, *P <0.05.

FIG. 2A-FIG. 2D: Compound 43 exposure stimulates intrinsic apoptosis in high-TFF3 expression MC cells.

Figure 3A:
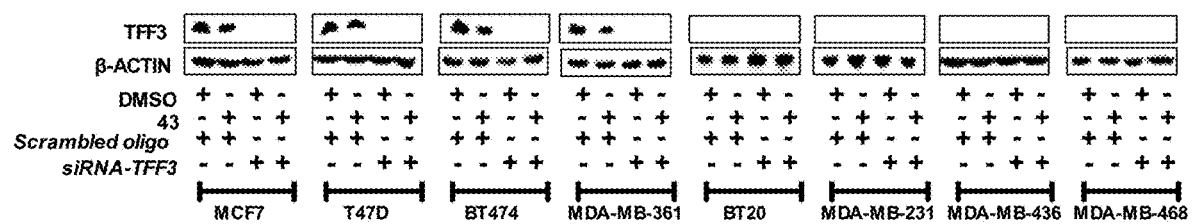
Figure 3B:
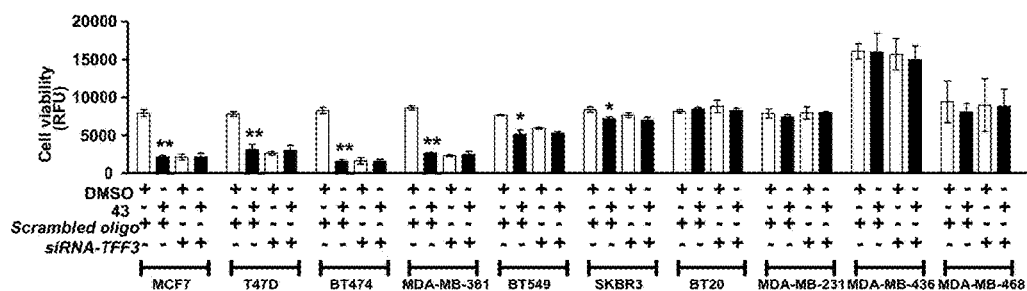
Figure 3C:
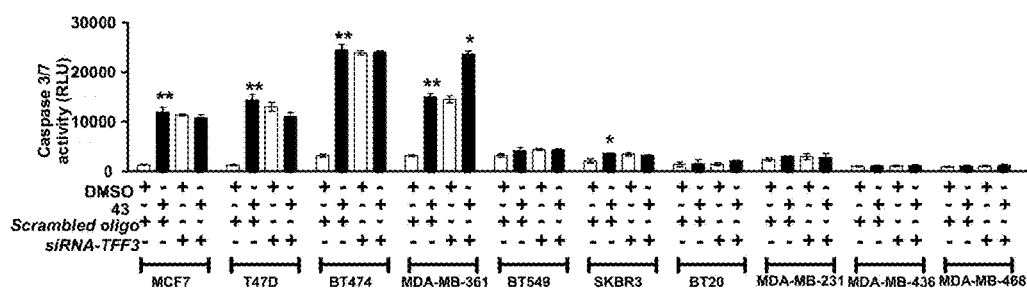

Effect of compound 43 (10 µM) on cell viability of high-TFF3 MC cell lines. (FIG. 2A) Cell viability (FIG. 2B) caspase 3/7 activities and (FIG. 2C) cytotoxicity was evaluated using ApoTox-Glo™ Triplex Assay Kit Promega (Singapore) according to manufacturer's instructions. Cell viability fluorescence is measured at $400_{Ex}/505_{Em}$, cytotoxicity fluorescence is measured at $485_{Ex}/520_{Em}$, while apoptosis (caspase 3/7 activities) is determined by luminescence measurement. (FIG. 2D) Western blot analysis was used to assess the level of various protein markers and protein activity in high-TFF3 expression MC cells after treatment with compound 43. Soluble whole cell extracts were run on a SDS-PAGE and immunoblotted as previously described in Pandey V et al., Breast Cancer Res. 2014; 16(5):429. β-ACTIN (ACTB) was used as input control for cell lysate. The sizes of detected protein bands in kDa are shown on the left side. Statistical significance was assessed by using an unpaired two-tailed Student's t test (P<0.05 was considered as significant) using GraphPad Prism5. Columns are mean of triplicate experiments; bars, ±SD. **P <0.001, *P <0.05. Note: RFU, relative fluorescence unit; RLU, relative luminescence unit, #; non-transformed, immortalized epithelial cells;

FIG. 3A-FIG. 3C: siRNA-mediated depletion of TFF3 expression revert effect of Compound 43 in TFF3-high expressing MC cells.

(FIG. 3A) Western blot analysis was used to assess the levels of TFF3 protein in MC cells after treatment with 5 µM compound 43 was used to treat cells. Depletion of TFF3 expression was achieved using transient-transfection of small interfering (si)-RNA (Invitrogen, Singapore) directed to TFF3 transcript as previously described in Pandey V et al., Breast Cancer Res. 2014; 16(5):429. Soluble whole cell extracts were run on a SDS-PAGE and immunoblotted as previously described (ibid). β-ACTIN was used as input control for cell lysate. Effects of compound 43 (5 µM) in MC cells. (FIG. 3B) Cell viability and (FIG. 3C) caspase 3/7 activities was evaluated using ApoTox-Glo™ Triplex Assay Kit, Promega (Singapore) according to manufacturer's instructions. Cell viability fluorescence is measured at $400_{Ex}/505_{Em}$, while apoptosis (caspase 3/7 activities) is determined with the luminescence measurement. Depletion of TFF3 expression was achieved using transient-transfection of small interfering (si)-RNA (Invitrogen, Singapore) directed to TFF3 transcript as previously described (ibid). Statistical significance was assessed by using an unpaired two-tailed Student's t test (P<0.05 was considered as significant) using GraphPad Prism5. Columns are mean of triplicate experiments; bars, ±SD. **P <0.001, *P <0.05. Note: RFU, relative fluorescence unit; RLU, relative luminescence unit.

FIG. 4A-FIG. 4F: Compound 43 suppresses cell viability in TFF3-high expressing mammary carcinoma cell in Matrigel 3D culture.

Figure 4A:
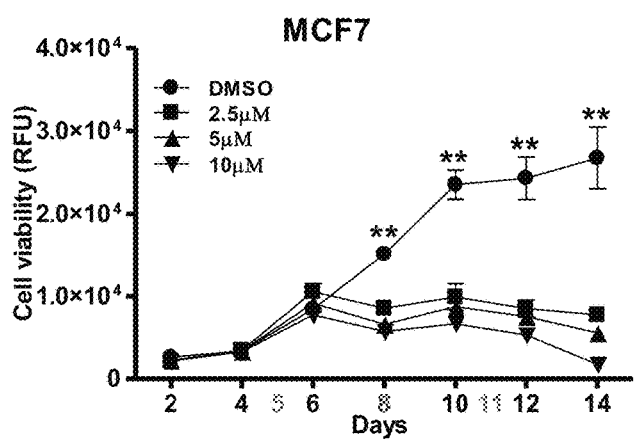
Figure 4D:
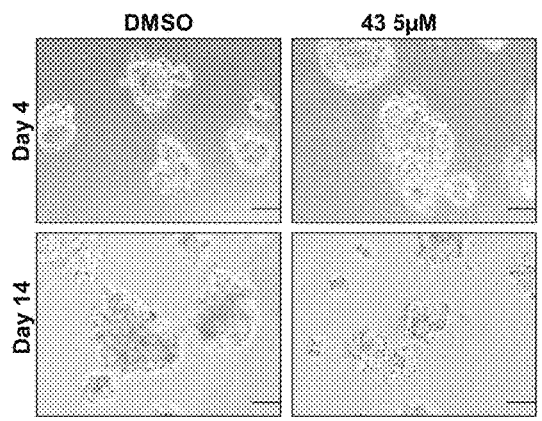
Figure 4B:
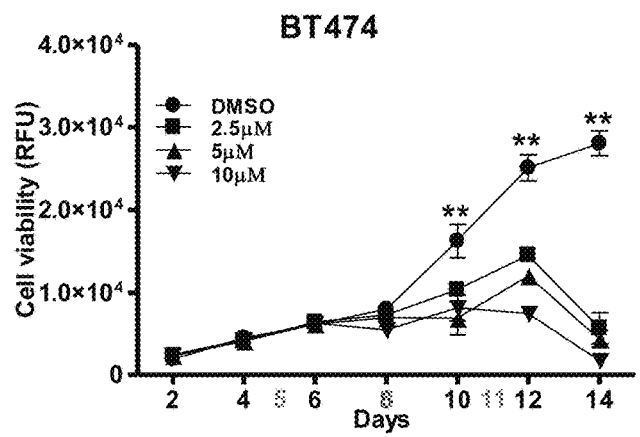
Figure 4E:
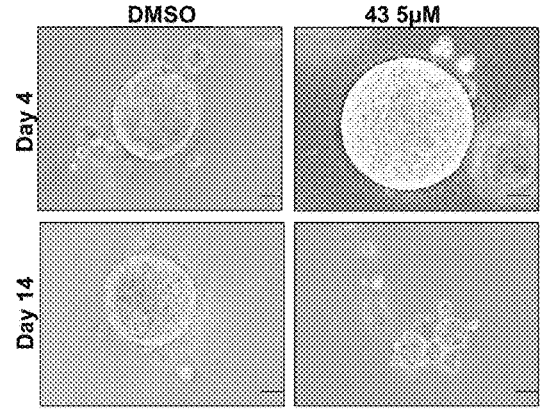
Figure 4C:
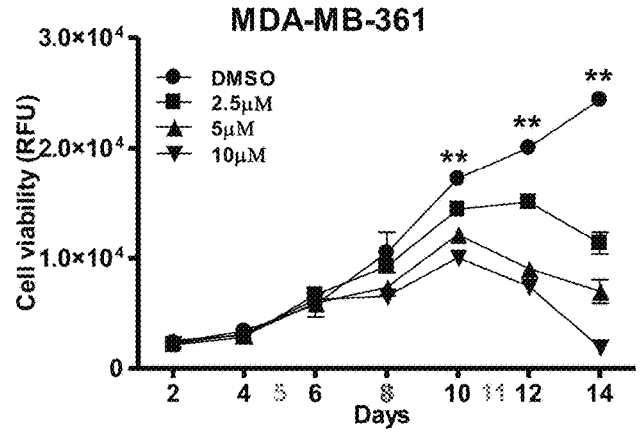
Figure 4F:
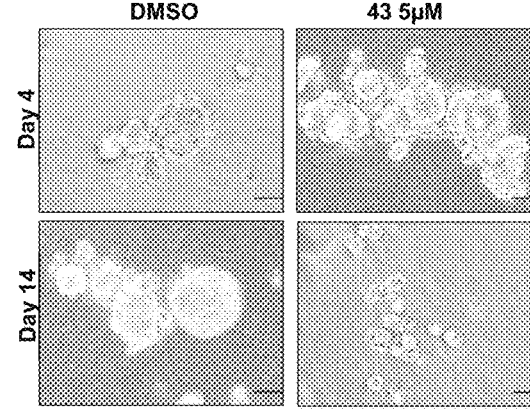

Cell viability in colonies generated by MCF7 FIG. 4A), BT474 FIG. 4B) and MDA-MB-361 FIG. 4C) cell after exposure with compound 43 or vehicle (DMSO) cultured 14 days in 3D Matrigel using AlamarBlue™ viability assay as previously described in Pandey V et al., Breast Cancer Res. 2014; 16(5):429. Microscopic visualization (right side) of colonies generated by MCF7 (FIG. 4D), BT474 (FIG. 4E) and MDA-MB-361 (FIG. 4F) cells after exposure with compound 43 or vehicle (DMSO) cultured 14 days in 3D Matrigel. On days 5, 8 and 11, colonies were treated with compound 43 or DMSO. Statistical significance was assessed by using an unpaired two-tailed Student's t test (P<0.05 was considered as significant) using GraphPad Prism5.

Figure 5A:
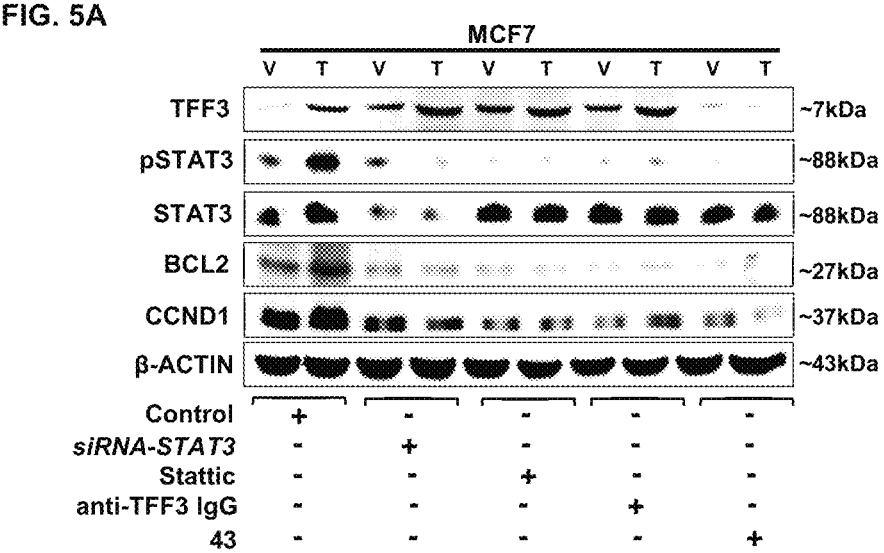
Figure 5B:
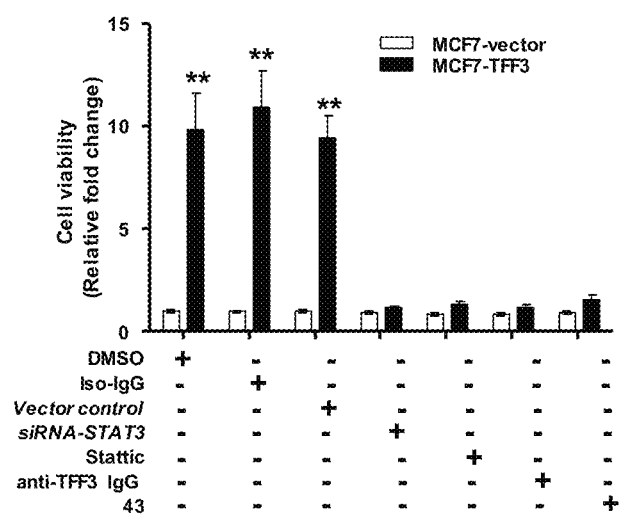
Figure 5C:
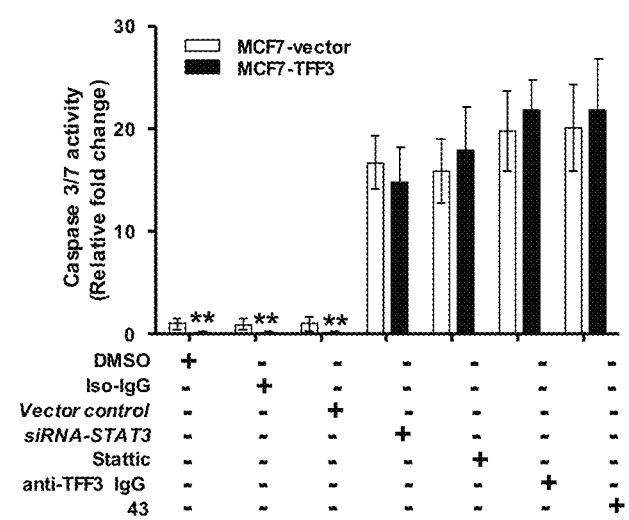
Figure 6A:
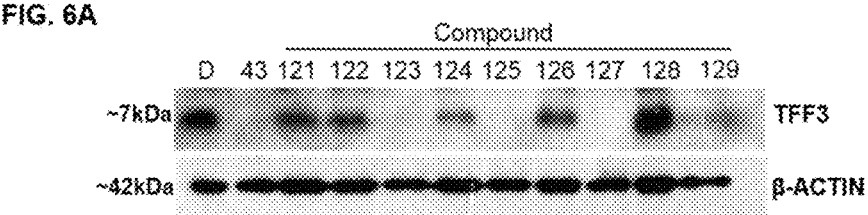
Figure 6B:
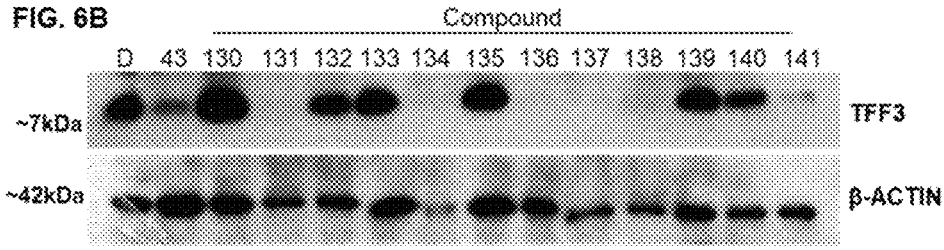
Figure 6C:
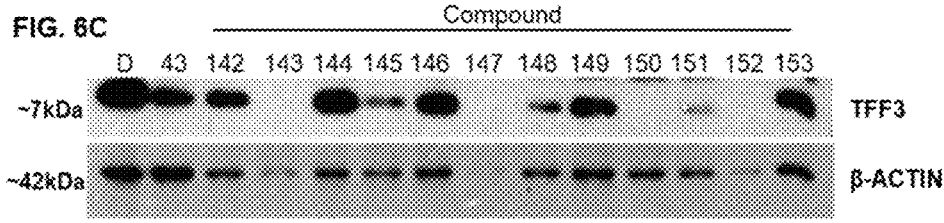
Figure 6D:
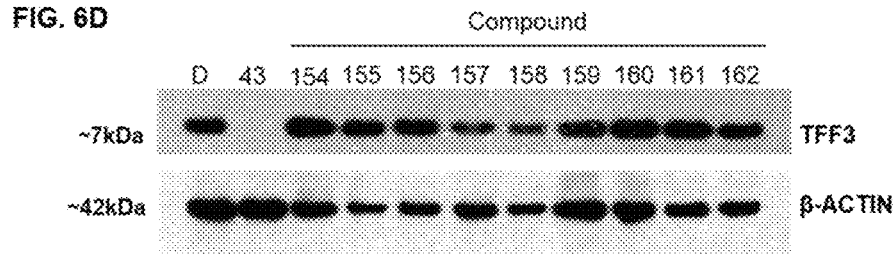
Figure 6E:
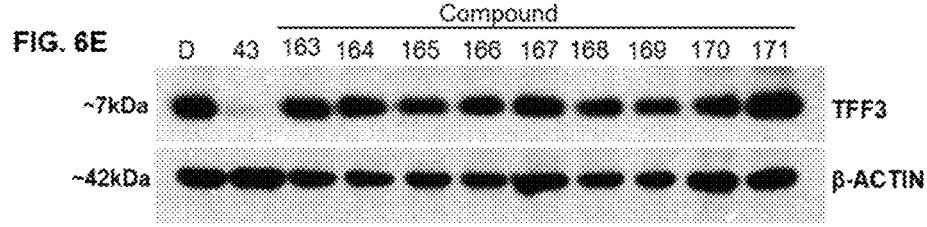

FIG. 5A-FIG. 5C: TFF3-stimulated effects in MCF7 cells reverted after exposure with Compound 43.

(FIG. 5A) Western blot analysis was used to assess the levels of pSTAT3, STAT3, BCL2, and CCND1 protein in MCF7 cells with forced expression of TFF3 after treatment with compound 43 (5 µM) and Stattic (2 µM) was used to treat cells. Depletion of STAT3 expression was achieved using transient-transfection of small interfering (si)-RNA (Invitrogen, Singapore) directed to STAT3 transcript as previously described in Pandey V et al., Breast Cancer Res. 2014; 16(5):429. Anti-TFF3 polyclonal antibody was used as previously described (ibid). Soluble whole cell extracts were run on a SDS-PAGE and immunoblotted as previously described (ibid). β-ACTIN was used as input control for cell lysate. The sizes of detected protein bands in kDa are shown on the right side (FIG. 5B) Cell viability and (FIG. 5C) caspase 3/7 activities in MCF7 cells with forced expression of TFF3 after treatment with compound 43 (5 µM) and Stattic (2 µM) was used to treat cells. Depletion of STAT3 expression was achieved using transient-transfection of small interfering (si)-RNA (Invitrogen, Singapore) directed to STAT3 transcript as previously described (ibid). Anti-TFF3 polyclonal antibody was used as previously described (ibid). Evaluated using ApoTox-Glo™ Triplex Assay Kit, Promega (Singapore) according to manufacturer's instructions. Cell viability fluorescence is measured at $400_{Ex}/505_{Em}$, while apoptosis (caspase 3/7 activities) is determined with the luminescence measurement. Depletion of TFF3 expression was achieved using transient-transfection of small interfering (si)-RNA (Invitrogen, Singapore) directed to TFF3 transcript as previously described (ibid). Statistical significance was assessed by using an unpaired two-tailed Student's t test (P<0.05 was considered as significant) using GraphPad Prism5. Columns are mean of triplicate experiments; bars, ±SD. **P <0.001, *P <0.05. Note: RFU, relative fluorescence unit; RLU, relative luminescence unit.

FIG. 6A-FIG. 6E: Efficacy of selected compounds (10 µM) on MCF7 cells and the expression of TFF3.

Western blot analysis was used to assess the protein levels of TFF3 in MCF7 cells after treatment with various compounds (10 µM). Cell were cultured in RPMI 1640 +2%FBS. Soluble whole cell extracts were run on a SDS-PAGE and immunoblotted as previously described in Pandey V et al., Breast Cancer Res. 2014; 16(5):429. β-ACTIN (ACTB) was used as input control for cell lysate (FIG. 6A-FIG. 6E). The sizes of detected protein bands in kDa are shown on the left side. Note: D, DMSO.

DESCRIPTION

We have discovered a series of small molecules that target TFF3 (e.g. dimeric TFF3) and have demonstrated pro-apoptotic efficacy and reduced cancer cell survival. 2-Amino-4-(4-(6-fluoro-5-methylpyridin-3-yl)phenyl)-5-oxo-4H,5H-pyrano[3,2-c]chromene-3-carbonitrile (AMPC) has been identified as one of the compounds that inhibit TFF3 (e.g. TFF3 dimerization) and functions thereof. The in vitro and in vivo inhibitory activity of AMPC against TFF3 (e.g. dimeric TFF3) has also been experimentally validated as discussed in more detail below.

Thus, according to a first aspect of the invention, there is provided a compound of formula I:

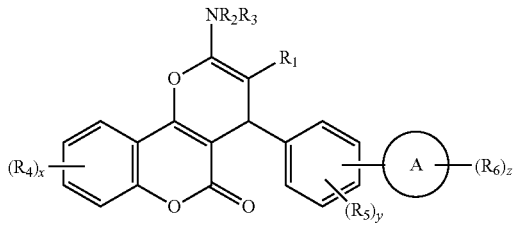

wherein:
R$_1$ represents CN or Het$^a$, which latter group is unsubstituted or substituted by halo, C$_{1-6}$ alkyl, C$_{2-6}$ alkenyl, C$_{2-6}$ alkynyl, or C$_{3-6}$ cycloalkyl, which latter four groups are unsubstituted or substituted by one or more substituents selected from halo, OH and NH$_2$;

R$_2$ and R$_3$ independently represent H, C(O)R$_7$, S(O)$_x$R$_{7'}$, C$_{1-6}$ alkyl, C$_{2-6}$ alkenyl, C$_{2-6}$ alkynyl, or C$_{3-6}$ cycloalkyl, which latter four groups are unsubstituted or substituted by one or more substituents selected from halo, OH and NH$_2$; or R$_1$ and R$_2$ and/or R$_3$, together with the atoms they are attached to, form a heterocyclic or heteroaromatic ring system having from 9 to 10 atoms in the ring system, which ring system is unsubstituted or substituted by one or more groups selected from =S, =O, halo, C$_{1-6}$ alkyl, C$_{2-6}$ alkenyl, C$_{2-6}$ alkynyl, C$_{3-6}$ cycloalkyl, aryl, or Het$^b$, which latter six groups are unsubstituted or substituted by one or more substituents selected from halo, OR$_6$ and NR$_9$R$_{10}$;

each R$_4$ independently represents halo, C$_{1-6}$ alkyl, C$_{2-6}$ alkenyl, C$_{2-6}$ alkynyl, C$_{3-6}$ cycloalkyl, (which latter four groups are unsubstituted or substituted by one or more substituents selected from halo, OH and NH$_2$) OR$_{11}$, or NR$_{12}$R$_{13}$, each R$_6$ independently represents halo, C$_{1-6}$ alkyl, C$_{2-6}$ alkenyl, C$_{2-6}$ alkynyl, C$_{3-6}$ cycloalkyl, (which latter four groups are unsubstituted or substituted by one or more substituents selected from halo, OH and NH$_2$), OR$_{14}$, or NR$_{15}$R$_{16}$;

each R$_6$ independently represents halo, C$_{1-6}$ alkyl, C$_{2-6}$ alkenyl, C$_{2-6}$ alkynyl, C$_{3-6}$ cycloalkyl, (which latter four groups are unsubstituted or substituted by one or more substituents selected from halo, OH and NH$_2$), OR$_{17}$, or NR$_{18}$R$_{19}$;

R$_7$ and R$_{7'}$ independently represent Het$^c$, aryl, C$_{1-6}$ alkyl, C$_{2-6}$ alkenyl, C$_{2-6}$ alkynyl, or C$_{3-6}$ cycloalkyl, which latter five groups are unsubstituted or substituted by one or more substituents selected from aryl (which group is unsubstituted or substituted by one or more of C$_{1-6}$ alkyl, alkoxy, halo, NO$_2$, OH and NH$_2$), alkoxy, C$_{1-3}$ alkyl, Het$^d$, halo, OH and NH$_2$;

R$_8$, R$_{11}$, R$_{14}$ and R$_{17}$ each independently represent at each occurrence thereof H, C$_{1-6}$ alkyl, C$_{2-6}$ alkenyl, C$_{2-6}$ alkynyl, or C$_{3-6}$ cycloalkyl, which latter four groups are unsubstituted or substituted by one or more substituents selected from halo, alkoxy, OH and NH$_2$;

R$_9$, R$_{10}$, R$_{12}$, R$_{13}$, R$_{15}$, R$_{16}$, R$_{18}$, and R$_{19}$ each independently represent at each occurrence thereof H, C$_{1-6}$ alkyl, C$_{2-6}$ alkenyl, C$_{2-6}$ alkynyl, or C$_{3-6}$ cycloalkyl, which latter four groups are unsubstituted or substituted by one or more substituents selected from halo, alkoxy, OH and NH$_2$;

Het$^a$ to Het$^d$ independently represent, at each occurrence, a 5- or 6-membered heterocyclic or heteroaromatic groups containing one or more heteroatoms selected from 0, S and N, which heterocyclic groups are optionally substituted by one or more substituents selected from =O, =S, halo, OH, C$_{1-4}$ alkyl and C$_{1-4}$ alkoxy, which latter two groups are optionally substituted by one or more substituents selected from halo, OH and NH$_2$;

A represents a 5- to 13-membered carbocyclic or heterocyclic ring system that is aromatic and/or non-aromatic;

x is from 0 to 4;
x' is from 1 to 2;
y is from 0 to 5; and
z is from 0 to 5, or a pharmaceutically acceptable salt or solvate, or a deuteriated compound of the Formula I or a pharmaceutically functional derivative thereof.

References herein (in any aspect or embodiment of the invention) to compounds of formula I includes references to such compounds per se, to tautomers of such compounds, as well as to pharmaceutically acceptable salts or solvates, or pharmaceutically functional derivatives of such compounds.

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable salts include acid addition salts derived from mineral acids and organic acids, and salts derived from metals such as sodium, magnesium, or preferably, potassium and calcium.

Examples of acid addition salts include acid addition salts formed with acetic, 2,2-dichloroacetic, adipic, alginic, aryl sulphonic acids (e.g. benzenesulphonic, naphthalene-2-sulphonic, naphthalene-1,5-disulphonic and p-toluenesulphonic), ascorbic (e.g. L-ascorbic), L-aspartic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, tartaric (e.g. (+)-L-tartaric), thiocyanic, undecylenic and valeric acids.

Particular examples of salts are salts derived from mineral acids such as hydrochloric, hydrobromic, phosphoric, metaphosphoric, nitric and sulphuric acids; from organic acids, such as tartaric, acetic, citric, malic, lactic, fumaric, benzoic, glycolic, gluconic, succinic, arylsulphonic acids; and from metals such as sodium, magnesium, or preferably, potassium and calcium.

As mentioned above, also encompassed by formula I are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent).

Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravirmetric analysis (TGE), differential scanning calorimetry (DSC) and X-ray crystallography.

The solvates can be stoichiometric or non-stoichiometric solvates. Particularly preferred solvates are hydrates, and examples of hydrates include hemihydrates, monohydrates and dihydrates. For a more detailed discussion of solvates and the methods used to make and characterise them, see Bryn et al., *Solid-State Chemistry of Drugs*, Second Edition, published by SSCI, Inc of West Lafayette, Ind., USA, 1999, ISBN 0-967-06710-3.

"Pharmaceutically functional derivatives" of compounds of formula I as defined herein includes ester derivatives and/or derivatives that have, or provide for, the same biological function and/or activity as any relevant compound of the invention. Thus, for the purposes of this invention, the term also includes prodrugs of compounds of formula L.

The term "prodrug" of a relevant compound of formula I includes any compound that, following oral or parenteral administration, is metabolised in vivo to form that compound in an experimentally-detectable amount, and within a predetermined time (e.g. within a dosing interval of between 6 and 24 hours (i.e. once to four times daily)).

Prodrugs of compounds of formula I may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds of formula I wherein a hydroxyl, amino, sulfhydryl, carboxyl or carbonyl group in a compound of formula I is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, esters groups of carboxyl functional groups, N-acyl derivatives and N-Mannich bases. General information on prodrugs may be found e.g. in Bundegaard, H. "Design of Prodrugs" p. I-92, Elsevier, New York-Oxford (1985).

Compounds of formula I, as well as pharmaceutically acceptable salts, solvates and pharmaceutically functional derivatives of such compounds are, for the sake of brevity, hereinafter referred to together as the "compounds of formula I".

Compounds of formula I may contain double bonds and may thus exist as E (entgegen) and Z (zusammen) geometric isomers about each individual double bond. All such isomers and mixtures thereof are included within the scope of the invention.

Compounds of formula I may exist as regioisomers and may also exhibit tautomerism. All tautomeric forms and mixtures thereof are included within the scope of the invention.

Compounds of formula I may, in certain embodiments, contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

The compound of formula I in the above-mentioned aspect of the invention may be utilised in a method of medical treatment. Thus, according to further aspects of the invention, there is provided:

(a) a compound of formula I, or a pharmaceutically acceptable salt or solvate, or a pharmaceutically functional derivative thereof, for use in medicine;

(b) a compound of formula I, or a pharmaceutically acceptable salt or solvate, or a pharmaceutically functional derivative thereof, for use in the treatment of a condition or disorder ameliorated by the inhibition of human trefoil factor 3;

(c) use of a compound of formula I, or a pharmaceutically acceptable salt or solvate, or a pharmaceutically functional derivative thereof, for the preparation of a medicament for the treatment of a condition or disorder ameliorated by the inhibition of human trefoil factor 3; and (d) a method of the treatment of a condition or disorder ameliorated by the inhibition of human trefoil factor 3, which method comprises the administration of an effective amount of a compound of formula I, or a pharmaceutically acceptable salt or solvate, or a pharmaceutically functional derivative thereof.

The term "a condition or disorder ameliorated by the inhibition of human trefoil factor 3" will be understood by those skilled in the art to include a hyperproliferative disease or disorder. The term "a hyperproliferative disease or disorder" will be understood by those skilled in the art to include a hyperproliferative vascular disease (such as intimal smooth muscle cell hyperplasia, restenosis, and vascular occlusion), a hyperproliferative skin disease (such as psoriasis) and cancer (such as adrenal cancer, anal cancer, bile duct cancer, bladder cancer, bone cancer, brain tumours, CNS tumours, breast cancer, Castleman disease, cervical cancer, colon cancer, rectum cancer, endometrial cancer, esophagus cancer, eye cancer, gallbladder cancer, gastrointestinal carcinoid tumors, gastrointestinal stromal tumor (GIST), gestational trophoblastic disease, Hodgkin disease, Kaposi sarcoma, kidney cancer, laryngeal cancer, hypopharyngeal cancer, leukemia (e.g. acute lymphocytic, acute myeloid, chronic lymphocytic, chronic myeloid, chronic myelomonocytic), liver cancer, lung cancer (e.g. small cell or non-small cell), lung carcinoid tumour, lymphoma (e.g. of the skin), malignant mesothelioma, multiple myeloma, myelodysplastic syndrome, nasal cavity cancer, paranasal sinus cancer, nasopharyngeal cancer, neuroblastoma, non-Hodgkin lymphoma, oral cavity cancer, oropharyngeal cancer, osteosarcoma, ovarian cancer, pancreatic cancer, penile cancer, pituitary tumours, prostate cancer, retinoblastoma, rhabdomyosarcoma, salivary gland cancer, sarcoma, skin cancer (basal and squamous cell, melanoma, Merkel cell), small intestine cancer, stomach cancer, testicular cancer, thymus cancer, thyroid cancer, uterine sarcoma, vaginal cancer, vulvar cancer, Waldenstrom macroglobulinemia, Wilms tumour).

Particular hyperproliferative diseases or disorders that may be mentioned herein include solid tumours (such as adrenal cancer, anal cancer, bile duct cancer, bladder cancer, bone cancer, brain tumours, CNS tumours, breast cancer, Castleman disease, cervical cancer, colon cancer, rectum cancer, endometrial cancer, esophagus cancer, eye cancer, gallbladder cancer, gastrointestinal carcinoid tumors, gastrointestinal stromal tumor (GIST), gestational trophoblastic disease, Hodgkin disease, Kaposi sarcoma, kidney cancer, laryngeal cancer, hypopharyngeal cancer, liver cancer, lung cancer (e.g. small cell or non-small cell), lung carcinoid tumour, malignant mesothelioma, multiple myeloma, myelodysplastic syndrome, nasal cavity cancer, paranasal sinus cancer, nasopharyngeal cancer, neuroblastoma, oral cavity cancer, oropharyngeal cancer, osteosarcoma, ovarian cancer, pancreatic cancer, penile cancer, pituitary tumours, prostate cancer, retinoblastoma, rhabdomyosarcoma, salivary gland cancer, sarcoma, skin cancer (basal and squamous cell, melanoma, Merkel cell), small intestine cancer, stomach cancer, testicular cancer, thymus cancer, thyroid cancer, uterine sarcoma, vaginal cancer, vulvar cancer, Waldenstrom macroglobulinemia, Wilms tumour). Yet more particular hyperproloferative diseases or disorders that may be mentioned herein include breast cancer, endometrial cancer, lung cancer (e.g. small cell or non-small cell), lung carcinoid tumour, liver cancer, colon cancer, prostate cancer, pancreatic cancer, thyroid cancer, gastrointestinal carcinoid tumors, and gastrointestinal stromal tumor (GIST).

It will be appreciated that, for the compounds of formula I to be effective, it is necessary that there is overexpression of TFF3 within the subject (e.g. within the cancer cells to be treated). Examples of cell lines with such overexpression are, but are not limited to, mammary cell lines: MCF7, T47D, BT474, MDA-MB-361; endometrial cell lines: Ishikawa, ECC1; lung cell lines: HCC-827, HCC-4006, NCI-H1975, NCI-H1299, PC-14; hepatocellular cell lines: Hep3B, H2P, H2M; colon cell lines: DLD-1, Caco-2; prostate cell lines: PC3, DU145; pancreatic cell lines: AsPC-1, BxPC-3; thyroid cell lines: HTH83, CAL62; and gastric cell lines: AGS, MKN-45 and A2-528.

To determine whether a cell line has high or low expression of TFF3, the endogenous expression of TFF3 in cancer cell lines can be measured using qPCR and western blot analysis. Expression of TFF3 in cancer cell lines can be normalized with Beta-ACTIN gene expression. Based on the data analysed, cancer cell lines can then be sub-categorized as high/normal and low/negative TFF3 expressing cancer cells based on the results obtained.

For the avoidance of doubt, in the context of the present invention, the term "treatment" includes references to therapeutic or palliative treatment of patients in need of such treatment, as well as to the prophylactic treatment and/or diagnosis of patients which are susceptible to the relevant disease states.

The terms "patient" and "patients" include references to mammalian (e.g. human) patients. As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and newborn subjects, whether male or female, are intended to be covered.

The term "effective amount" refers to an amount of a compound, which confers a therapeutic effect on the treated patient (e.g. sufficient to treat or prevent the disease). The effect may be objective (i.e. measurable by some test or marker) or subjective (i.e. the subject gives an indication of or feels an effect).

Unless otherwise stated, the term "alkyl" refers to an unbranched or branched, cyclic, saturated or unsaturated (so forming, for example, an alkenyl or alkynyl) hydrocarbyl radical, which may be substituted or unsubstituted (with, for example, one or more halo atoms). Where the term "alkyl" refers to an acyclic group, it is preferably $C_{1-10}$ alkyl and, more preferably, $C_{1-6}$ alkyl (such as ethyl, propyl, (e.g. n-propyl or isopropyl), butyl (e.g. branched or unbranched butyl), pentyl or, more preferably, methyl). Where the term "alkyl" is a cyclic group (which may be where the group "cycloalkyl" is specified), it is preferably $C_{3-12}$ cycloalkyl and, more preferably, $C_{5-10}$ (e.g. $C_{5-7}$) cycloalkyl.

Unless otherwise stated, the term "alkylene" refers to an unbranched or branched $C_{1-10}$ (e.g. $C_{1-5}$) alkylene and, preferably $C_{1-3}$ alkylene, such as pentylene, butylene (branched or unbranched), preferably, propylene (n-propylene or isopropylene), ethylene or, more preferably, methylene (i.e. —$CH_2$—).

The term "halo", when used herein, includes references to fluoro, chloro, bromo and iodo.

Unless otherwise stated, the term "aryl" when used herein includes $C_{6-14}$ (such as $C_{6-10}$) aryl groups. Such groups may be monocyclic, bicyclic or tricyclic and have between 6 and 14 ring carbon atoms, in which at least one ring is aromatic. The point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like, such as 1,2,3,4-tetrahydronaphthyl, indanyl, indenyl and fluorenyl. Embodiments of the invention that may be mentioned include those in which aryl is phenyl.

Heterocyclic (A and $Het^a$ to $Het^d$) groups may be fully saturated, partly unsaturated, wholly aromatic or partly aromatic in character. Values of the A group that may be mentioned include acridinyl, 1-azabicyclo[2.2.2]octanyl, benzimidazolyl, benzisothiazolyl, benzisoxazolyl, benzodioxanyl, benzodioxepanyl, benzodioxepinyl, benzodioxolyl, benzofuranyl, benzofurazanyl, benzo[c]isoxazolidinyl, benzomorpholinyl, 2,1,3-benzoxadiazolyl, benzoxazinyl (including 3,4-dihydro-2H-1,4-benzoxazinyl), benzoxazolidinyl, benzoxazolyl, benzopyrazolyl, benzo[e]pyrimidine, 2,1, 3-benzothiadiazolyl, benzothiazolyl, benzothienyl, benzotriazolyl, carbazolyl, chromanyl, chromenyl, cinnolinyl, 2,3-dihydrobenzimidazolyl, 2,3-dihydrobenzo[6]furanyl, 1,3-dihydrobenzo[c]furanyl, 1,3-dihydro-2,1-benzisoxazolyl, 2,3-dihydropyrrolo[2,3-b]pyridinyl, dioxanyl, furanyl, furazanyl, hexahydropyrimidinyl, hydantoinyl, imidazolyl, imidazo[1,2-a]pyridinyl, imidazo[2,3-b]thiazolyl, indazolyl, indolinyl, indolyl, isobenzofuranyl, isochromanyl, isoindolinyl, isoindolyl, isoquinolinyl, isothiazolyl, isothiochromanyl, isoxazolidinyl, isoxazolyl, maleimido, morpholinyl, naphtho[1,2-b]furanyl, naphthyridinyl (including 1,6-naphthyridinyl or, particularly, 1,5-naphthyridinyl and 1,8-naphthyridinyl), oxadiazolyl, 1,2- or 1,3-oxazinanyl, oxazolyl, phenazinyl, phenothiazinyl, phthalazinyl, piperazinyl, piperidinyl, pteridinyl, purinyl, pyranyl, pyrazinyl, pyrazolyl, pyridazinyl, pyridinyl, pyrimidinyl, pyrrolidinonyl, pyrrolidinyl, pyrrolinyl, pyrrolo[2,3-b]pyridinyl, pyrrolo[5,1-b]pyridinyl, pyrrolo[2,3-c]pyridinyl, pyrrolyl, quinazolinyl, quinolinyl, quinolizinyl, quinoxalinyl, sulfolanyl, 3-sulfolenyl, 4,5,6,7-tetrahydrobenzimidazolyl, 4,5,6,7-tetrahydrobenzopyrazolyl, 5,6,7,8-tetrahydrobenzo[e]pyrimidine, tetrahydrofuranyl, tetrahydroisoquinolinyl (including 1,2,3,4-tetrahydroisoquinolinyl and 5,6,7,8-tetrahydroisoquinolinyl), tetrahydropyranyl, 3,4,5,6-tetrahydropyridinyl, 1,2,3,4-tetrahydropyrimidinyl, 3,4,5,6-tetrahydropyrimidinyl, tetrahydroquinolinyl (including 1,2,3,4-tetrahydroquinolinyl and 5,6,7,8-tetrahydroquinolinyl), tetrazolyl, thiadiazolyl, thiazolidinyl, thiazolyl, thienyl, thieno[5,1-c]pyridinyl, thiochromanyl, thiophenetyl, triazolyl, 1,3,4-triazolo[2,3-b]pyrimidinyl, xanthenyl and the like. Particular values of A that may be mentioned include the 5- to 10-membered heterocyclic groups from the list above. Further, values of A that may be mentioned include the 5- and 8-membered (e.g. 5- to 6-membered) heterocyclic groups from the list above. A particular value of A that may be mentioned herein is pyridyl.

Values of $Het^a$ to $Het^d$ that may be mentioned include the 5- or 6-membered heterocyclic (and heteroaromatic) groups from the list above. In particular embodiments, $Het^2$ may be pyrrolyl.

Substituents on heterocyclic (A and $Het^a$ to $Het^d$) groups may, where appropriate, be located on any atom in the ring system including a heteroatom. The point of attachment of heterocyclic (A and $Het^a$ to $Het^d$) groups may be via any atom in the ring system including (where appropriate) a heteroatom (such as a nitrogen atom), or an atom on any fused carbocyclic ring that may be present as part of the ring system. Heterocyclic (A and $Het^a$ to $Het^d$) groups may also be in the N- or S-oxidised form.

For the avoidance of doubt, in cases in which the identity of two or more substituents in a compound of formula I may be the same, the actual identities of the respective substituents are not in any way interdependent.

Embodiments of the invention that may be mentioned include those that relate to compounds of formula I in which:

$R_1$ represents CN or Het, which latter group is unsubstituted or substituted by halo, $C_{1-6}$ alkyl, which latter four group is unsubstituted or substituted by one or more substituents selected from halo, OH and $NH_2$;

$R_2$ and $R_3$ independently represent H, $C(O)R_7$, $S(O)_xR_7$, $C_{1-6}$ alkyl, which latter group is unsubstituted or substituted by one or more substituents selected from halo, OH and $NH_2$;

each $R_4$ independently represents halo, $C_{1-6}$ alkyl (which latter group is unsubstituted or substituted by one or more substituents selected from halo, OH and $NH_2$), $OR_{11}$, or $NR_{12}R_{13}$, each $R_5$ independently represents halo, $C_{1-6}$ alkyl (which latter group is unsubstituted or substituted by one or more substituents selected from halo, OH and $NH_2$), $OR_{14}$, or $NR_{15}R_{16}$;

each $R_6$ independently represents halo, $C_{1-6}$ alkyl (which latter group is unsubstituted or substituted by one or more substituents selected from halo, OH and $NH_2$), $OR_{17}$, or $NR_{18}R_{19}$;

$R_7$ and $R_{7'}$ independently represent $Het^c$, aryl, $C_{1-6}$ alkyl, which latter two groups are unsubstituted or substituted by one or more substituents selected from aryl (which group is unsubstituted or substituted by one or more of $C_{1-6}$ alkyl, alkoxy, halo, $NO_2$, OH and $NH_2$), alkoxy, $C_{1-3}$ alkyl, $Het^d$, halo, OH and $NH_2$;

$R_{11}$, $R_{14}$ and $R_{17}$ each independently represent at each occurrence thereof H, $C_{1-6}$ alkyl, $C_{2-6}$ alkenyl, $C_{2-6}$ alkynyl, or $C_{3-6}$ cycloalkyl, which latter four groups are unsubstituted or substituted by one or more substituents selected from halo, alkoxy, OH and $NH_2$;

$R_{12}$, $R_{13}$, $R_{15}$, $R_{16}$, $R_{18}$, and $R_{19}$ each independently represent at each occurrence thereof H, $C_{1-6}$ alkyl, which latter group is unsubstituted or substituted by one or more substituents selected from halo, alkoxy, OH and $NH_2$;

$Het^a$, $Het^c$ and $Het^e$ independently represent, at each occurrence, a 5- or 6-membered heterocyclic or heteroaromatic group containing one or more heteroatoms selected from O, S and N, which heterocyclic groups are optionally substituted by one or more substituents selected from =O, =S, halo, OH, $C_{1-4}$ alkyl and $C_{1-4}$ alkoxy, which latter two groups are optionally substituted by one or more substituents selected from halo, OH and $NH_2$;

A represents a 5- to 13-membered carbocyclic or heterocyclic ring system that is aromatic and/or non-aromatic;

x is from 0 to 4;

x' is from 1 to 2;

y is from 0 to 5; and z is from 0 to 5.

Further embodiments of the invention that may be mentioned include those that relate to compounds of formula I in which:

(a) $R_1$ represents CN or $Het^a$, which latter group is unsubstituted or substituted by halo, $C_{1-6}$ alkyl, $C_{2-6}$ alkenyl, $C_{2-6}$ alkynyl, or $C_{3-6}$ cycloalkyl, which latter four groups are unsubstituted or substituted by one or more substituents selected from halo, OH and $NH_2$;

(b) $R_2$ and $R_3$ independently represent H, $C(O)R_7$, $S(O)_xR_7$, $C_{1-6}$ alkyl, $C_{2-6}$ alkenyl, $C_{2-6}$ alkynyl, or $C_{3-6}$ cycloalkyl, which latter four groups are unsubstituted or substituted by one or more substituents selected from halo, OH and $NH_2$ (e.g. $R_2$ and $R_3$ independently represent H, $C(O)R_7$ and $S(O)_2R_{7'}$, optionally wherein $R_2$ represents H and $R_3$ represents H or $C(O)R_7$);

(c) when present, each $R_4$ independently represents halo, $C_{1-3}$ alkyl (which latter group is unsubstituted or substituted by one or more substituents selected from halo, OH and $NH_2$), or $OR_{11}$;

(d) when present, each $R_5$ independently represents halo, $C_{1-6}$ alkyl (which latter group is unsubstituted or substituted by one or more substituents selected from halo, OH and $NH_2$), $OR_{14}$, or $NR_{15}R_{16}$;

(e) when present, each $R_6$ independently represents halo, $C_{1-3}$ alkyl (which latter group is unsubstituted or substituted by one or more substituents selected from halo, OH and $NH_2$), or $OR_{17}$.

(f) when present, $R_7$ represents $Het^c$, or $C_{1-3}$ alkyl, which latter group is aryl-substituted (which group is unsubstituted or substituted by one or more of $C_{1-3}$ alkyl, $C_{1-4}$ alkoxy, halo, NO$_2$, OH and NH$_2$) and is otherwise unsubstituted or substituted by one or more substituents selected from halo
(g) when present, R$_{7'}$ represents Het$^c$, aryl, C$_{1-6}$ alkyl, which latter two groups are unsubstituted or substituted by one or more substituents selected from aryl (which group is unsubstituted or substituted by one or more of C$_{1-6}$ alkyl, alkoxy, halo, NO$_2$, OH and NH$_2$), alkoxy halo, OH and NH$_2$;
(h) when present, R$_8$, R$_{11}$, R$_{14}$ and R$_{17}$ each independently represent at each occurrence thereof H, or C$_{1-6}$ alkyl, which latter group is unsubstituted or substituted by one or more substituents selected from halo, alkoxy, OH and NH$_2$;
(i) when present, R$_{12}$, R$_{13}$, R$_{15}$, R$_{16}$, R$_{18}$, and R$_{19}$ each independently represent at each occurrence thereof H, C$_{1-6}$ alkyl, which latter group is unsubstituted or substituted by one or more substituents selected from halo, alkoxy, OH and NH$_2$;
(j) Het$^a$ to Het$^d$ independently represent, at each occurrence, a 5- or 6-membered heteroaromatic group containing one or more heteroatoms selected from 0 and N, which heterocyclic groups are unsubstituted or substituted by one or more substituents selected from =O, halo, OH, C$_{1-4}$ alkyl and C$_{1-4}$ alkoxy, which latter two groups are optionally substituted by one or more substituents selected from halo, OH and NH$_2$;
(k) A represents a 6- to 10-membered aromatic or heterocyclic ring system (e.g. A represents phenyl or pyridyl);
(l) x is from 0 to 2;
(m) x', when present, is 2;
(n) y is from 1 to 3;
(o) z is from 1 to 3.

Yet further embodiments of the invention that may be mentioned include those that relate to compounds of formula I in which:

(i) R$_1$ represents CN or Het$^a$, which latter group is unsubstituted or substituted by halo, or C$_{1-6}$ alkyl, which latter group is unsubstituted or substituted by one or more substituents selected from halo, OH and NH$_2$, optionally wherein R$_1$ represents CN;
(ii) R$_2$ and R$_3$ independently represent H, C(O)R$_7$, S(O)$_x$R$_{7'}$, C$_{1-6}$ alkyl, which latter group is unsubstituted or substituted by one or more substituents selected from halo, OH and NH$_2$;
(iii) when present, each R$_4$ independently represents halo, C$_{1-6}$ alkyl (which latter group is unsubstituted or substituted by one or more substituents selected from halo, OH and NH$_2$), OR$_{11}$, or NR$_{12}$R$_{13}$;
(iv) when present, each R$_5$ independently represents halo, C$_{1-3}$ alkyl (which latter group is unsubstituted or substituted by one or more substituents selected from halo, OH and NH$_2$), or OR$_{14}$;
(v) when present, each R$_6$ independently represents halo, C$_{1-6}$ alkyl (which latter group is unsubstituted or substituted by one or more substituents selected from halo, OH and NH$_2$), OR$_{17}$, or NR$_{18}$R$_{19}$;
(vi) when present, R$_7$ represents Het$^c$, aryl, C$_{1-6}$ alkyl, which latter two groups are unsubstituted or substituted by one or more substituents selected from aryl (which group is unsubstituted or substituted by one or more of C$_{1-6}$ alkyl, alkoxy, halo, NO$_2$, OH and NH$_2$), alkoxy, halo, OH and NH$_2$;
(vii) when present, R$_{7'}$ represents Het$^c$, or aryl, which latter group is unsubstituted or substituted by one or more substituents selected from C$_{1-4}$ alkoxy, halo, OH and NH$_2$;

(viii) when present R$_8$, R$_{11}$, R$_{14}$ and R$_{17}$ each independently represent at each occurrence thereof H, or C$_{1-3}$ alkyl, which latter group is unsubstituted or substituted by one or more substituents selected from halo, C$_4$ alkoxy, OH and NH$_2$;
(ix) when present, R$_{12}$, R$_{13}$, R$_{15}$, R$_{16}$, R$_{18}$, and R$_{19}$ each independently represent at each occurrence thereof H, C$_{1-3}$ alkyl, which latter group is unsubstituted or substituted by one or more substituents selected from halo, C$_{1-4}$ alkoxy, OH and NH$_2$;
(x) Het$^a$ to Het$^d$ independently represent, at each occurrence, a 5- or 6-membered heteroaromatic group containing one or more heteroatoms selected from O and N, which heterocyclic groups are unsubstituted;
(xi) A represents a 6-membered aromatic or heterocyclic ring system (e.g. A represents phenyl or pyridyl);
(xii) x is from 1 to 2;
(xiii) x', when present, is 2;
(xiv) y is from 1 to 2;
(xv) z is from 2 to 3.

For the avoidance of doubt, each of the terms (a) to (o) and (i) to (xv) refer to separate embodiments, which can be mixed and matched together.

In certain embodiments disclosed herein R$_1$ may represent CN and/or R$_2$ and R$_3$ may each represent H.

Embodiments of the invention that may be mentioned include those in which the compound of formula I is a compound selected from the list:

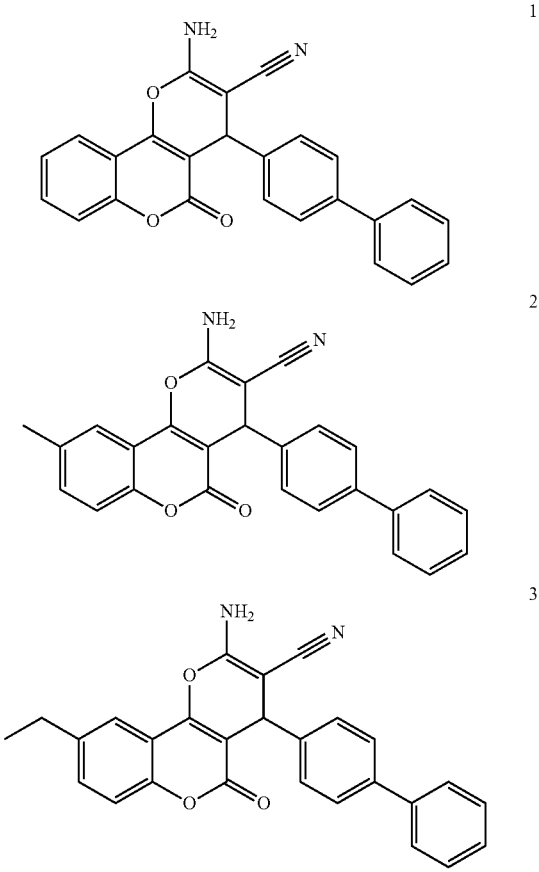

-continued
4
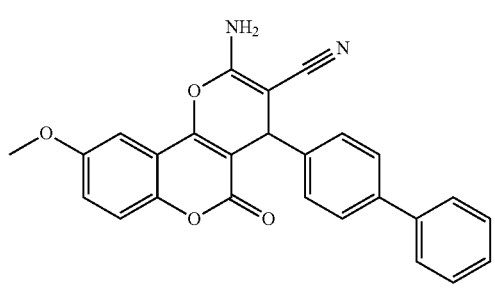
5
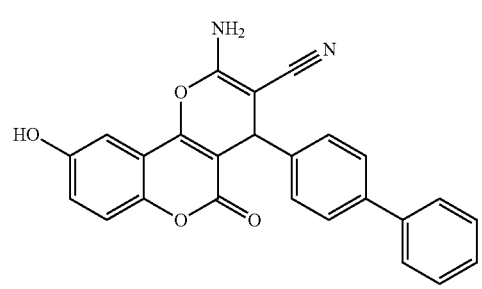
6
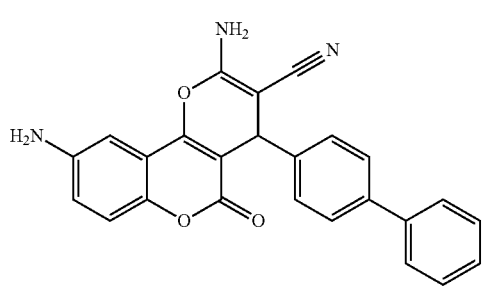
7
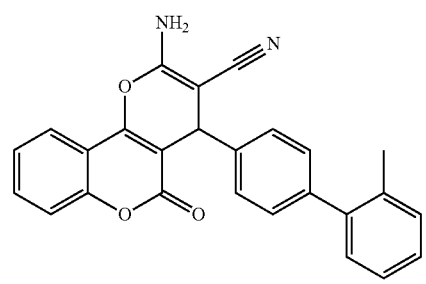
8
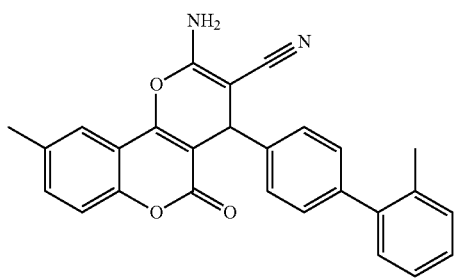
-continued
9
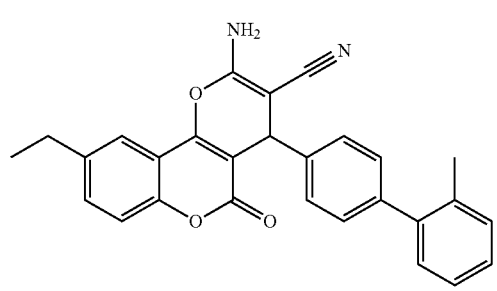
10
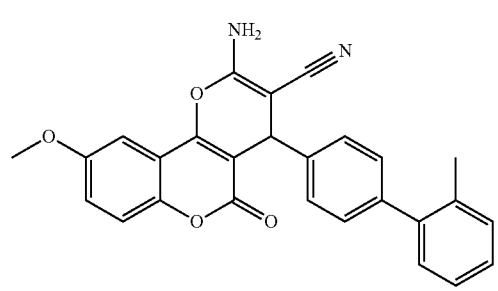
11
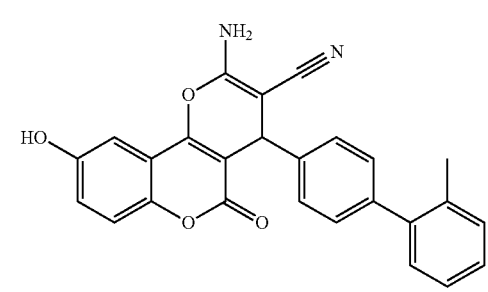
12
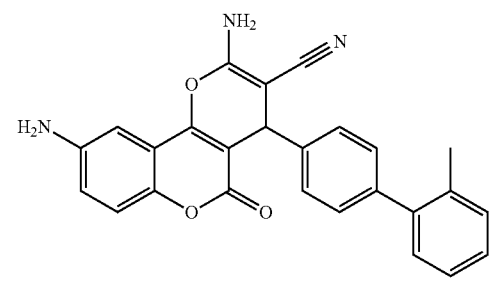
13
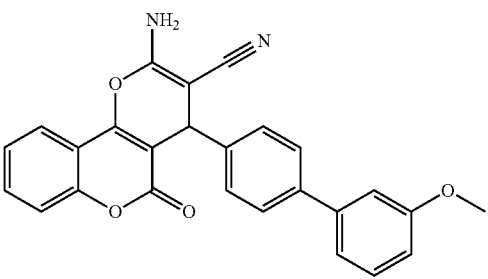

14
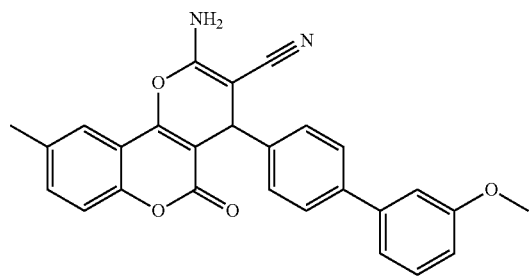
15
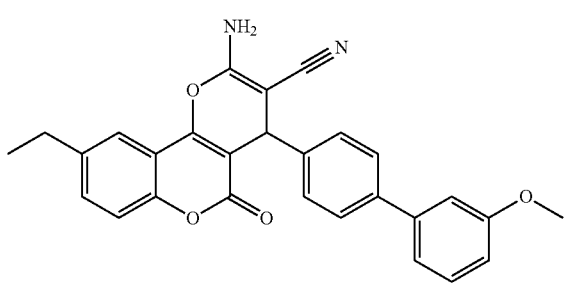
16
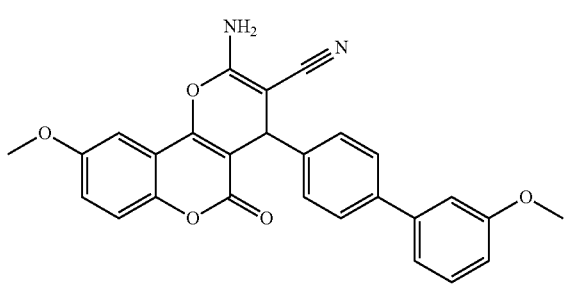
17
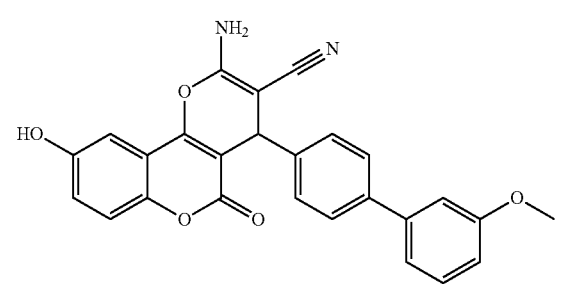
18
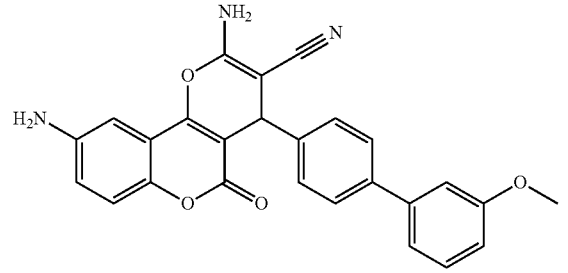
19
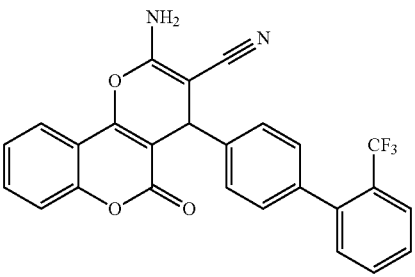
20
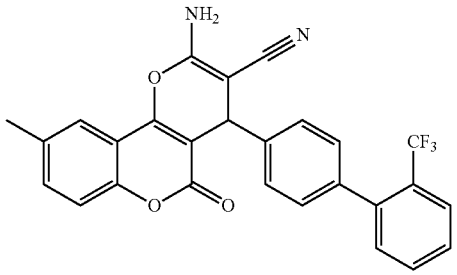
21
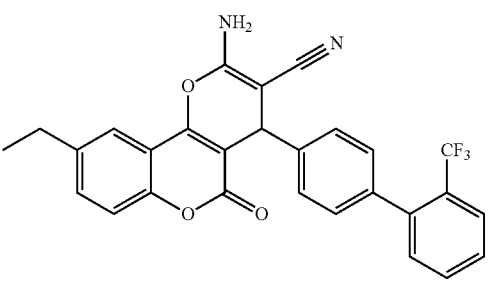
22
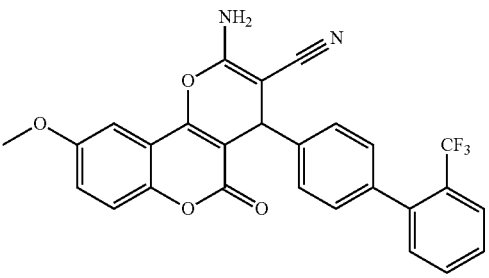
23
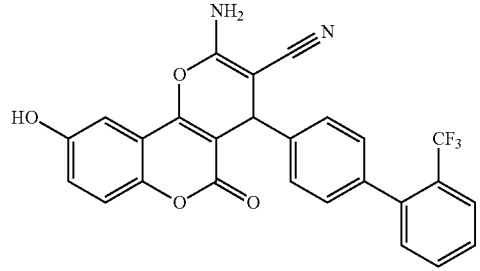

34
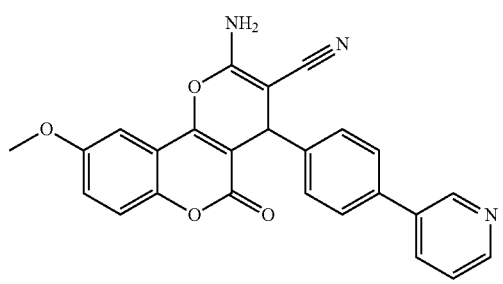
35
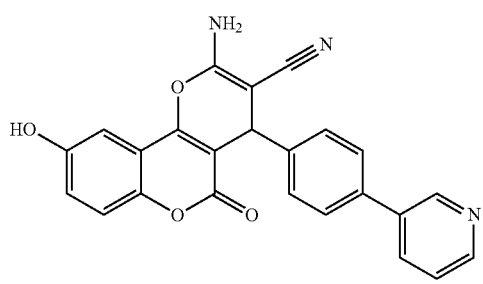
36
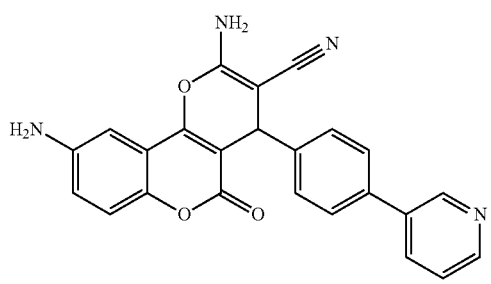
37
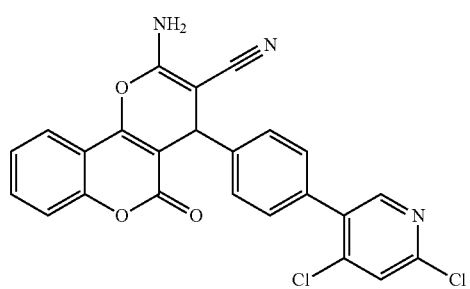
38
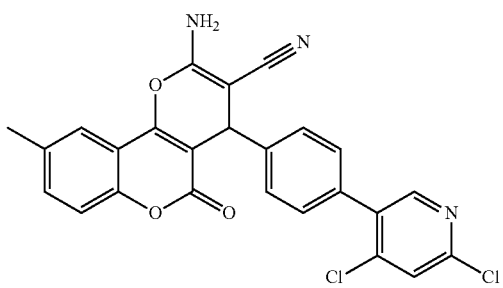
39
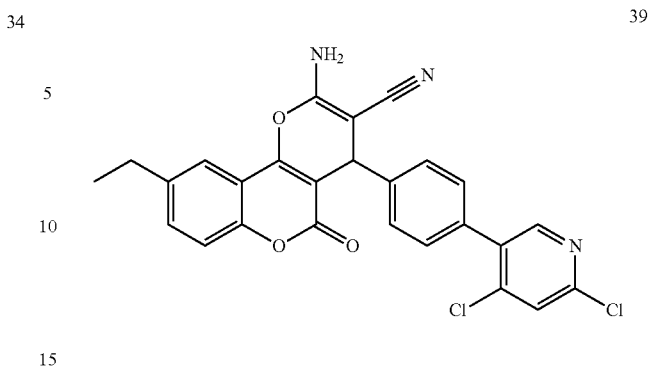
40
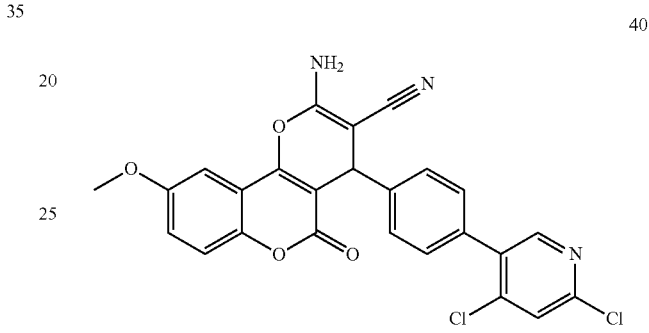
41
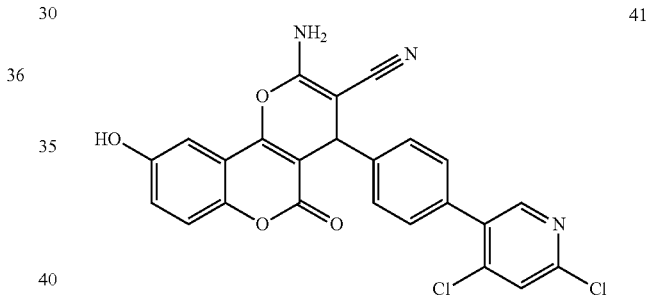
42
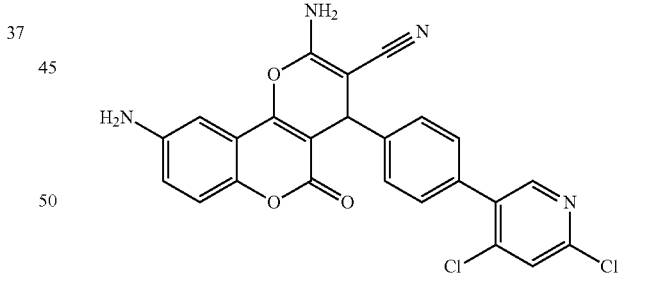
43
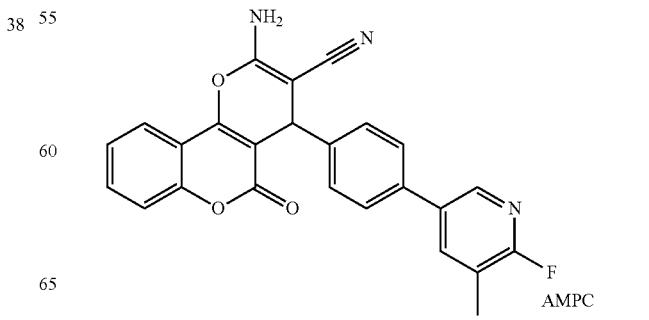
AMPC 44
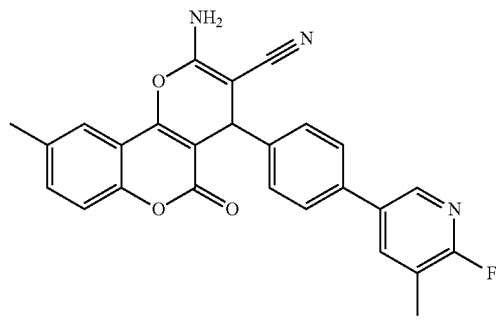
45
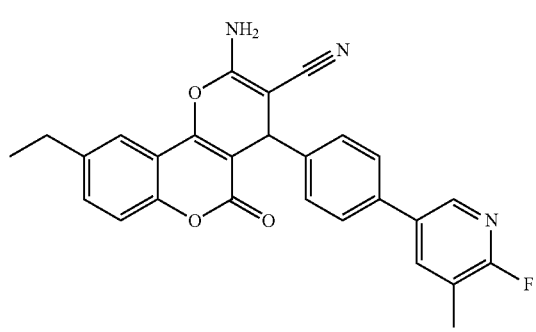
46
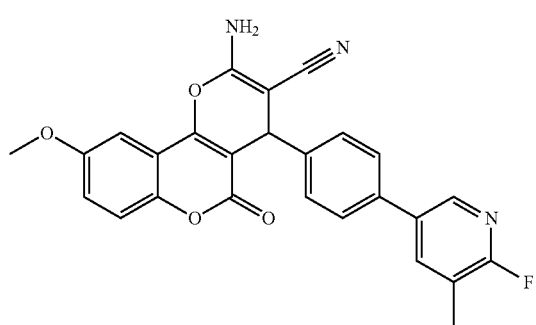
47
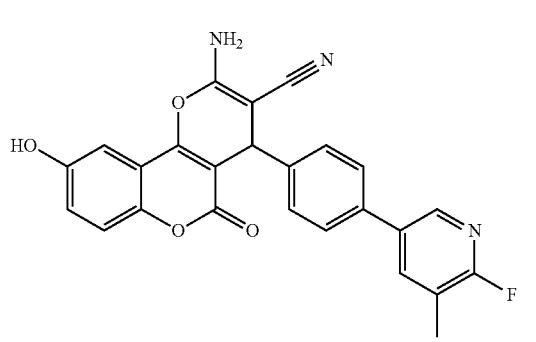
48
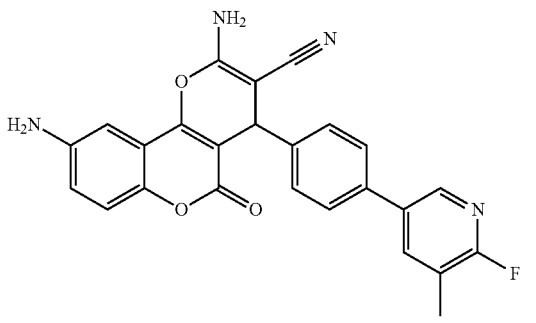
49
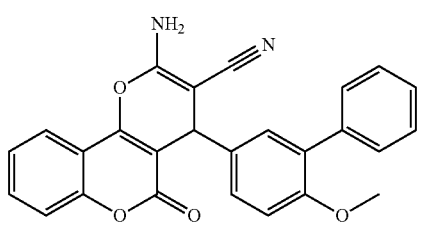
50
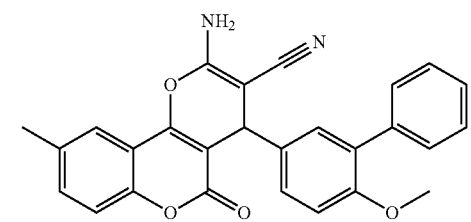
51
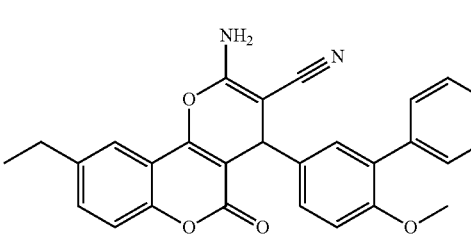
52
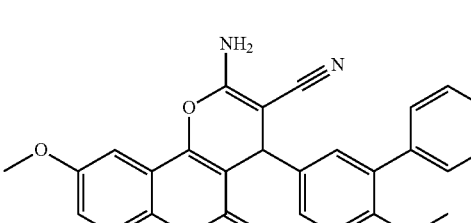
53
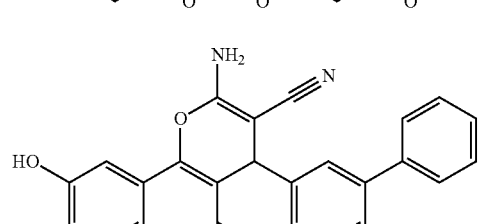
54
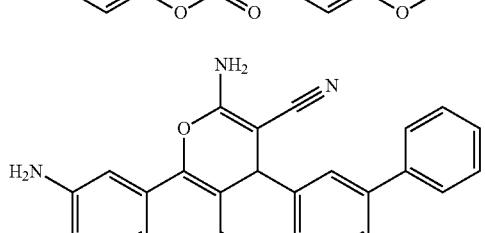
55
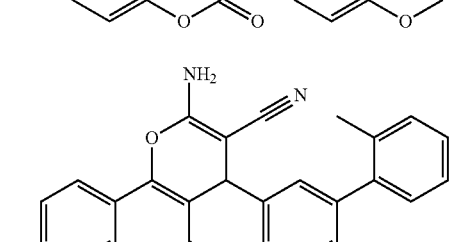

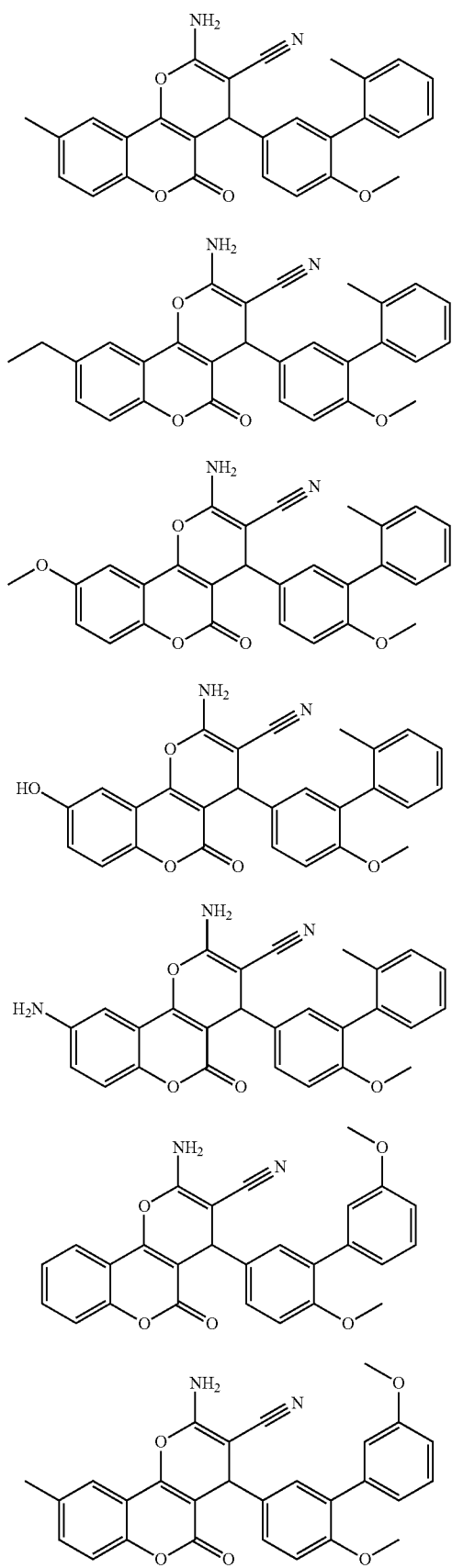
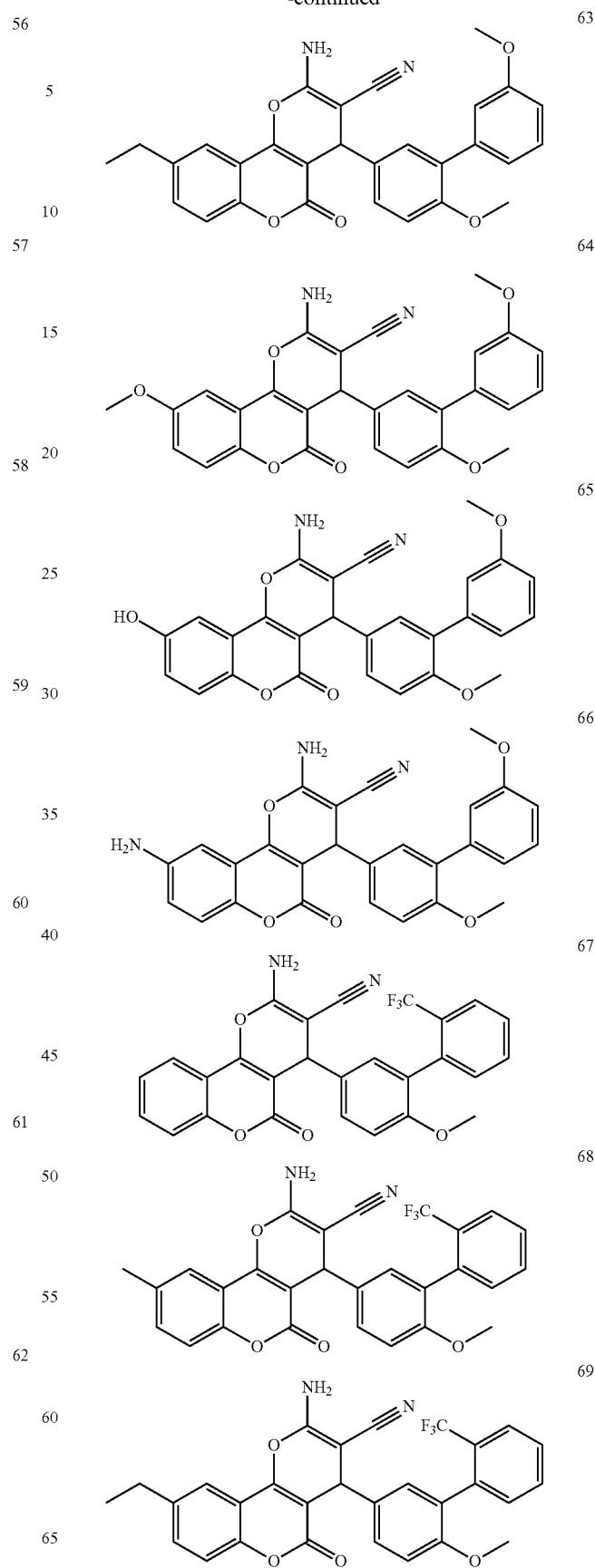

70
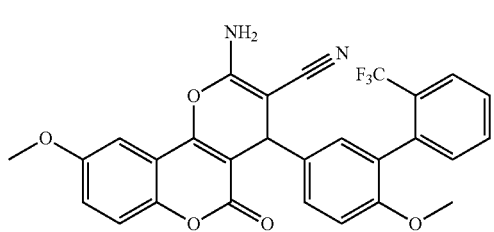
71
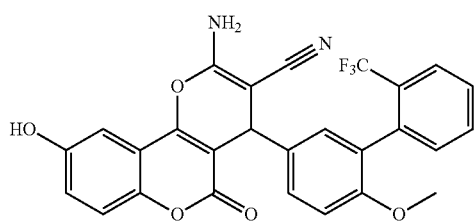
72
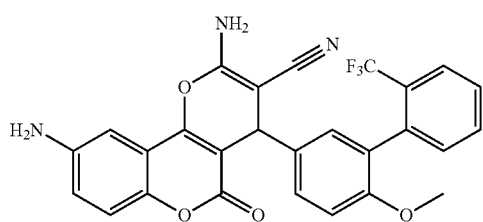
73
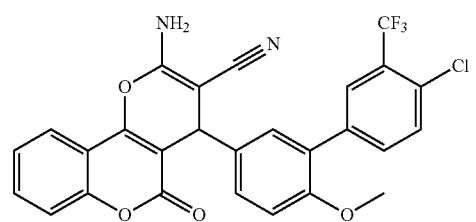
74
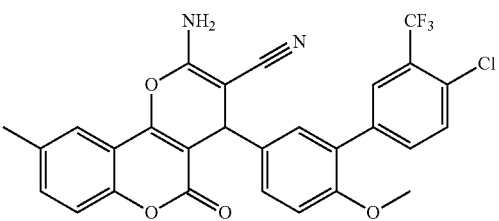
75
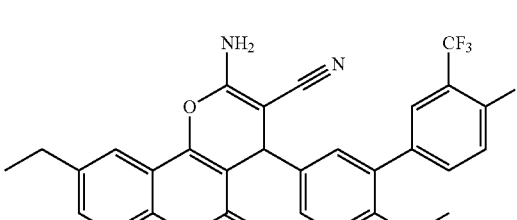
76
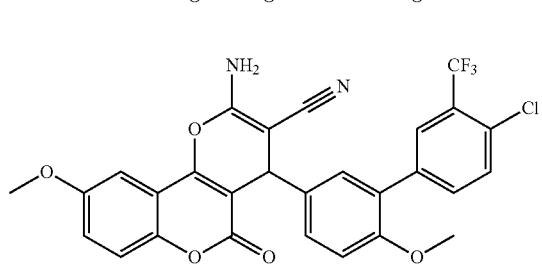
77
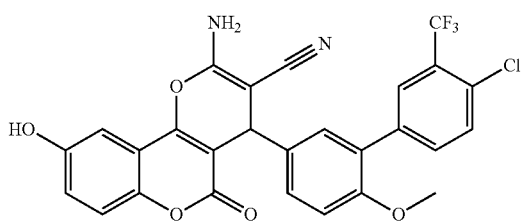
78
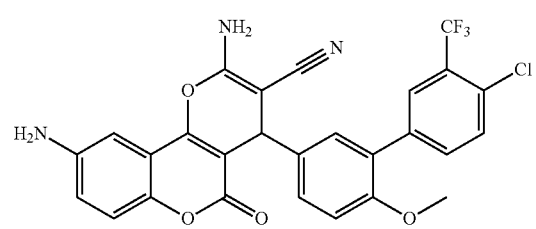
79
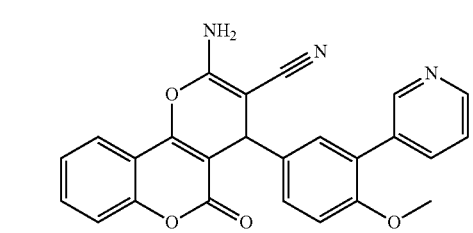
80
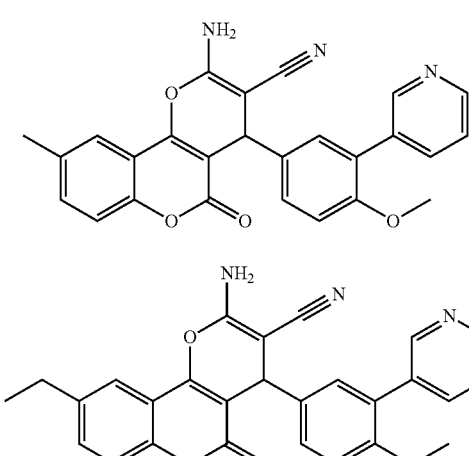
81
82
83
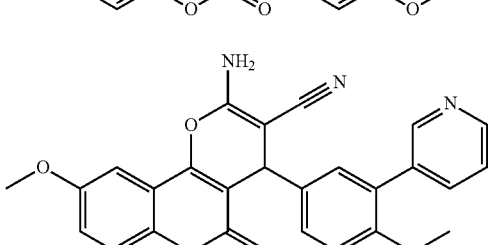
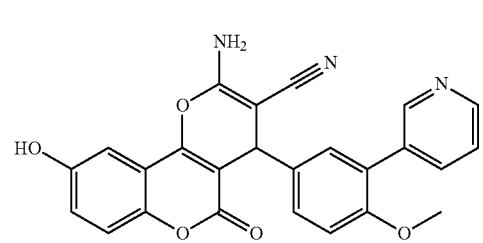

84
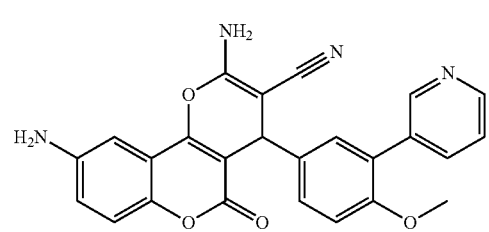
85
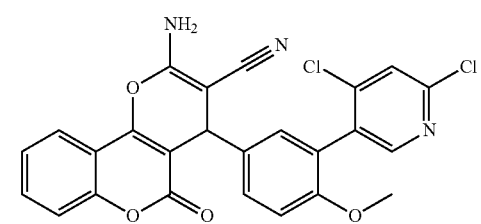
86
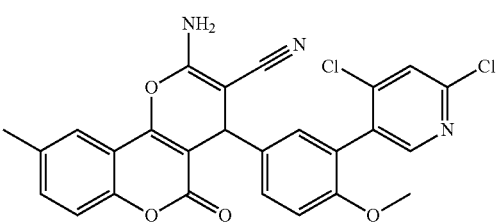
87
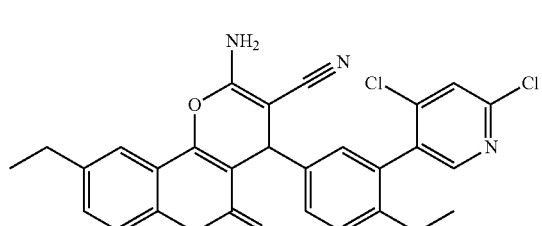
88
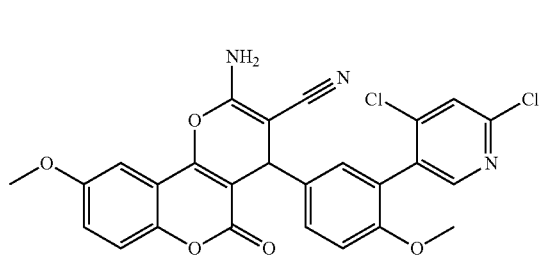
89
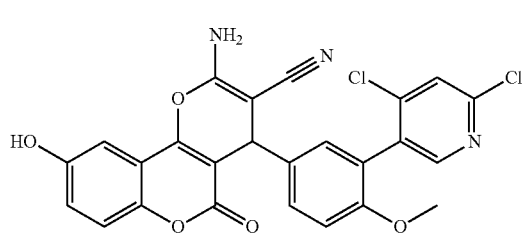
90
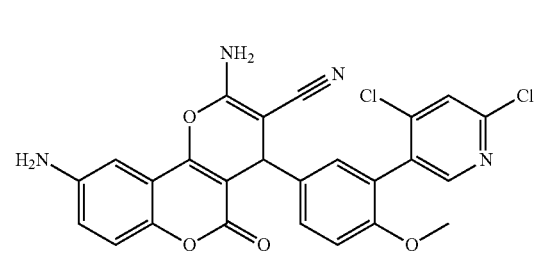
91
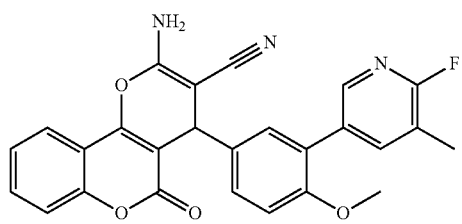
Methoxy-AMPC
92
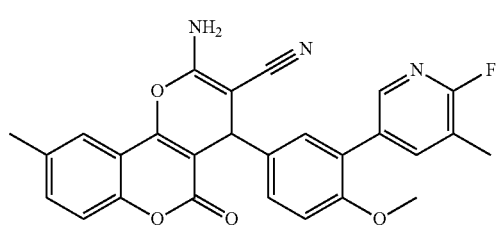
93
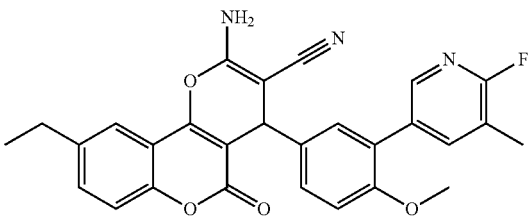
94
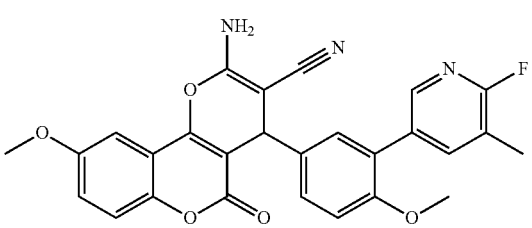
95
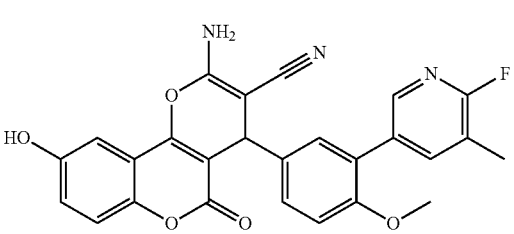
96
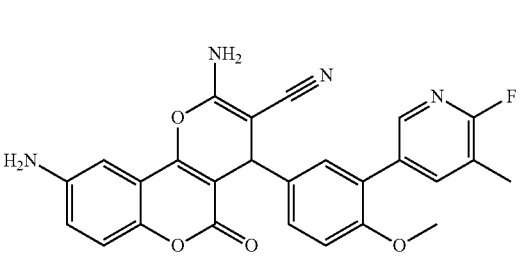

97
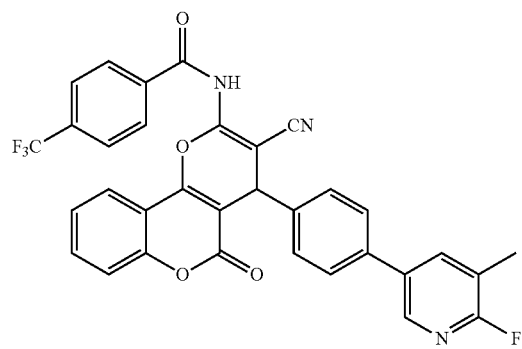
98
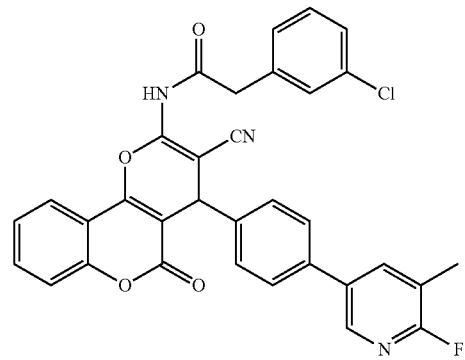
99
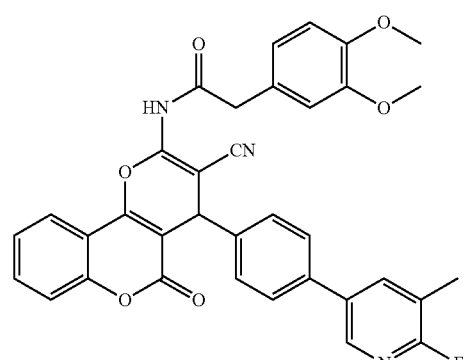
100
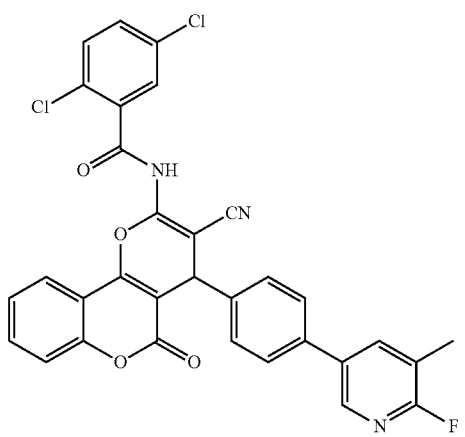
101
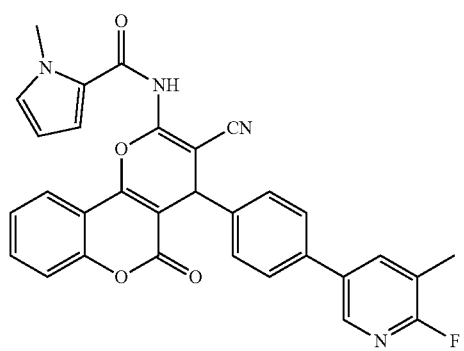
102
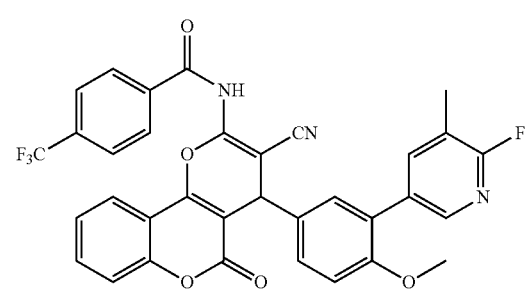
103
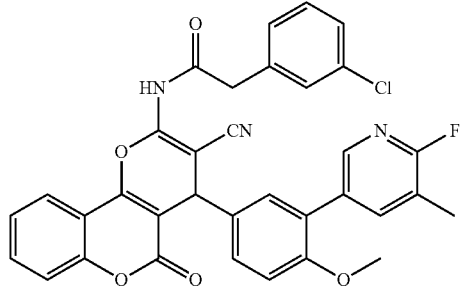
104
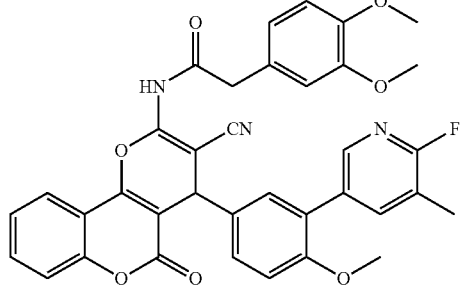
105
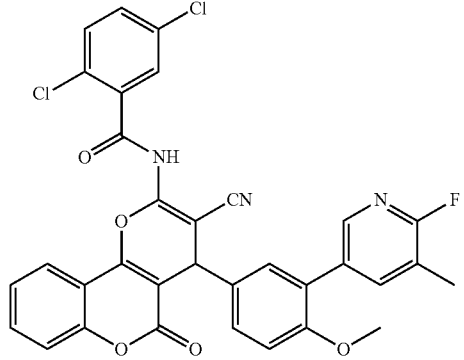

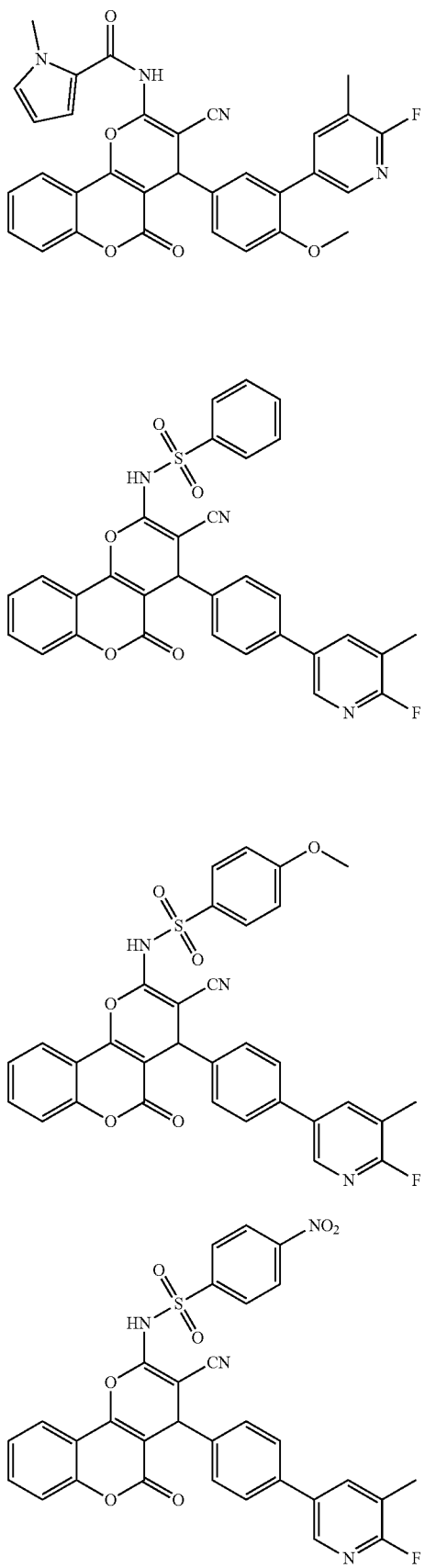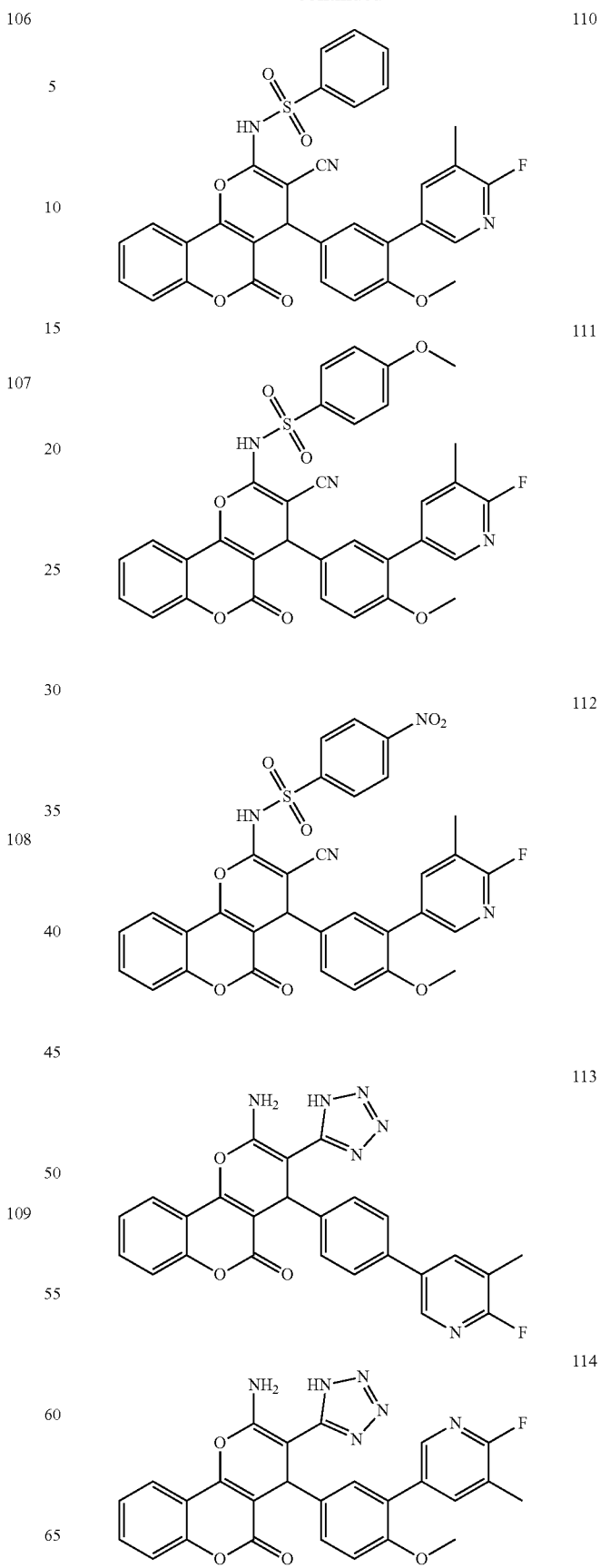

115
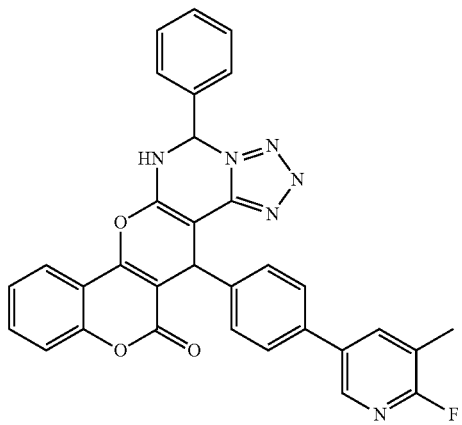
116
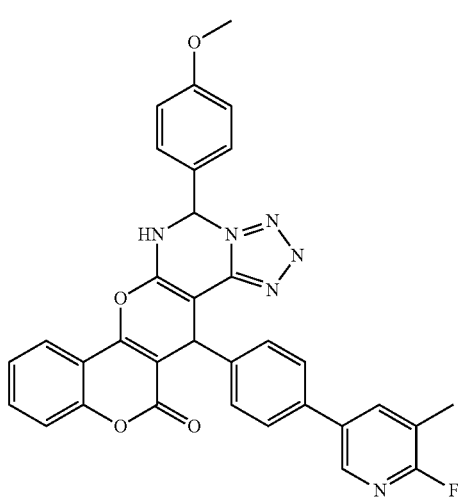
117
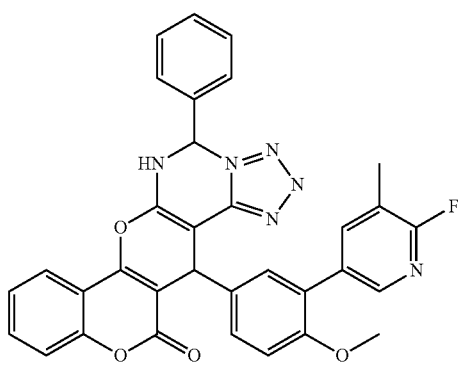
118
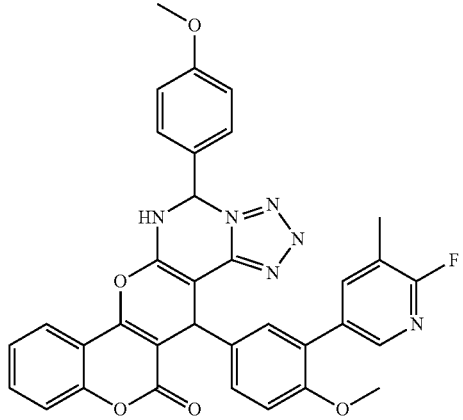
119
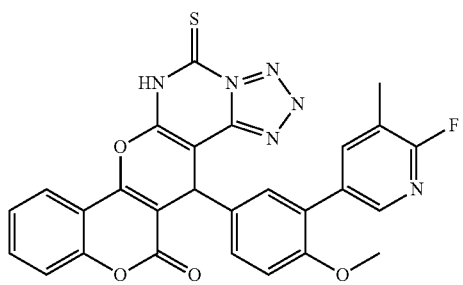
120
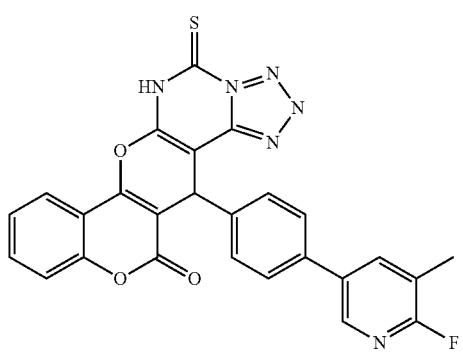
Embodiments of the invention that may be mentioned include those in which the compound of formula I is a compound selected from the list:
1
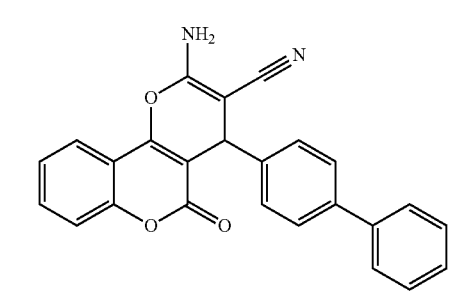

-continued
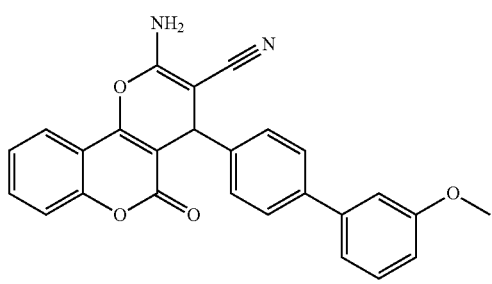
13
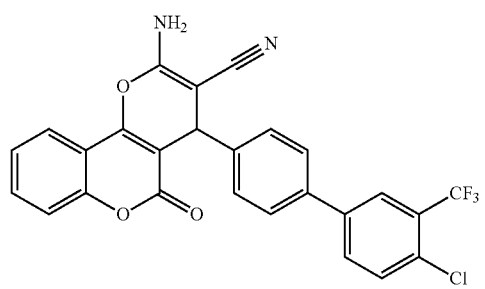
25
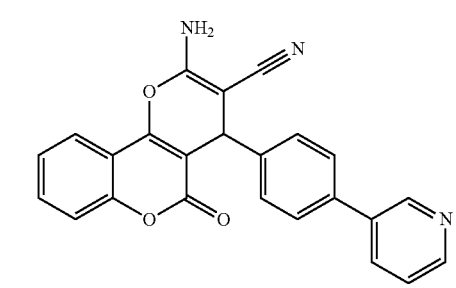
31
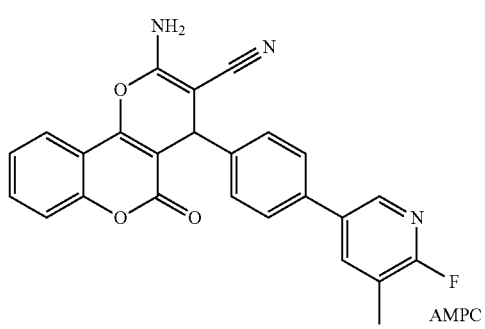
43
AMPC
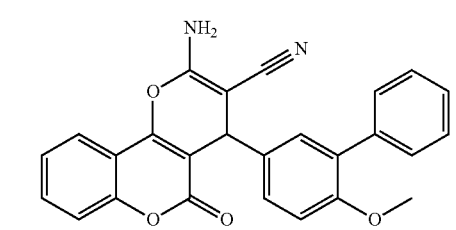
49
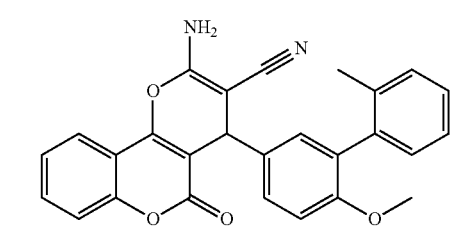
55
-continued
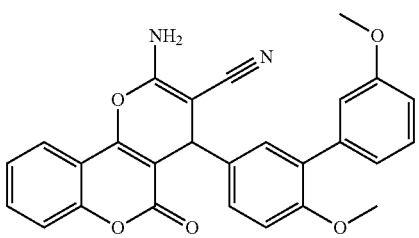
61
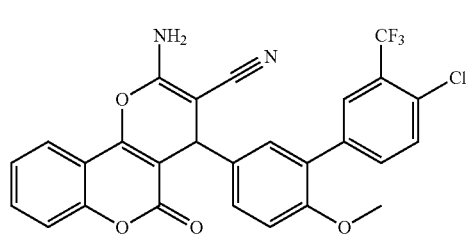
73
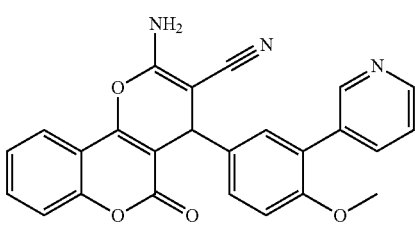
79
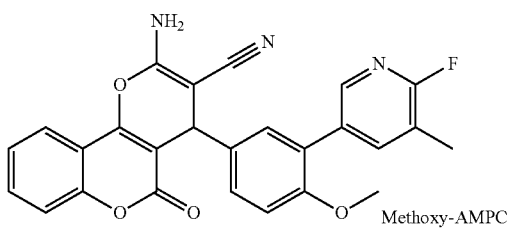
Methoxy-AMPC
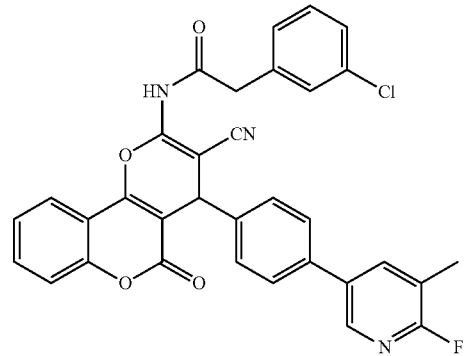
98

99
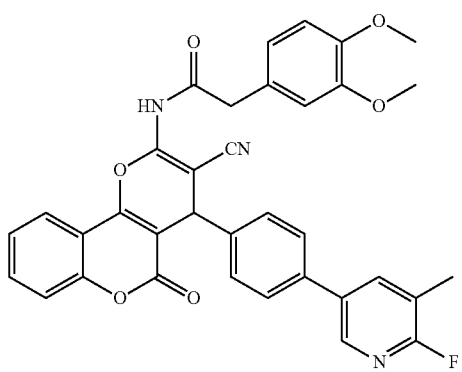
100
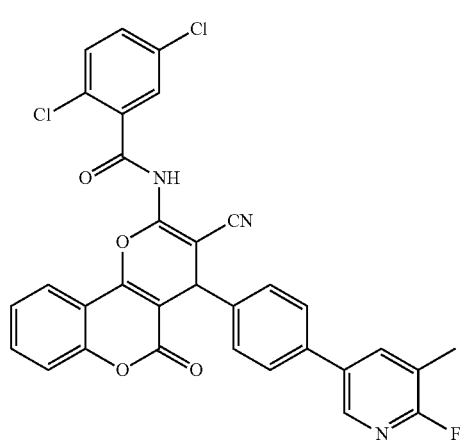
101
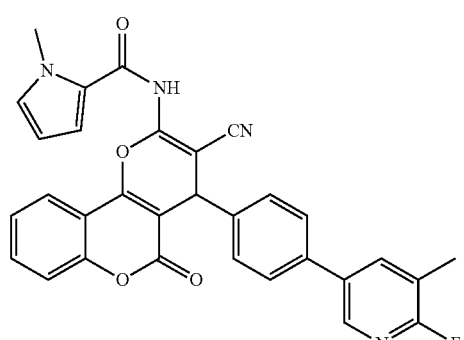
102
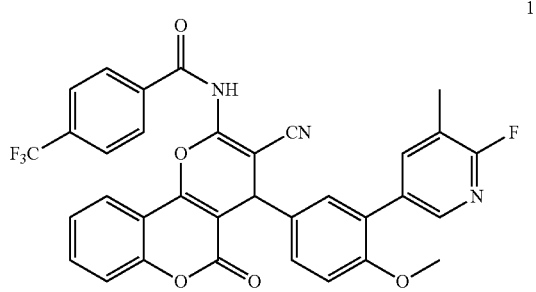
107
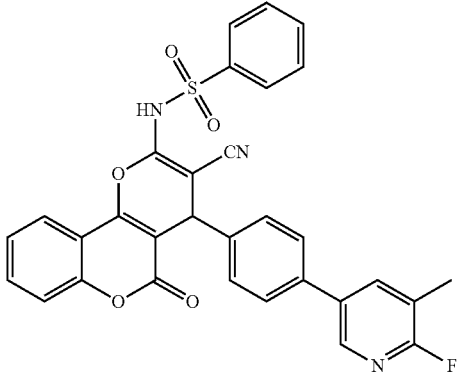
109
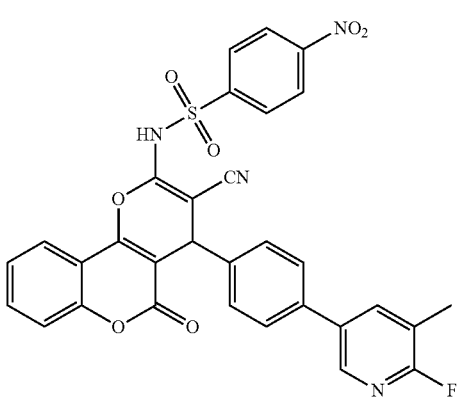
111
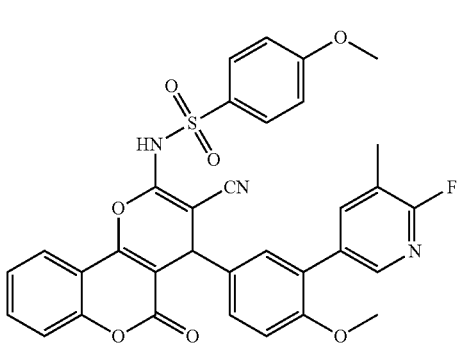
113
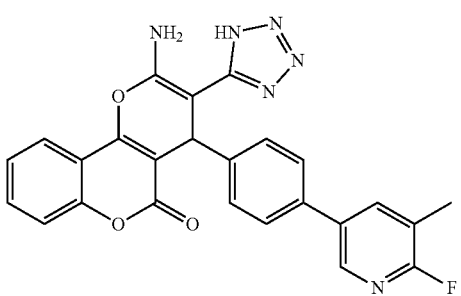
Further embodiments of the invention that may be mentioned include those in which the compound of formula I is a compound selected from the list:

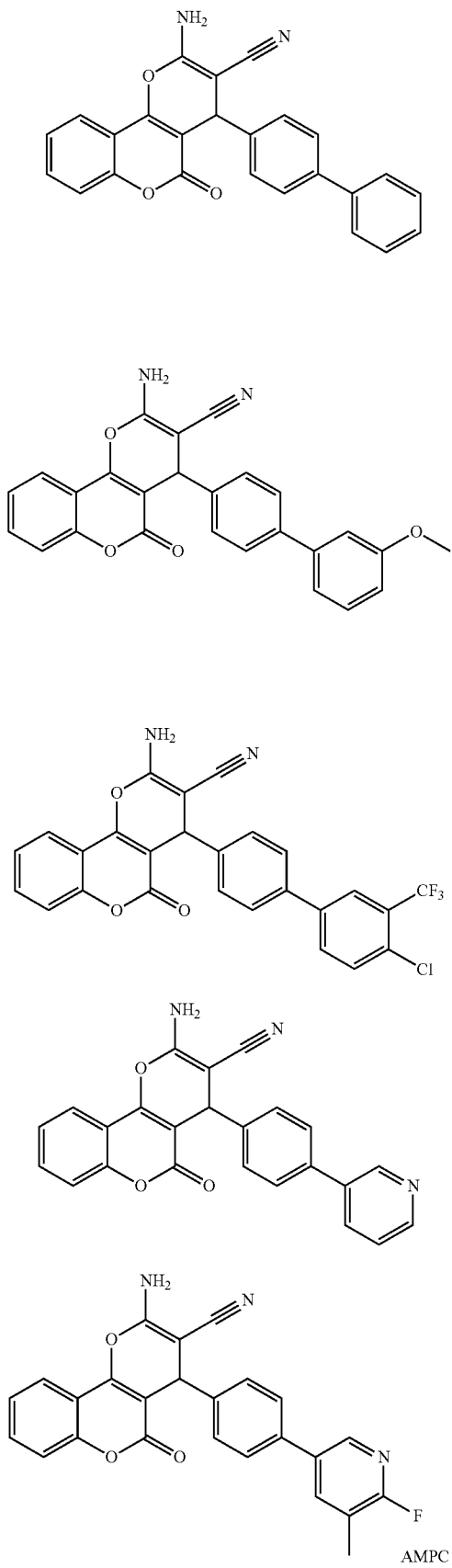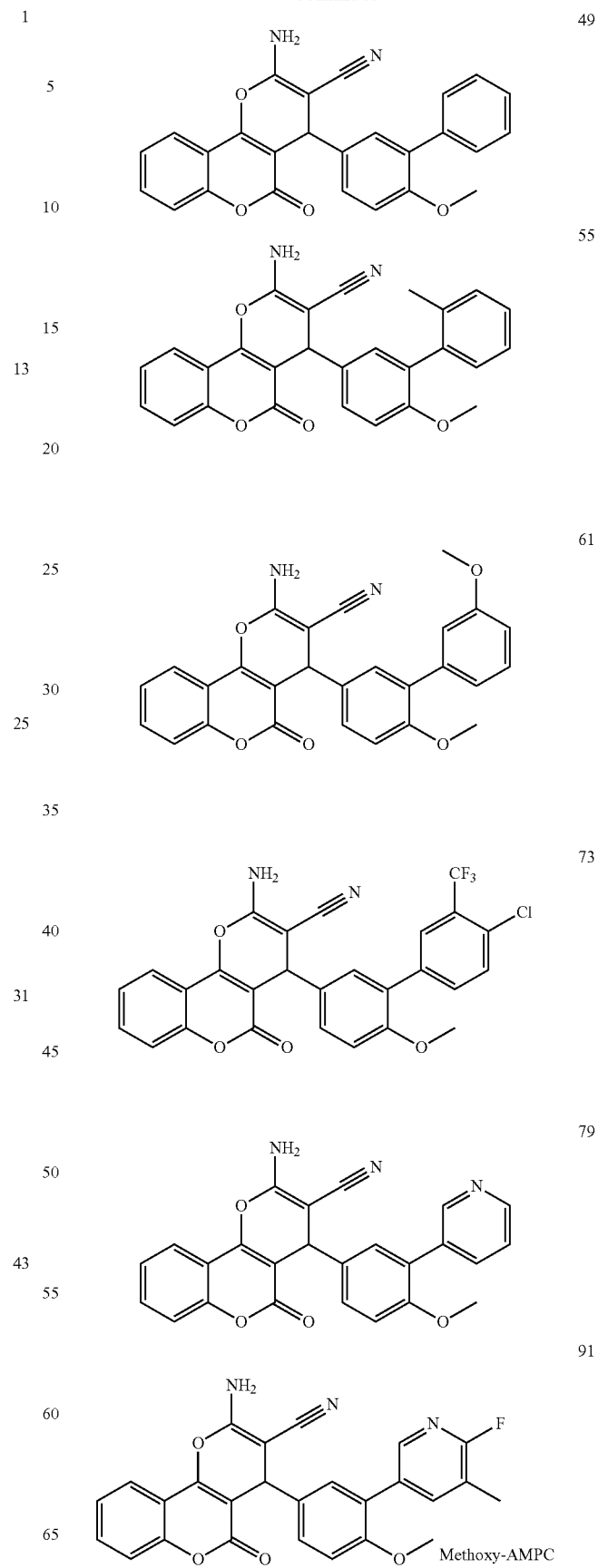

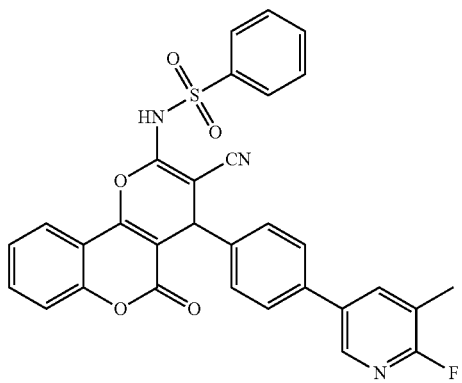

107

Further embodiments of the invention that may be mentioned include those in which the compound of formula I is isotopically labelled. However, other, particular embodiments of the invention that may be mentioned include those in which the compound of formula I is not isotopically labelled.

The term "isotopically labelled", when used herein includes references to compounds of formula I in which there is a non-natural isotope (or a non-natural distribution of isotopes) at one or more positions in the compound. References herein to "one or more positions in the compound" will be understood by those skilled in the art to refer to one or more of the atoms of the compound of formula I. Thus, the term "isotopically labelled" includes references to compounds of formula I that are isotopically enriched at one or more positions in the compound.

The isotopic labelling or enrichment of the compound of formula i may be with a radioactive or non-radioactive isotope of any of hydrogen, carbon, nitrogen, oxygen, sulfur, fluorine, chlorine, bromine and/or iodine. Particular isotopes that may be mentioned in this respect include $^{2}H$, $^{3}H$, $^{11}C$, $^{13}C$, $^{14}C$, $^{13}N$, $^{15}N$, $^{15}O$, $^{17}O$, $^{18}O$, $^{35}S$, $^{18}F$, $^{37}Cl$, $^{77}Br$, $^{82}Br$ and $^{125}I$).

When the compound of formula I is labelled or enriched with a radioactive or nonradioactive isotope, compounds of formula I that may be mentioned include those in which at least one atom in the compound displays an isotopic distribution in which a radioactive or non-radioactive isotope of the atom in question is present in levels at least 10% (e.g. from 10% to 5000%, particularly from 50% to 1000% and more particularly from 100% to 500%) above the natural level of that radioactive or non-radioactive isotope.

Compounds of formula I may be administered by any suitable route, but may particularly be administered orally, intravenously, intramuscularly, cutaneously, subcutaneously, transmucosally (e.g. sublingually or buccally), rectally, transdermally, nasally, pulmonarily (e.g. tracheally or bronchially), topically, by any other parenteral route, in the form of a pharmaceutical preparation comprising the compound in a pharmaceutically acceptable dosage form. Particular modes of administration that may be mentioned include oral, intravenous, cutaneous, subcutaneous, nasal, intramuscular or intraperitoneal administration.

Compounds of formula I will generally be administered as a pharmaceutical formulation in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Suitable pharmaceutical formulations may be found in, for example, Remington The Science and Practice of Pharmacy, 19th ed., Mack Printing Company, Easton, Pa. (1995). For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, Science (1990) 249, 1527.

Otherwise, the preparation of suitable formulations may be achieved routinely by the skilled person using routine techniques and/or in accordance with standard and/or accepted pharmaceutical practice.

The amount of compound of formula I in any pharmaceutical formulation used in accordance with the present invention will depend on various factors, such as the severity of the condition to be treated, the particular patient to be treated, as well as the compound(s) which is/are employed. In any event, the amount of compound of formula I in the formulation may be determined routinely by the skilled person.

For example, a solid oral composition such as a tablet or capsule may contain from 1 to 99% (w/w) active ingredient; from 0 to 99% (w/w) diluent or filler; from 0 to 20% (w/w) of a disintegrant; from 0 to 5% (w/w) of a lubricant; from 0 to 5% (w/w) of a flow aid; from 0 to 50% (w/w) of a granulating agent or binder; from 0 to 5% (w/w) of an antioxidant; and from 0 to 5% (w/w) of a pigment. A controlled release tablet may in addition contain from 0 to 90% (w/w) of a release-controlling polymer.

A parenteral formulation (such as a solution or suspension for injection or a solution for infusion) may contain from 1 to 50% (w/w) active ingredient; and from 50% (w/w) to 99% (w/w) of a liquid or semisolid carrier or vehicle (e.g. a solvent such as water); and 0-20% (w/w) of one or more other excipients such as buffering agents, antioxidants, suspension stabilisers, tonicity adjusting agents and preservatives.

Depending on the disorder, and the patient, to be treated, as well as the route of administration, compounds of formula I may be administered at varying therapeutically effective doses to a patient in need thereof.

However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of formula I.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

In accordance with the invention, compounds of formula I may be administered alone (i.e. as a monotherapy, such as a monotherapy of a condition or disorder ameliorated by inhibition the inhibition of human trefoil factor 3). In alternative embodiments of the invention, however, compounds of formula I may be administered in combination with another therapeutic agent (e.g. another therapeutic agent for the treatment of a condition or disorder ameliorated by inhibition of inhibition of human trefoil factor 3).

Thus further aspects of the invention relate to the following.

(a) A compound of formula I, as hereinbefore defined, and another therapeutic agent for use in the treatment of a condition or disorder ameliorated by the inhibition of inhibition of human trefoil factor 3.

In this aspect of the invention, the compound of formula i, as hereinbefore defined, may be administered sequentially, simultaneously or concomitantly with the other therapeutic agent.

(b) A compound of formula I, as hereinbefore defined, for use in the treatment of a condition or disorder ameliorated by the inhibition of human trefoil factor 3, wherein the compound of formula I is administered sequentially, simultaneously or concomitantly with another therapeutic agent.

(c) Use of a compound of formula I, as hereinbefore defined, and another therapeutic agent for the preparation of a medicament for the treatment of a condition or disorder ameliorated by the inhibition of human trefoil factor 3, wherein the compound of formula I is administered sequentially, simultaneously or concomitantly with the other therapeutic agent.

(d) Use of a compound of formula I, as hereinbefore defined, for the preparation of a medicament for the treatment of a condition or disorder ameliorated by the inhibition of human trefoil factor 3, wherein the medicament is administered in combination with another therapeutic agent.

(e) A method of treatment of a disorder or condition ameliorated by the inhibition of human trefoil factor 3, which method comprises the administration of an effective amount of a compound of formula I, as hereinbefore defined, and another therapeutic agent to a patient in need of such treatment.

(f) A combination product comprising
(A) a compound of formula I, as hereinbefore defined, and
(B) another therapeutic agent,
wherein each of components (A) and (B) is formulated in admixture with a pharmaceutically-acceptable adjuvant, diluent or carrier.

(g) A combination product as defined at (f) above for use in the treatment of a condition or disorder ameliorated by the inhibition of inhibition of human trefoil factor 3.

(h) The use of a combination product as defined at (f) above for the manufacture of a medicament for the treatment of a condition or disorder ameliorated by the inhibition of inhibition of human trefoil factor 3.

(i) A method of treatment of a disorder or condition ameliorated by inhibition of inhibition of human trefoil factor 3, which method comprises the administration of an effective amount of a combination product as defined at (f) above.

When used herein, the term "another therapeutic agent" includes references to one or more (e.g. one) therapeutic agents (e.g. one therapeutic agent) that are known to be useful for (e.g. that are known to be effective in) the treatment of a hyperproliferative condition or disorder as hereinbefore defined.

Examples of suitable therapeutic agents that may be used in combination with the compounds of Formula I include, but are not limited to, taxanes (e.g. paclitaxel, docetaxel, cabazitaxel), vinca alkaloids (e.g. vinblastine, vincristine, vindesine, vinorelbine), colchicine, podophyllotoxin, podophyllin, teniposide, griseofulvin, halichondrin B, eribulin, estramustine, epothilones (e.g. epothilones A-F, ixabepilone, patupilone, sagopilone, BMS-310705, BMS-247550), PI3K inhibitors (e.g. 3-methyladenine, wortmannin, LY294002 (2-(4-Morpholinyl)-8-phenyl-1(4H) benzopyran-4-one)), bafilomycin A1, thapsigargin, lysophosphatidic acid sodium salt, spautin-1, forskolin, nocodazole, L-asparagine, vinblastine, dibutyryl cAMP, hydroxychloroquine, tolazamide, quinine, SP600125 (1,9-pyrazoloanthrone), AICAR (5-aminoimidazole-4-carboxamide 1-β-D-ribofuranoside), anisomycin, SB-216763 (3-(2,4-dichlorophenyl)-4-(1-methyl-1H-indol-3-yl)-1H-pyrrole-2,5-dione), chloroquine, hydroxychloroquine, Lys05, E64d ((2S,3S)-trans-epoxysuccinyl-L-leucylamido-3-methylbutane ethyl ester), leupeptin, pepstatin A, desmethylclomipramine hydrochloride, roliparam, PMSF (phenylmethylsulfonyl fluoride), EHNA (erythro-9-(2-hydroxy-3-nonyl)adenine hydrochloride), pifithrin-μ, clomipramine, cycloheximide, N-acetyl-L-cysteine, GMX1778, p97 inhibitors (e.g. DBeQ (N2,N4-dibenzylquinazoline-2,4-diamine), MDBN (3,4-Methylenedioxy-o-nitrostyrene)) and pharmaceutically acceptable salts or solvates thereof and the like.

When used herein, the term "administered sequentially, simultaneously or concomitantly" includes references to:
administration of separate pharmaceutical formulations (one containing the compound of formula I and one or more others containing the one or more other therapeutic agents); and
administration of a single pharmaceutical formulation containing the compound of formula I and the other therapeutic agent(s).

The combination product described above provides for the administration of component (A) in conjunction with component (B), and may thus be presented either as separate formulations, wherein at least one of those formulations comprises component (A) and at least one comprises component (B), or may be presented (i.e. formulated) as a combined preparation (i.e. presented as a single formulation including component (A) and component (B)).

Thus, there is further provided:
(I) a pharmaceutical formulation including a compound of formula I, as hereinbefore defined and another therapeutic agent, in admixture with a pharmaceutically-acceptable adjuvant, diluent or carrier (which formulation is hereinafter referred to as a "combined preparation"); and
(II) a kit of parts comprising components:
(i) a pharmaceutical formulation including a compound of formula I, as hereinbefore defined, in admixture with a pharmaceutically-acceptable adjuvant, diluent or carrier; and
(ii) a pharmaceutical formulation including another therapeutic agent, in admixture with a pharmaceutically-acceptable adjuvant, diluent or carrier, which components (i) and (ii) are each provided in a form that is suitable for administration in conjunction with the other.

Component (i) of the kit of parts is thus component (A) in admixture with a pharmaceutically-acceptable adjuvant, diluent or carrier. Similarly, component (ii) is component (B) in admixture with a pharmaceutically-acceptable adjuvant, diluent or carrier.

The aspects of the invention described herein (e.g. the above-mentioned compounds, combinations, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, or may have other useful pharmacological properties over, similar compounds, combinations, methods (treatments) or uses known in the prior art for use in the treatment of those conditions or otherwise.

Intermediates used to manufacture the Compounds of formula I may be known and/or may be commercially available. Intermediates used to manufacture compounds of formula I (e.g. that are not commercially available) may be prepared in accordance with techniques that are well known to those skilled in the art, for example as described hereinafter (e.g. where reference is made to relevant journal articles).

Compounds of the invention may be isolated from their reaction mixtures using conventional techniques (e.g. recrystallisation, column chromatography, preparative HPLC, etc.).

In the processes described above and hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "Protective Groups in Organic Chemistry", edited by J W F McOmie, Plenum Press (1973), and "Protective Groups in Organic Synthesis", 3$^{rd}$ edition, T. W. Greene & P. G. M. Wutz, Wiley-Interscience (1999).

As used herein, the term "functional groups" means, in the case of unprotected functional groups, hydroxy-, thiolo-, aminofunction, carboxylic acid and, in the case of protected functional groups, lower alkoxy, N-, O-, S-acetyl, carboxylic acid ester.

Non-limiting examples which embody certain aspects of the invention will now be described.

EXAMPLES

Materials Employed to Arrive at the Biological Examples of the Present Disclosure Cell Culture and Reagents The human immortalized mammary epithelial cell lines, MCF10A, and MCF12A; and immortalized hepatocellular epithelial cell line, LO2 were obtained from the American Type Culture Collection (ATCC, Rockville, Md.) and were cultured as per ATCC propagation instructions. MC cell lines, MCF7, T47D, BT474, BT20, MDA-MB-361, MDA-MB-436, MDA-MB-468, and MDA-MB-231; endometrial carcinoma cell lines, Ishikawa, ECC1, RL95-2 and AN3; hepatocellular carcinoma cell lines, Hep3B, H2P, and H2M; colon carcinoma cell lines, DLD-1, and Caco-2; and prostate carcinoma cell lines, PC3, LNCaP, and DU145 were obtained from the American Type Culture Collection (ATCC, Rockville, Md.). Pancreatic carcinoma cell lines, AsPC-1 and BxPC-3; Lung carcinoma cell lines, HCC-827, NCI-H1975, HCC-4006, PC-14, and NCI-H1299; and Thyroid carcinoma cell lines HTH83, CAL62, T238, and OGK-M were obtained from Prof. H. Phillip Koeffler's laboratory at The Cancer Science Institute of Singapore, National University of Singapore (NUS). Gastric carcinoma cell lines, AGS, MKN-28, MKN-45, and A2-528 were obtained from Prof. Yoshiaki Ito's laboratory at The Cancer Science Institute of Singapore, NUS. All cell lines were cultured as per ATCC propagation instructions.

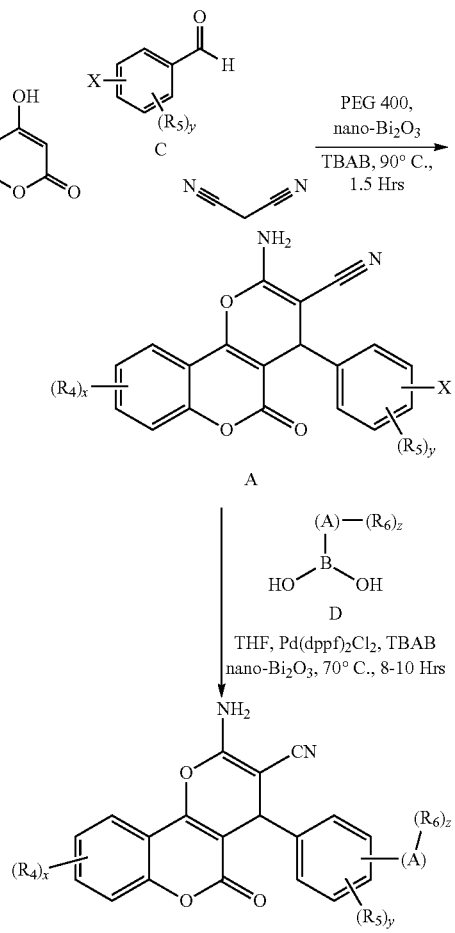

Synthetic Scheme 1

Scheme 1: Compounds of Formula E were obtained from the Suzuki coupling reactions of compounds of Formula A with boronic acids of Formula D. X represents Br, I and Cl; $R_4$, $R_5$, $R_6$, (A), x, y and z correspond to the groups mentioned in the compound of Formula (I) as disclosed hereinbefore.

General Synthetic Protocol 1

Synthetic Procedure for Preparation of Compounds of Formula A

Compounds of Formula A were obtained from a 4-component reaction which involves a Knoevenagel condensation followed by cyclization. This method utilizes a substituted 4-hydroxychroman-2-one (compounds of Formula B), malanonitrile and a substituted aryl/heterocyclic aldehyde (compounds of Formula C) to form the Compounds of Formula A (step 1, Scheme 1).

Aryl/heterocyclic aldehydes of Formula C (1.0 equivalent) were first reacted with malanonitrilein (1.2 equivalent) the presence of PEG-400 solvent (3 volumes), nano-Bi2O3 (1.0 equivalent) and catalytic amount of tetrabutyl ammonium bromide (TBAB) as mild base catalyst at 90° C. for 20 min. to obtain a Knoevenagel condensed product. Substituted 4-hydroxychroman-2-ones of Formula B were added to the Knoevenagel condensed product in the same reaction mixture and heating was continued for one hour to form the desired compound, which was confirmed by TLC using hexane-ethylacetate (7:3) eluent system. The reaction mixture was then treated with distilled water (15 mL) to dissolve PEG-400 and filtered. The product in the filtrate was extracted into dichloromethane using a separating funnel. The dichloromethane layer was vacuum evaporated to provide crude compound A, which was further purified by column chromatography using hexane:ethyl acetate eluent system to obtain compound A.

Compounds of Formula A that were synthesised (and their respective starting materials) are detailed below in Table 1.

TABLE 1

| 4-hydroxychroman-2-one (B) | aryl/heterocyclic aldehydes (C) | Compounds of Formula A |
|---|---|---|

TABLE 1-continued

| 4-hydroxychroman-2-one (B) | aryl/heterocyclic aldehydes (C) | Compounds of Formula A |
|---|---|---|
| 6-hydroxy-4-hydroxycoumarin | 4-bromobenzaldehyde | A5 |
| 6-amino-4-hydroxycoumarin | 4-bromobenzaldehyde | A6 |
| 4-hydroxycoumarin | 3-bromo-4-methoxybenzaldehyde | A7 |
| 6-methyl-4-hydroxycoumarin | 3-bromo-4-methoxybenzaldehyde | A8 |
| 6-ethyl-4-hydroxycoumarin | 3-bromo-4-methoxybenzaldehyde | A9 |
| 6-methoxy-4-hydroxycoumarin | 3-bromo-4-methoxybenzaldehyde | A10 |

TABLE 1-continued

| 4-hydroxychroman-2-one (B) | aryl/heterocyclic aldehydes (C) | Compounds of Formula A |
|---|---|---|
| 6-hydroxy-4-hydroxycoumarin (HO- on benzene ring) | 3-bromo-4-methoxybenzaldehyde | A11 |
| 6-amino-4-hydroxycoumarin (H₂N- on benzene ring) | 3-bromo-4-methoxybenzaldehyde | A12 |

General Synthetic Protocol 2

Synthetic Procedure to Provide Compounds of Formula E (Subset of Compounds of Formula (I))

Compounds of Formula E were obtained by Suzuki coupling of the Compounds of Formula A with a variety of substituted aryl/heterocyclic boronic acids (Compounds of Formula D) in tetrahydrofuran solvent, Pd(dppf)$_2$Cl$_2$ catalyst, TBAB and nano-Bi$_2$O$_3$ (Step 2 in Scheme 1 above). This reaction was effected by charging a reaction flask with an arylbromide Compound of Formula A (1 eq), which was then heated to 70° C. with a variety of aryl/hetero boronic acids (1.2 eq; Compounds of Formula D) in the presence of Pd(dppf)$_2$Cl$_2$ as catalyst (0.001 eq) and nano-Bi$_2$O$_3$ (0.5 eq) as base, in 1 ml water and 4 ml tetrahydrofuran as solvent for 8-10 hours to obtain the crude product. The crude product was then purified by column chromatography using hexane:ethyl acetate as the eluent (the ratio of hexane and ethyl acetate was varied depending on the compound in question).

Example 1: Compounds 1-96

Compounds 1-96 were prepared following General Synthetic Protocol 2 above. The compounds made, and their starting materials, are outlined in Table 2 below.

TABLE 2

| Aryl bromide compound (A) | Boronic Acid (D) | Compounds 1-96 (Compounds of Formula E/ Formula (I)) |
|---|---|---|
| A1 | 2a (phenylboronic acid) | 1 |

TABLE 2-continued

| Aryl bromide compound (A) | Boronic Acid (D) | Compounds 1-96 (Compounds of Formula E/ Formula (I)) |
|---|---|---|
| A2 | 2a | 2 |
| A3 | 2a | 3 |
| A4 | 2a | 4 |
| A5 | 2a | 5 |
| A6 | 2a | 6 |

TABLE 2-continued

| Aryl bromide compound (A) | Boronic Acid (D) | Compounds 1-96 (Compounds of Formula E/ Formula (I)) |
|---|---|---|
| A1 | 2b (2-methylphenyl B(OH)₂) | 7 |
| A2 | 2b | 8 |
| A3 | 2b | 9 |
| A4 | 2b | 10 |

TABLE 2-continued
| Aryl bromide compound (A) | Boronic Acid (D) | Compounds 1-96 (Compounds of Formula E/ Formula (I)) |
|---|---|---|
| A5 | 2b | 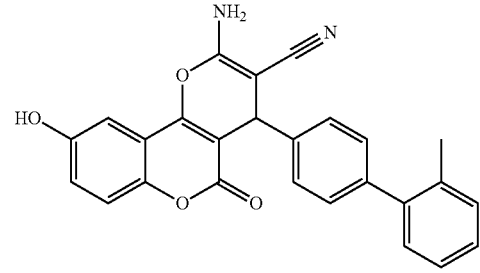<br>11 |
| A6 | 2b | 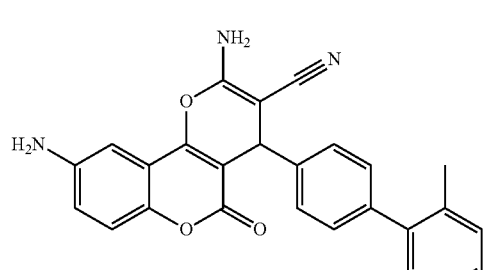<br>12 |
| A1 | 2c | 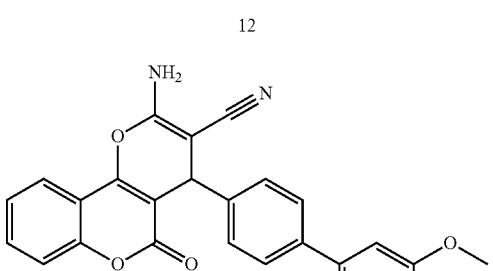<br>13 |
| A2 | 2c | 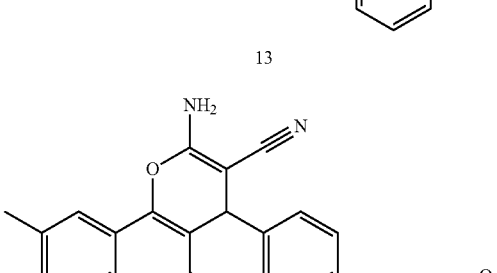<br>14 |
| A3 | 2c | 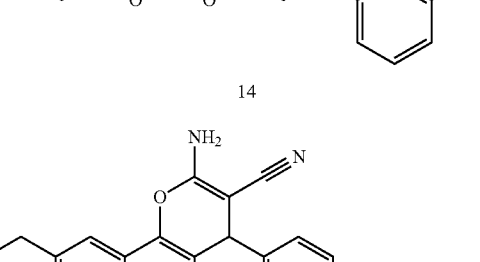<br>15 |

TABLE 2-continued
| Aryl bromide compound (A) | Boronic Acid (D) | Compounds 1-96 (Compounds of Formula E/ Formula (I)) |
|---|---|---|
| A4 | 2c | 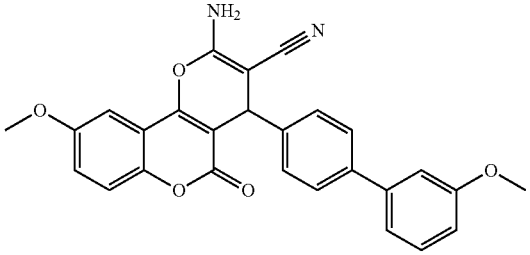<br>16 |
| A5 | 2c | 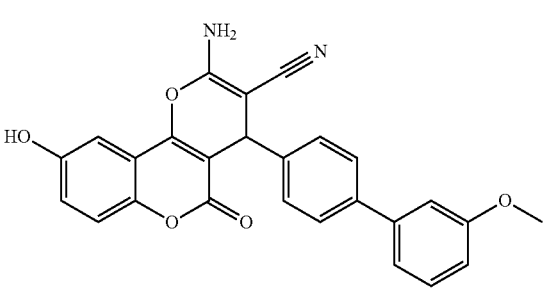<br>17 |
| A6 | 2c | 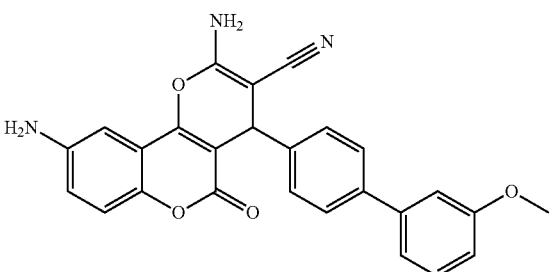<br>18 |
| A1 | 2d | 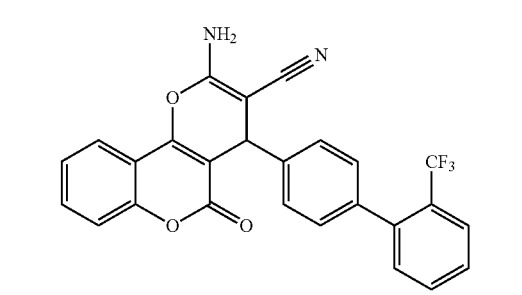<br>19 |
| A2 | 2d | 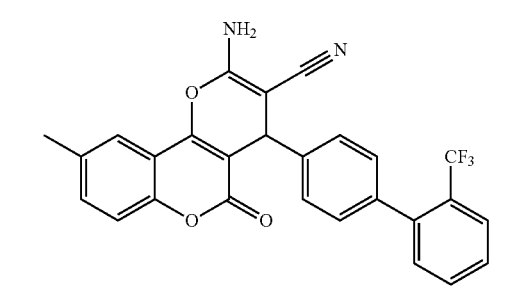<br>20 |

TABLE 2-continued
| Aryl bromide compound (A) | Boronic Acid (D) | Compounds 1-96 (Compounds of Formula E/ Formula (I)) |
|---|---|---|
| A3 | 2d | 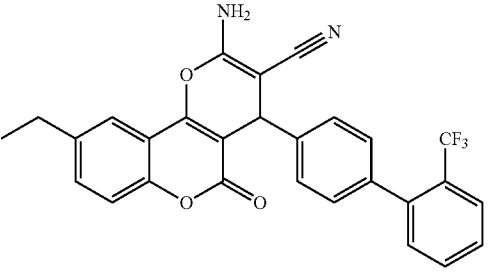<br>21 |
| A4 | 2d | 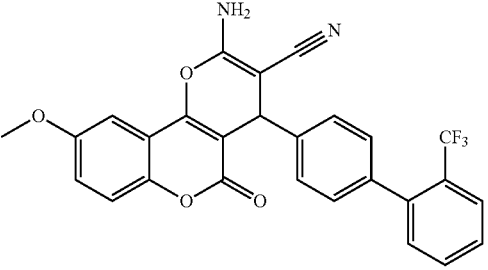<br>22 |
| A5 | 2d | 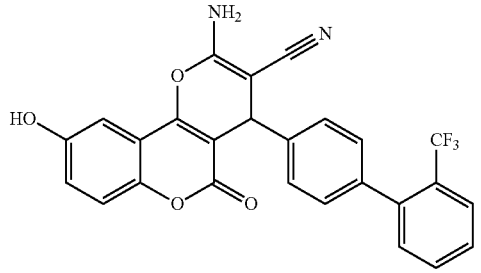<br>23 |
| A6 | 2d | 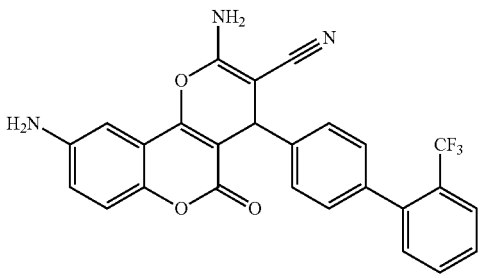<br>24 |
| A1 | 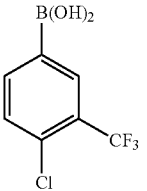<br>2e | 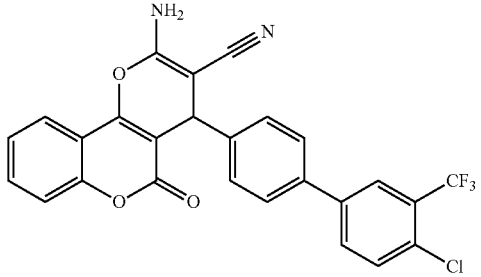<br>25 |

TABLE 2-continued
| Aryl bromide compound (A) | Boronic Acid (D) | Compounds 1-96 (Compounds of Formula E/ Formula (I)) |
|---|---|---|
| A2 | 2e | 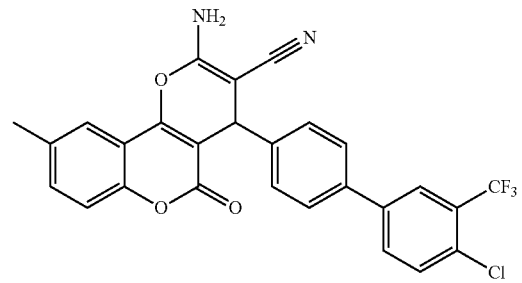<br>26 |
| A3 | 2e | 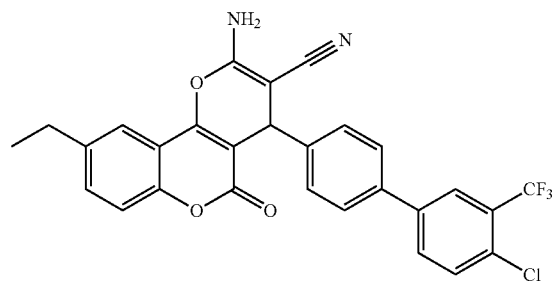<br>27 |
| A4 | 2e | 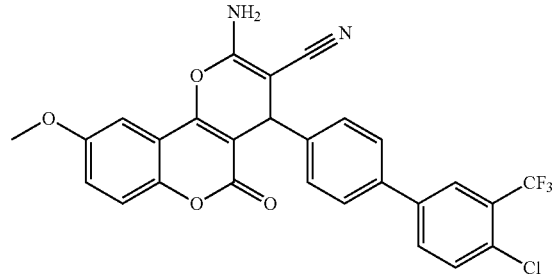<br>28 |
| A5 | 2e | 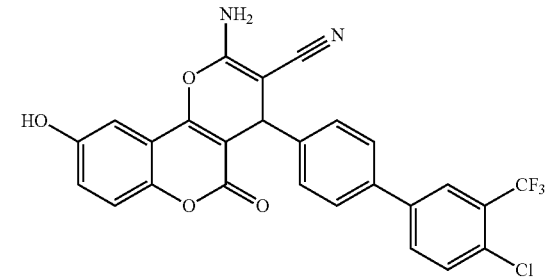<br>29 |

TABLE 2-continued

| Aryl bromide compound (A) | Boronic Acid (D) | Compounds 1-96 (Compounds of Formula E/ Formula (I)) |
|---|---|---|
| A6 | 2e | 30 |
| A1 | 2f | 31 |
| A2 | 2f | 32 |
| A3 | 2f | 33 |

TABLE 2-continued
| Aryl bromide compound (A) | Boronic Acid (D) | Compounds 1-96 (Compounds of Formula E/ Formula (I)) |
|---|---|---|
| A4 | 2f | 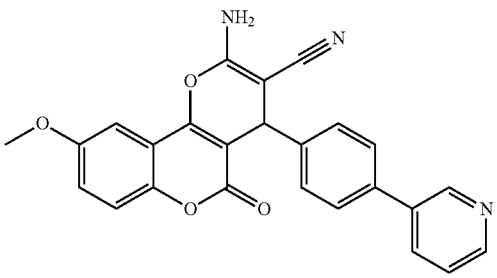<br>34 |
| A5 | 2f | 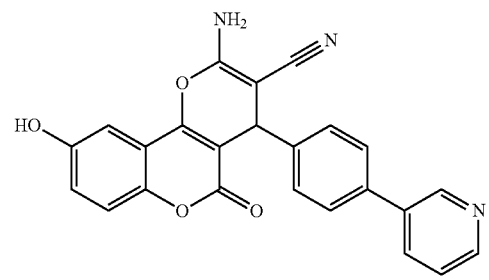<br>35 |
| A6 | 2f | 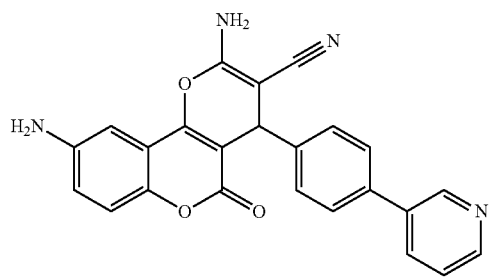<br>36 |
| A1 | 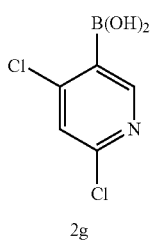 [SMILES: OB(O)c1cnc(Cl)cc1Cl]<br>2g | 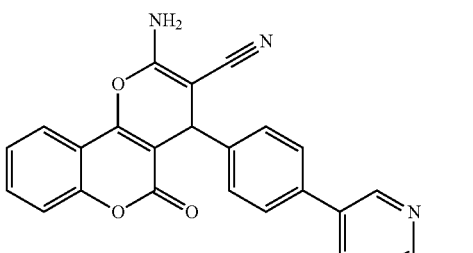<br>37 |

TABLE 2-continued
| Aryl bromide compound (A) | Boronic Acid (D) | Compounds 1-96 (Compounds of Formula E/ Formula (I)) |
|---|---|---|
| A2 | 2g | 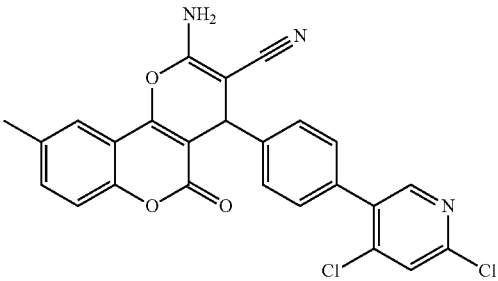<br>38 |
| A3 | 2g | 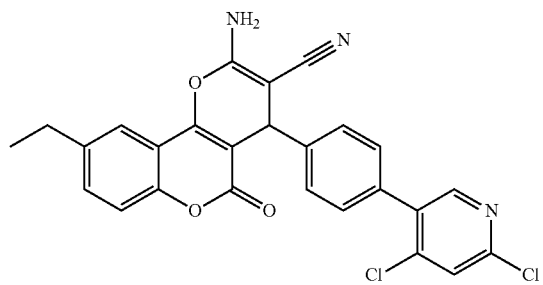<br>39 |
| A4 | 2g | 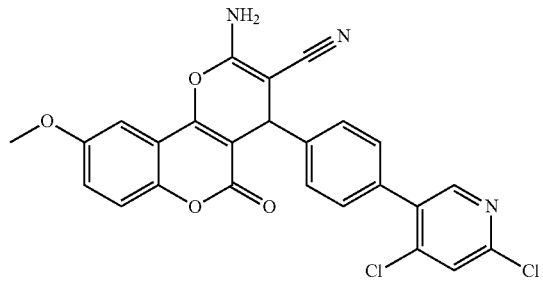<br>40 |
| A5 | 2g | 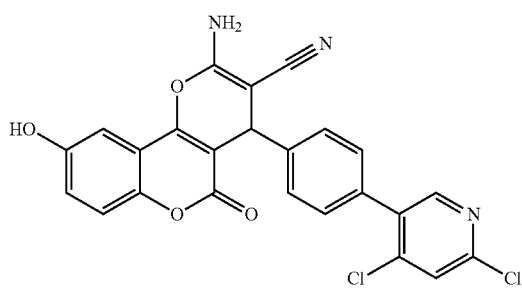<br>41 |

TABLE 2-continued
| Aryl bromide compound (A) | Boronic Acid (D) | Compounds 1-96 (Compounds of Formula E/ Formula (I)) |
|---|---|---|
| A6 | 2g | 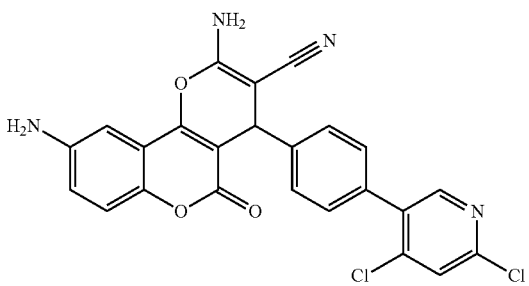<br>42 |
| A1 | 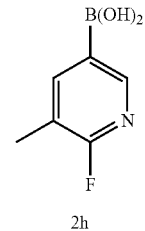<br>2h | 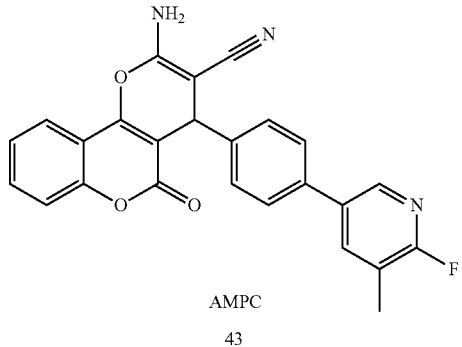<br>AMPC<br>43 |
| A2 | 2h | 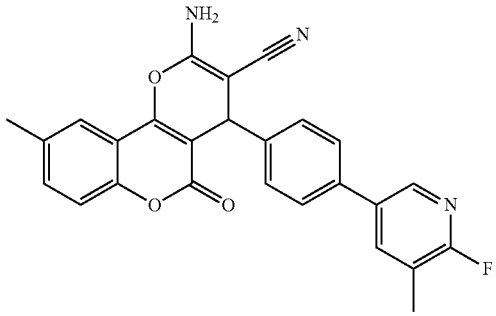<br>44 |
| A3 | 2h | 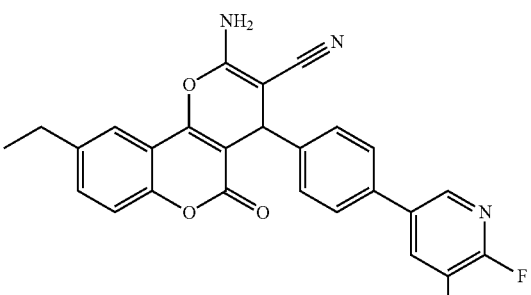<br>45 |

TABLE 2-continued
| Aryl bromide compound (A) | Boronic Acid (D) | Compounds 1-96 (Compounds of Formula E/ Formula (I)) |
|---|---|---|
| A4 | 2h | 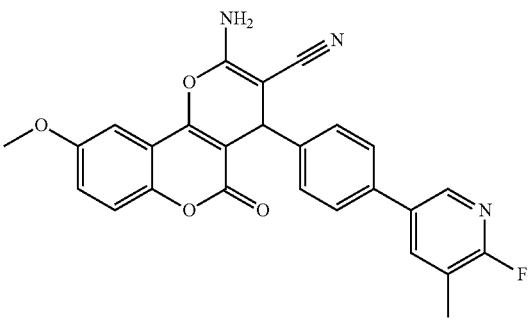<br>46 |
| A5 | 2h | 47 |
| A6 | 2h | 48 |
| A7 | 2a | 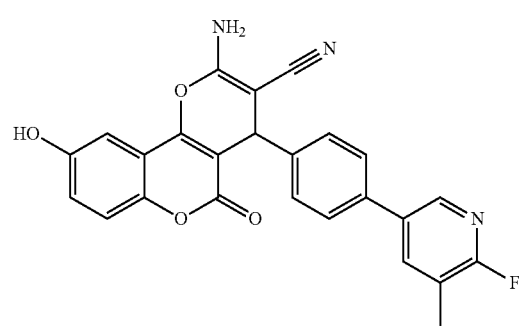 [SMILES: N#CC1=C(N)Oc2c(c(=O)oc3ccc(O)cc23)C1c1ccc(-c2cnc(Cl)cc2Cl)cc1]<br>49 |

TABLE 2-continued
| Aryl bromide compound (A) | Boronic Acid (D) | Compounds 1-96 (Compounds of Formula E/ Formula (I)) |
|---|---|---|
| 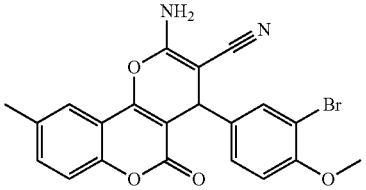 A8 | 2a | 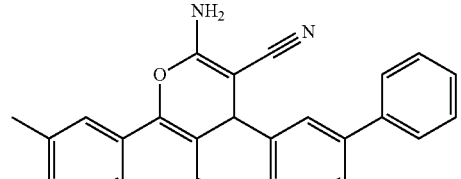 50 |
| 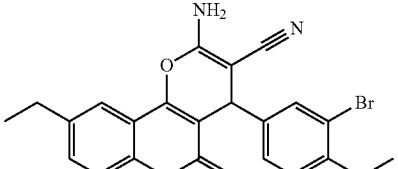 A9 | 2a | 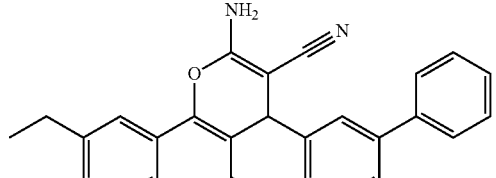 51 |
| 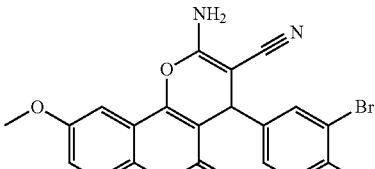 A10 | 2a | 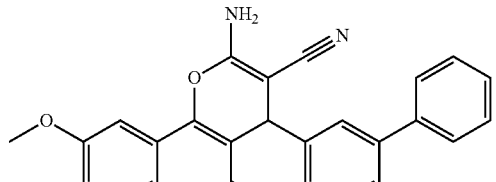 52 |
| 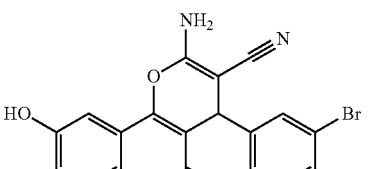 A11 | 2a | 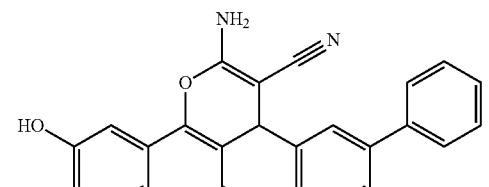 53 |
| 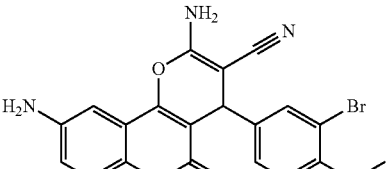 A12 | 2a | 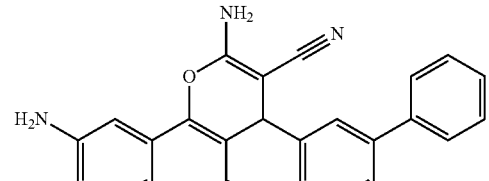 54 |
| A7 | 2b | 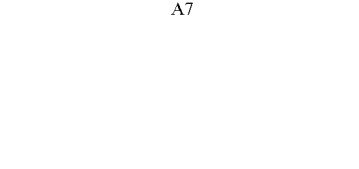 55 |

TABLE 2-continued
| Aryl bromide compound (A) | Boronic Acid (D) | Compounds 1-96 (Compounds of Formula E/ Formula (I)) |
|---|---|---|
| A8 | 2b | 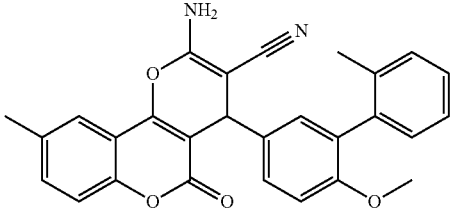<br>56 |
| A9 | 2b | 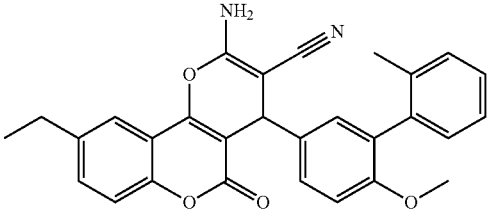<br>57 |
| A10 | 2b | 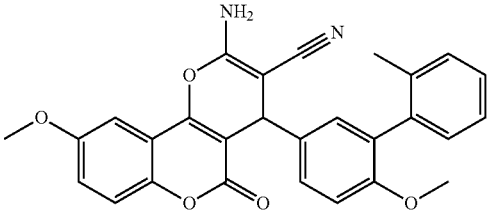<br>58 |
| A11 | 2b | 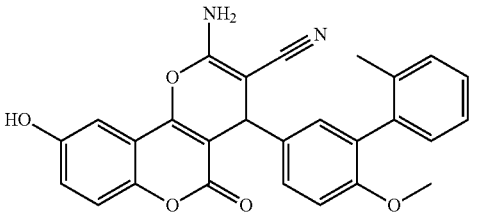<br>59 |
| A12 | 2b | 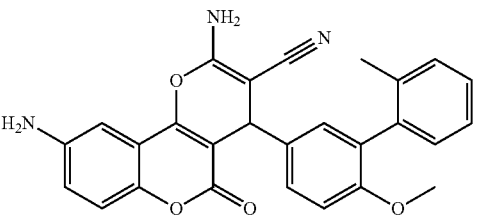<br>60 |
| A7 | 2c | 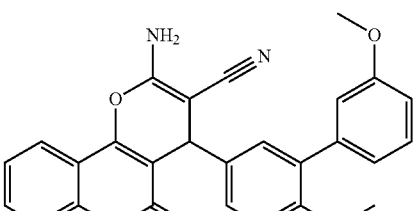<br>61 |

TABLE 2-continued
| Aryl bromide compound (A) | Boronic Acid (D) | Compounds 1-96 (Compounds of Formula E/ Formula (I)) |
|---|---|---|
| A8 | 2c | 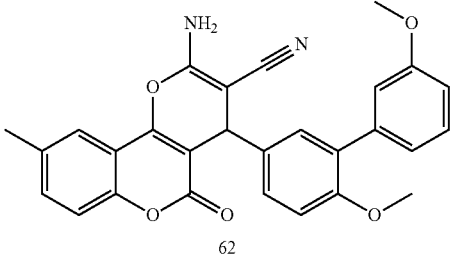<br>62 |
| A9 | 2c | 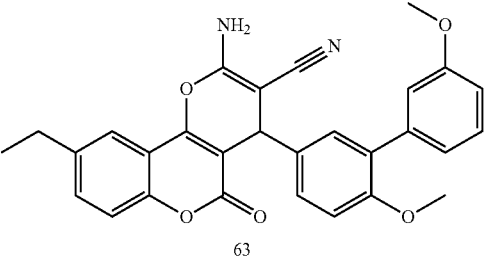<br>63 |
| A10 | 2c | 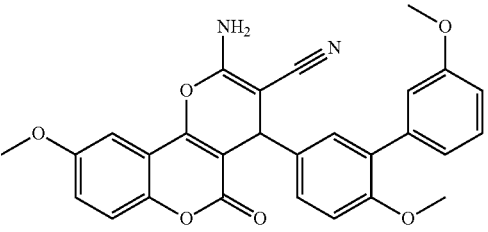<br>64 |
| A11 | 2c | 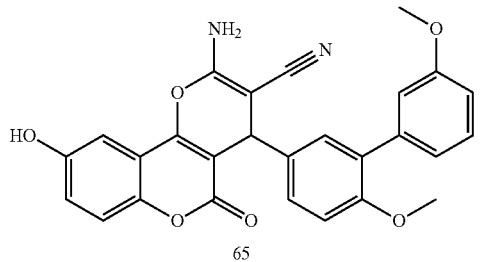<br>65 |
| A12 | 2c | 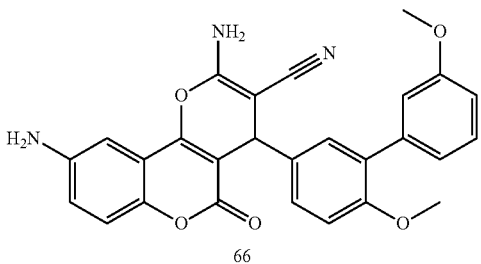<br>66 |

TABLE 2-continued
| Aryl bromide compound (A) | Boronic Acid (D) | Compounds 1-96 (Compounds of Formula E/ Formula (I)) |
|---|---|---|
| A7 | 2d | 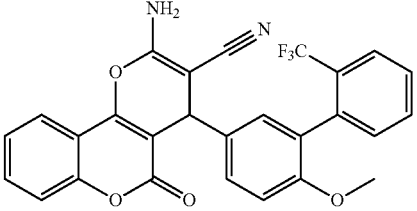<br>67 |
| A8 | 2d | 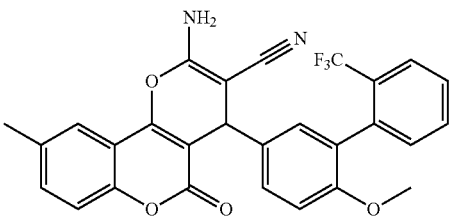<br>68 |
| A9 | 2d | 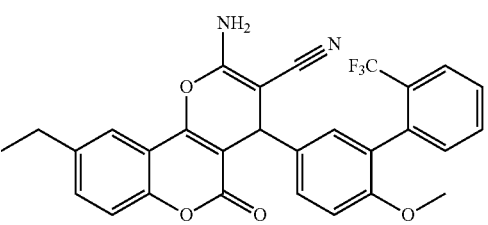<br>69 |
| A10 | 2d | 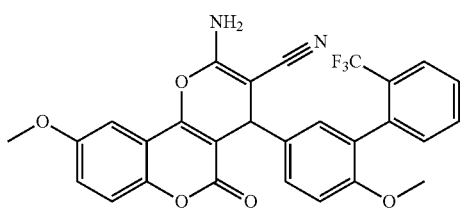<br>71 |
| A11 | 2d | 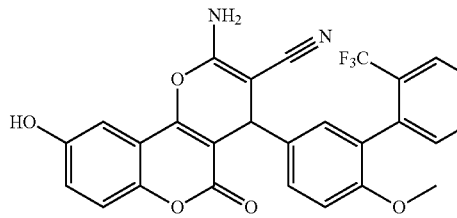<br>71 |
| A12 | 2d | 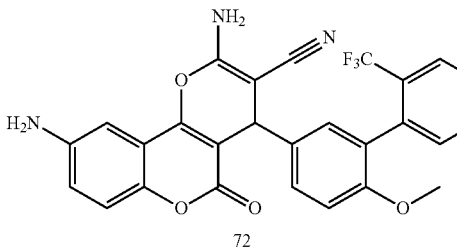<br>72 |

TABLE 2-continued
| Aryl bromide compound (A) | Boronic Acid (D) | Compounds 1-96 (Compounds of Formula E/ Formula (I)) |
|---|---|---|
| A7 | 2e | 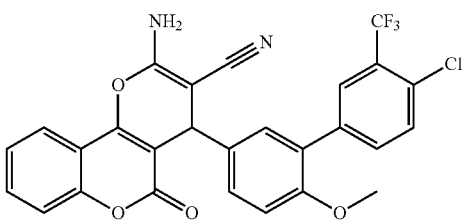<br>73 |
| A8 | 2e | 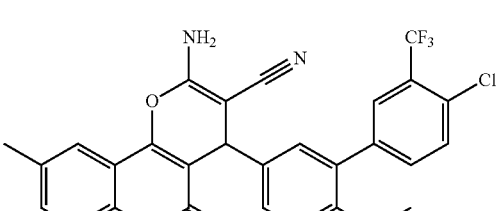<br>74 |
| A9 | 2e | 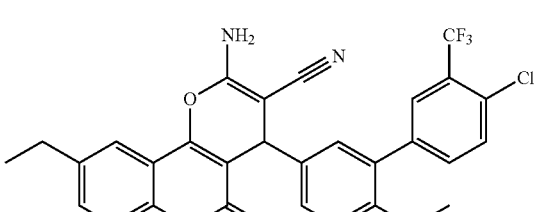<br>75 |
| A10 | 2e | 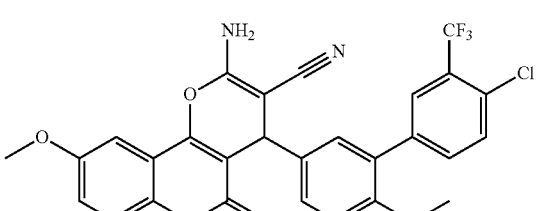<br>76 |
| A11 | 2e | 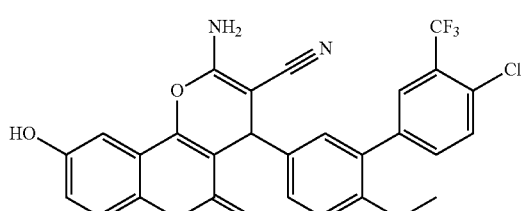<br>77 |
| A12 | 2e | 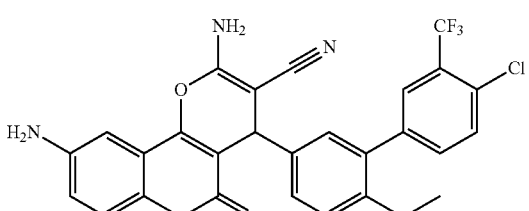<br>78 |

TABLE 2-continued
| Aryl bromide compound (A) | Boronic Acid (D) | Compounds 1-96 (Compounds of Formula E/ Formula (I)) |
|---|---|---|
| A7 | 2f | 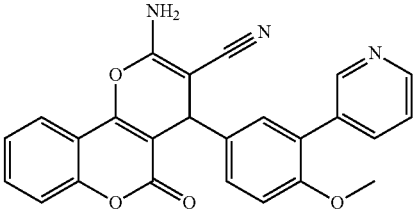<br>79 |
| A8 | 2f | 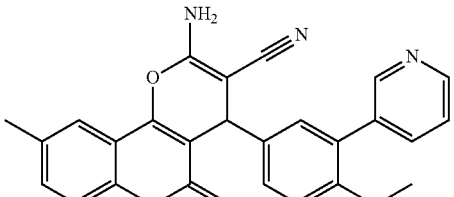<br>80 |
| A9 | 2f | 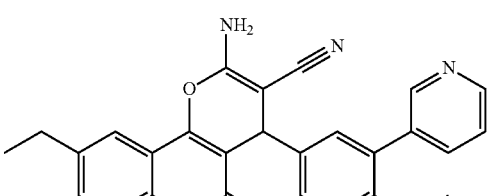<br>81 |
| A10 | 2f | 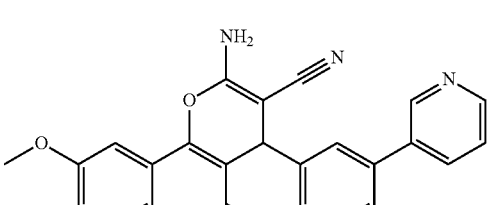<br>82 |
| A11 | 2f | 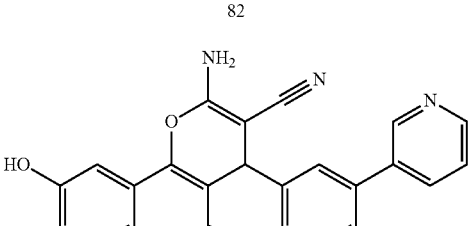<br>83 |
| A12 | 2f | 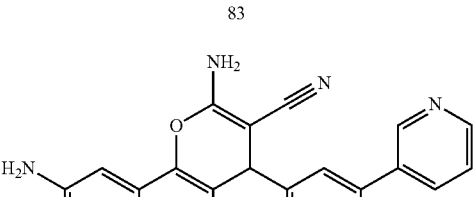<br>84 |

TABLE 2-continued
| Aryl bromide compound (A) | Boronic Acid (D) | Compounds 1-96 (Compounds of Formula E/ Formula (I)) |
|---|---|---|
| A7 | 2g | 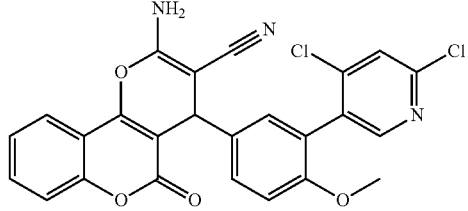<br>84 |
| A8 | 2g | 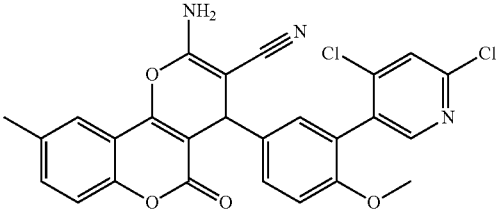<br>86 |
| A9 | 2g | 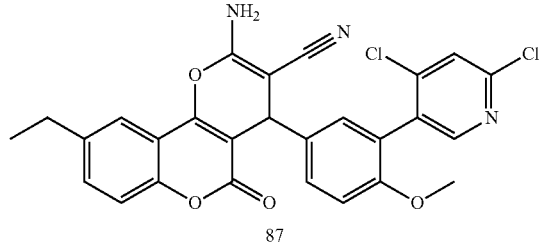<br>87 |
| A10 | 2g | 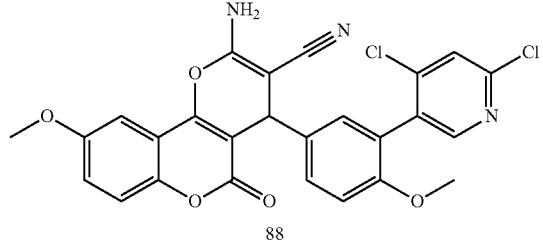<br>88 |
| A11 | 2g | 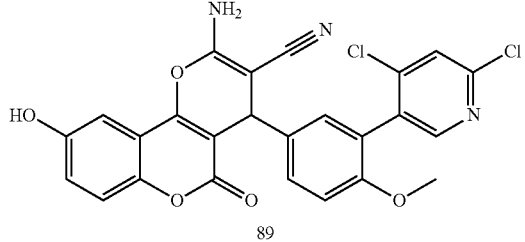<br>89 |
| A12 | 2g | 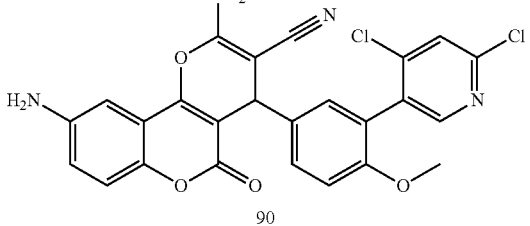<br>90 |

TABLE 2-continued
| Aryl bromide compound (A) | Boronic Acid (D) | Compounds 1-96 (Compounds of Formula E/ Formula (I)) |
|---|---|---|
| A7 | 2h | 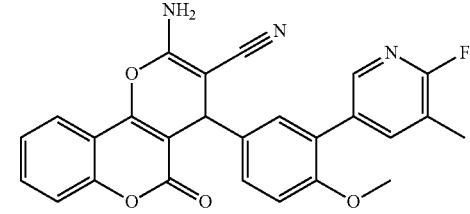<br>(methoxy-AMPC)<br>91 |
| A8 | 2h | 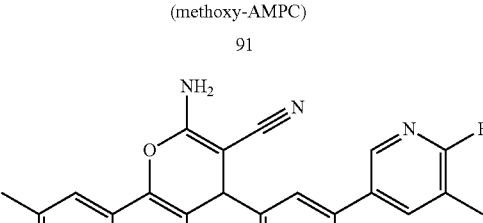<br>92 |
| A9 | 2h | 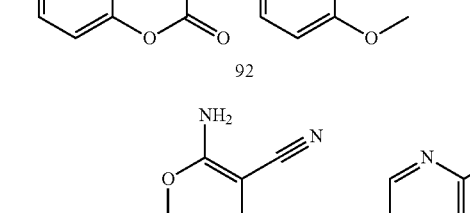<br>93 |
| A10 | 2h | 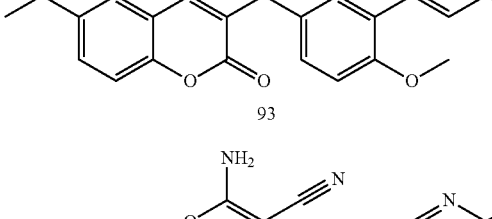<br>94 |
| A11 | 2h | 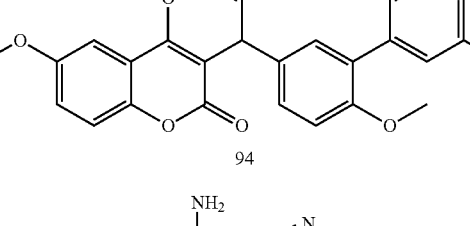<br>95 |
| A12 | 2h | 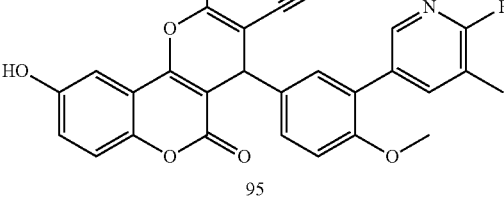<br>96 |

Characterization of Compound 1:
IR $v_{max}$ (cm$^{-1}$): 3323, 2194, 1673, 1049; $^1$H NMR (CDCl$_3$, 300 MHz): –δ 7.91-7.20 (m, 13H, Ar—H), 4.85 (s, 1H, methine); $^{13}$C NMR (CDCl$_3$, 75 MHz) δ 161.13, 160.57, 158.53, 156.08, 148.44, 145.95, 134.46, 130.35, 129.75, 128.17, 126.57, 125.46, 124.53, 123.48, 117.66, 112.60, 103.83, 60.20, 35.13; LCMS (MM:ES+APCI) (M+H)$^+$ 393.

Characterization of Compound 2:
IR $v_{max}$ (cm$^{-1}$): 3320, 2182, 1660, 1052; $^1$H NMR (CDCl$_3$, 300 MHz): δ 7.85-7.13 (m, 12H, Ar—H), 6.50 (s, 2H, —NH$_2$), 4.32 (s, 1H, Methine), 2.43 (s, 3H, —CH$_3$); LCMS (MM:ES+APCI) (M+H)$^+$ 407.

Characterization of Compound 3:
IR $v_{max}$ (cm$^{-1}$): 3315, 2191, 1665, 1048; $^1$H NMR (CDCl$_3$, 300 MHz): δ 7.92-7.10 (m, 12H, Ar—H), 6.79 (s, 2H, —NH$_2$), 4.35 (s, 1H, Methine), 2.89 (m, 2H, —CH$_2$—), 1.20 (t, 3H, —CH$_3$); LCMS (MM:ES+APCI) (M+H)$^+$ 421.

Characterization of Compound 4
IR $v_{max}$ (cm$^{-1}$): 3321, 2205, 1670, 1053; $^1$H NMR (CDCl$_3$, 300 MHz): δ 7.89-6.90 (m, 12H, Ar—H), 5.98 (s, 2H, —NH$_2$), 4.57 (s, 1H, Methine), 3.68 (s, 3H, —OCH$_3$); LCMS (MM:ES+APCI) (M+H)$^+$ 423.

Characterization of Compound 5:
IR $v_{max}$ (cm$^{-1}$): 3321, 2205, 1670, 1053; $^1$H NMR (CDCl$_3$, 300 MHz): δ 9.41 (s, 1H, —OH), 7.82-6.95 (m, 12H, Ar—H), 5.64 (s, 2H, —NH$_2$), 4.32 (s, 1H, Methine); LCMS (MM:ES+APCI) (M+H)$^+$ 419.

Characterization of Compound 6:
IR $v_{max}$ (cm$^{-1}$): 3325, 2210, 1668, 1042; $^1$H NMR (CDCl$_3$, 300 MHz): δ 9.08 (s, 2H, —NH$_2$), 7.86-7.02 (m, 12H, Ar—H), 6.81 (s, 2H, —NH$_2$), 4.25 (s, 1H, Methine); LCMS (MM:ES+APCI) (M–H)$^-$ 406.

Characterization of Compound 7:
IR $v_{max}$(cm$^{-1}$): 3323, 2194, 1673, 1049; $^1$H NMR (CDCl$_3$, 300 MHz): –δ 7.91-7.20 (m, 13H, Ar—H), 4.15 (s, 1H, methine), 3.32 (s, 2H, —NH$_2$), 2.23 (s, 3H, —CH$_3$); 13C NMR (CDCl$_3$, 75 MHz) δ 161.13, 160.57, 158.53, 156.08, 148.44, 145.95, 13.46, 130.35, 129.75, 128.17, 126.57, 125.46, 124.53, 123.48, 117.66, 112.60, 103.83, 60.20, 35.13; LCMS (MM:ES+APCI) (M+H)$^+$ 407, Characterization of Compound 8:
IR $v_{max}$ (cm$^{-1}$): 3319, 2195, 1670, 1055; $^1$H NMR (CDCl$_3$, 300 MHz): –δ 7.83-7.18 (m, 11H, Ar—H), 4.29 (s, 1H, methine), 3.82 (s. 2H, —NH$_2$), 2.42 (s, 6H, —CH$_3$); LCMS (MM:ES+APCI) (M+H)$^+$ 421.

Characterization of Compound 9:
IR $v_{max}$(cm$^{-1}$): 3315, 2215, 1681, 1060; $^1$H NMR (CDCl$_3$, 300 MHz): –δ 7.69-7.05 (m, 11H, Ar—H), 6.72 (s, 2H, —NH$_2$), 4.81 (s, 1H, methine), 2.62 (m, 2H, —CH$_2$—), 2.08 (t, 3H, —CH$_3$), 1.58 (s, 3H, —CH$_3$); LCMS (MM:ES+APCI) (M–H)$^-$ 433.

Characterization of Compound 210
IR $v_{max}$ (cm$^{-1}$): 3311, 2220, 1691, 1058; $^1$H NMR (CDCl$_3$, 300 MHz): –δ 7.89-7.11 (m, 11H, Ar—H), 6.51 (s, 2H, —NH$_2$), 4.81 (s, 1H, methine), 3.68 (s, 3H, —OCH$_3$), 2.28 (s, 3H, —CH$_3$); LCMS (MM:ES+APCI) (M+H)$^+$ 437.

Characterization of Compound 11:
IR $v_{max}$ (cm$^{-1}$): 3320, 2218, 1696, 1049; $^1$H NMR (CDCl$_3$, 300 MHz): –δ 9.65 (s, 1H, —OH), 7.89-7.11 (m, 11H, Ar—H), 6.79 (s, 2H, —NH$_2$), 4.59 (s, 1H, methine), 2.19 (s, 3H, —CH$_3$); LCMS (MM:ES+APCI) (M+H)$^+$ 423.

Characterization of Compound 12:
IR $v_{max}$(cm$^{-1}$): 3319, 2221, 1688, 1045; $^1$H NMR (CDCl$_3$, 300 MHz): –δ 7.76-7.20 (m, 11H, Ar—H), 6.81 (s, 2H, —NH$_2$), 5.70 (s, 2H, —NH$_2$), 4.67 (s, 1H, methine), 2.23 (s, 3H, —CH$_3$); LCMS (MM:ES+APCI) (M–H)$^-$ 420.

Characterization of Compound 13:
IR $v_{max}$ (cm$^{-1}$): 3293, 2193, 1673, 1048; $^1$H NMR (CDCl$_3$, 300 MHz): –δ 8.00-7.97 (m, 3H, Ar—H), 7.79-7.74 (m, 2H. Ar—H). 7.55-7.52 (n, 2H, Ar—H), 7.43-7.39 (m, 4H, Ar—H), 7.27 (s, 1H, Ar—H), 4.63 (s, 1H, Methine), 3.84 (s, 3H, Methoxy); $^{13}$C NMR (DMSO-D$_6$, 75 MHz) δ 162.52, 160.19, 143.72, 134.25, 131.56, 126.11, 125.87, 125.09, 124.35, 123.46, 122.92, 121.62, 120.95, 120.12, 117.57, 114.29, 112.52, 99.35, 57.28, 52.25, 35.28: LCMS (MM:ES+APCI) (M+H)+423, Characterization of Compound 14:
IR $v_{max}$ (cm$^{-1}$): 3321, 2219, 1675.1042; $^1$H NMR (CDCl$_3$, 300 MHz): –δ 7.70-7.09 (m, 11H, Ar—H), 6.59 (s, 2H, —NH$_2$), 4.71 (s, 1H, methine), 3.79 (s, 3H, —OCH$_3$), 2.19 (s, 3H, —CH$_3$); LCMS (MM:ES+APCI) (M+H)$^+$ 437.

Characterization of Compound 15:
IR $v_{max}$ (cm$^{-1}$): 3328, 2221, 1670, 1045; $^1$H NMR (CDCl$_3$, 300 MHz): –δ 7.82-7.19 (n, 11H, Ar—H), 6.81 (s, 2H, —NH$_2$), 4.68 (s, 1H, methine), 3.79 (s, 3H, —OCH$_3$), 2.77 (m, 2H, —CH$_2$—), 1.39 (t, 3H, —CH$_3$); LCMS (MM:ES+APCI) (M+H)$^+$ 451.

Characterization of Compound 16:
IR $v_{max}$ (cm$^{-1}$): 3322, 2211, 1665, 1049; $^1$H NMR (CDCl$_3$, 300 MHz): –δ 7.91-7.06 (m, 11H, Ar—H), 6.48 (s, 2H, —NH$_2$), 4.35 (s, 1H, methine), 3.85 (s, 6H, —OCH$_3$); LCMS (MM:ES+APCI) (M+H)$^+$ 453.

Characterization of Compound 17:
IR $v_{max}$ (cm$^{-1}$): 3329, 2211, 1670, 1051; $^1$H NMR (CDCl$_3$, 300 MHz): –δ 9.15 (s, 1H, —OH), 7.81-7.11 (m, 11H, Ar—H), 6.88 (s, 2H, —NH$_2$), 4.64 (s, 1H, methine), 3.83 (s, 3H, —OCH$_3$); LCMS (MM:ES+APCI) (M+H)$^+$ 439.

Characterization of Compound 18:
IR $v_{max}$ (cm$^{-1}$): 3319, 2220, 1665, 1039; $^1$H NMR (CDCl$_3$, 300 MHz): –δ 7.89-7.08 (n, 11H, Ar—H), 6.88 (s, 2H, —NH$_2$), 5.65 (s, 2H, —NH$_2$), 4.34 (s, 1H, methine), 3.85 (s, 3H, —OCH$_3$); LCMS (MM:ES+APCI) (M+H)$^+$ 438.

Characterization of Compound 19:
IR $v_{max}$: 3292 cm$^{-1}$ $v_{(NH2)}$, 2199 cm$^{-1}$ $v_{(CN)}$, 1669 cm$^{-1}$ $v_{(C—O)}$; 1033 cm$^{-1}$ $v_{(C=O)}$; $^1$H NMR (CDCl$_3$, 300 MHz): –δ 7.83-7.26 (m, 12H, Ar—H), 4.71 (s, 1H, Methine); $^{13}$C NMR (CDCl$_3$, 75 MHz) δ 162.57, 161.43, 159.27, 158.12, 143.29, 141.25, 135.04, 132.81, 128.77, 126.92, 126.03, 125.12, 124.69, 123.14, 121.20, 120.07, 118.77, 116.83, 110.32, 100.05, 58.23, 38.48; LCMS (MM:ES+APCI) (M+H)$^+$ 461.

Characterization of Compound 20:
IR $v_{max}$ (cm$^{-1}$): 3317, 2220, 1686, 1039; $^1$H NMR (CDCl$_3$, 300 MHz): –δ 7.81-7.05 (m, 11H, Ar—H), 6.75 (s, 2H, —NH$_2$), 4.32 (s, 1H, methine), 2.22 (s, 3H, —CH$_3$); LCMS (MM:ES+APCI) (M+H)$^+$ 475.

Characterization of Compound 21:
IR $v_{max}$ (cm$^{-1}$): 3326, 2191, 1680, 1048; $^1$H NMR (CDCl$_3$, 300 MHz): –δ 7.96-7.22 (m, 11H, Ar—H), 6.43 (s, 2H, —NH$_2$), 4.29 (s, 1H, methine), 2.52 (m, 2H, —CH$_2$—), 1.21 (t, 3H, —CH$_3$); LCMS (MM:ES+APCI) (M–H)$^-$ 487.

Characterization of Compound 22:
IR $v_{max}$ (cm$^{-1}$): 3319, 2226, 1671, 1053; $^1$H NMR (CDCl$_3$, 300 MHz): –δ 7.88-7.12 (m, 11H, Ar—H), 6.77 (s, 2H, —NH$_2$), 4.62 (s, 1H, methine), 3.85 (s, 3H, —OCH$_3$); LCMS (MM:ES+APCI) (M+H)$^+$ 491.

Characterization of Compound 23:
IR $v_{max}$(cm$^{-1}$): 3319, 2198, 1660, 1042; $^1$H NMR (CDCl$_3$ 300 MHz): –δ 9.65 (s, 1H, —OH), 7.79-6.95 (m, 11H, Ar—H), 6.56 (s, 2H, —NH$_2$), 4.34 (s, 1H, methine); LCMS (MM:ES+APCI) (M+H)$^+$ 477.

Characterization of Compound 24:
IR ν$_{max}$ (cm$^{-1}$): 3321, 2218, 1670, 1049; $^1$H NMR (CDCl$_3$, 300 MHz): –δ 7.81-7.10 (m, 11H, Ar—H), 6.85 (s, 2H, —NH$_2$), 5.62 (s, 2H, —NH$_2$) 4.36 (s, 1H, methine); LCMS (MM:ES+APCI) (M+H)$^+$ 476.

Characterization of Compound 25:
IR ν$_{max}$: 3293 cm$^{-1}$ ν$_{(NH2)}$, 2200 cm$^{-1}$ ν$_{(CN)}$, 1667 cm$^{-1}$ ν$_{(C=O)}$, 1050 cm$^{-1}$ ν$_{(C=O)}$; $^1$H NMR (CDCl$_3$, 300 MHz): –δ 7.84-7.26 (m, 11H, Ar—H), 4.85 (s, 1H, Methine); $^{13}$C NMR (CDCl$_3$, 75 MHz) δ 161.08, 160.50, 158.19, 141.89, 135.08, 132.50, 130.19, 128.11, 127.47, 126.09, 124.05, 123.74, 122.29, 121.08, 119.85, 117.64, 115.24, 111.48, 101.56, 60.15, 36.22; LCMS (MM:ES+APCI) (M–H)$^-$ 493.

Characterization of Compound 26:
IR ν$_{max}$(cm$^{-1}$): 3320, 2218, 1673, 1041; $^1$H NMR (CDCl$_3$, 300 MHz): –δ 7.90-7.12 (m, 11H, Ar—H), 6.68 (s, 2H, —NH$_2$), 4.44 (s, 1H, methine), 2.18 (s, 3H, —CH$_3$); LCMS (MM:ES+APCI) (M+H)$^+$ 509.

Characterization of Compound 27:
IR ν$_{max}$ (cm$^{-1}$): 3321, 2221, 1673, 1039; $^1$H NMR (CDCl$_3$, 300 MHz): –δ 7.87-7.15 (m, 11H, Ar—H), 5.95 (s, 2H, —NH$_2$), 4.51 (s, 1H, methine), 2.61 (m, 2H, —CH$_2$—), 1.25 (t, 3H, —CH$_3$); LCMS (MM:ES+APCI) (M+H)$^+$ 523.

Characterization of Compound 28:
IR ν$_{max}$ (cm$^{-1}$): 3320, 2225, 1662, 1045; $^1$H NMR (CDCl$_3$, 300 MHz): –δ 7.96-7.20 (m, 11H, Ar—H), 6.84 (s, 2H, —NH$_2$), 4.39 (s, 1H, methine), 3.81 (s, 3H, —OCH$_3$); LCMS (MM:ES+APCI) (M+H)$^+$ 525.

Characterization of Compound 29:
IR ν$_{max}$(cm$^{-1}$): 3325, 2222, 1655, 1051; $^1$H NMR (CDCl$_3$, 300 MHz): –δ 9.12 (s, 1H, —OH), 7.62-6.91 (m, 11H, Ar—H), 5.86 (s, 2H, —NH$_2$), 4.41 (s, 1H, methine); LCMS (MM:ES+APCI) (M+H)$^+$ 511.

Characterization of Compound 30:
IR ν$_{max}$ (cm$^{-1}$): 3321, 2218, 1670, 1049; $^1$H NMR (CDCl$_3$, 300 MHz): –δ 7.92-7.15 (m, 10H, Ar—H), 6.25 (s, 2H, —NH$_2$), 4.93 (s, 2H, —NH$_2$) 4.38 (s, 1H, methine); LCMS (MM:ES+APCI) (M+H)$^+$ 510.

Characterization of Compound 31:
IR ν$_{max}$ (cm$^{-1}$): 3323, 2195, 1668, 1042; $^1$H NMR (CDCl$_3$, 300 MHz): –δ 8.92-8.91 (s, 1H, Pyr-H), 8.68-8.67 (d, 1H, Pyr-H), 8.56-8.54 (d, 1H, Pyr-H), 7.99-7.96 (m, 2H, Ar—H), 7.86-7.84 (m, 1H, Ar—H), 7.58-7.57 (m, 3H, Ar—H), 7.42-7.37 (m, 3H, Ar—H), 4.74 (s, 1H, Methine), 1.566 (s, 2H, —NH$_2$); LCMS (MM:ES+APCI) (M+H)$^+$ 394.

Characterization of Compound 32:
IR ν$_{max}$(cm$^{-1}$): 3315, 2198, 1652, 1050; $^1$H NMR (CDCl$_3$, 300 MHz): –δ 8.25-7.92 (m, 4H, Pyr-H), 7.85-7.21 (m, 7H, Ar—H), 6.72 (s, 2H, —NH$_2$), 4.32 (s, 1H, methine), 2.48 (s, 3H, —CH$_3$); LCMS (MM:ES+APCI) (M+H)$^+$ 408.

Characterization of Compound 33:
IR ν$_{max}$ (cm$^{-1}$): 3325, 2221, 1671, 1045; $^1$H NMR (CDCl$_3$, 300 MHz): –δ 8.87-8.05 (m, 4H, Pyr-H), 7.92-7.16 (s, 7H, Ar—H), 6.76 (s, 2H, —NH$_2$), 4.35 (s, 1H, methine), 2.82 (m, 2H, —CH$_2$—), 1.32 (t, 3H, —CH$_3$); LCMS (MM:ES+APCI) (M+H)$^+$ 422.

Characterization of Compound 34:
IR ν$_{max}$ (cm$^{-1}$): 3317, 2220, 1668, 1043; $^1$H NMR (CDCl$_3$, 300 MHz): –δ 8.72-8.12 (m, 4H, Pyr-H), 7.83-7.09 (m, 7H, Ar—H), 6.61 (s, 2H, —NH$_2$), 4.39 (s, 1H, methine), 3.79 (s, 3H, —OCH$_3$); LCMS (MM:ES+APCI) (M+H)$^+$ 424.

Characterization of Compound 35:
IR ν$_{max}$(cm$^{-1}$): 3332, 2219, 1642, 1049; $^1$H NMR (CDCl$_3$, 300 MHz): –δ 9.12 (s, 1H, —OH), 8.52-8.02 (m, 4H, PyAr-H), 7.84-7.21 (s, 7H. Ar—H), 6.86 (s, 2H, —NH$_2$), 4.53 (s, 1H, methine); LCMS (MM:ES+APCI) (M+H)$^+$ 410.

Characterization of Compound 36:
IR ν$_{max}$(cm$^{-1}$): 3332, 2215, 1668, 1050; $^1$H NMR (CDCl$_3$, 300 MHz): –δ 8.62-7.93 (m, 4H, Pyr-H), 7.81-7.24 (s, 7H, Ar—H), 6.38 (s, 2H, —NH$_2$), 5.53 (s, 2H, —NH$_2$), 4.61 (s, 1H, methine); LCMS (MM:ES+APCI) (M+H)$^+$ 409.

Characterization of Compound 37:
IR ν$_{max}$ (cm$^{-1}$): 3320, 2192, 1665, 1046; $^1$H NMR (CDCl$_3$, 300 MHz): –δ 8.62 (s, 1H, Ar—N—H), 8.46 (s, 1H, Ar—H), 7.77 (m, 1H, Ar—H), 7.59-7.50 (m, 1H, Ar—H), 7.38-7.32 (m, 2H, Ar—H), 7.00-6.89 (m, 3H, Ar—H), 3.72 (s, 1H, Methine); LCMS (MM:ES+APCI) (M+H)$^+$ 463.

Characterization of Compound 38:
IR ν$_{max}$(cm$^{-1}$): 3323, 2199, 1661, 1042; $^1$H NMR (CDCl$_3$, 300 MHz): –δ 8.76 (s. 1H, Pyr-H), 8.33 (s, 1H, Pyr-H), 7.92-7.64 (m, 7H, Ar—H), 6.72 (s, 2H, —NH$_2$), 4.32 (s, 1H, methine), 2.48 (s, 3H, —CH$_3$); LCMS (MM:ES+APCI) (M+H)$^+$ 476.

Characterization of Compound 39:
IR ν$_{max}$(cm$^{-1}$): 3323, 2219, 1668, 1051; $^1$H NMR (CDCl$_3$, 300 MHz): –δ 8.71 (s, 1H, Pyr-H), 8.53 (s, 1H, Pyr-H), 6.76 (s, 2H, —NH$_2$), 4.35 (s, 1H, methine), 2.77 (m, 2H, —CH$_2$—), 1.65 (t, 3H, —CH$_3$); LCMS (MM:ES+APCI) (M–H)$^-$ 488.

Characterization of Compound 40:
IR ν$_{max}$ (cm$^{-1}$): 3321, 2217, 1670, 1051; $^1$H NMR (CDCl$_3$, 300 MHz): –δ 8.61 (s, 1H, Pyr-H), 8.35 (s, 1H, Pyr-H), 7.81-7.22 (m, 7H, Ar—H), 6.58 (s, 2H, —NH$_2$), 4.61 (s, 1H, methine), 3.81 (s, 3H, —OCH$_3$); LCMS (MM:ES+APCI) (M+H)$^+$ 492.

Characterization of Compound 41:
IR ν$_{max}$ (cm$^{-1}$): 3330, 2221, 1650, 1047; $^1$H NMR (CDCl$_3$, 300 MHz): –δ 9.12 (s, 1H, —OH), 8.31 (s, 1H, Py-H), 8.19 (s, 1H, Pyr-H), 7.96-7.33 (s, 7H, Ar—H), 6.78 (s, 2H, —NH$_2$), 4.38 (s, 1H, methine); LCMS (MM:ES+APCI) (M+H)$^+$ 478.

Characterization of Compound 42:
IR ν$_{max}$(cm$^{-1}$): 3329, 2218, 1670, 1046; $^1$H NMR (CDCl$_3$, 300 MHz): –δ 8.64 (s, 1H, Pyr-H), 8.49 (s, 1H, Pyr-H), 7.90-7.35 (s, 7H, Ar—H), 6.72 (s, 2H, —NH$_2$), 5.61 (s, 2H, —NH$_2$), 4.55 (s, 1H, methine); LCMS (MM:ES+APCI) (M+H)$^+$ 477.

Characterization of Compound 43:
IR ν$_{max}$ (cm$^{-1}$): 3256, 2196, 1680, 1047; $^1$H NMR (CDCl$_3$, 300 MHz): δ 8.00 (s, 1H, Pyr-H), 7.83-7.81 (s, 1H, Pyr-H), 7.64-6.83 (m, 8H, Ar—H), 4.71 (s, 1H, Methine), 2.29 (s, 3H, —CH$_3$), 1.73 (s, 2H, —NH$_2$); $^{13}$C NMR (CDCl$_3$, 75 MHz) δ 160.27, 158.52, 152.52, 135.28, 133.92, 131.25, 128.92, 125.58, 124.89, 124.51, 123.98, 123.03, 122.85, 120.50, 118.35, 116.15, 112.35, 60.20, 38.40, 15.81; LCMS (MM:ES+APCI) (M–H)$^+$ 424.

Characterization of Compound 44:
IR ν$_{max}$(cm$^{-1}$): 3320, 2219, 1651, 1060; $^1$H NMR (CDCl$_3$, 300 MHz): δ 8.76 (s, 1H, Pyr-H), 8.51 (s, 1H, Pyr-H), 7.72-7.21 (m, 7H, Ar—H), 6.65 (s, 2H, —NH$_2$), 4.48 (s, 1H, methine), 2.38 (s, 6H, —CH$_3$); LCMS (MM:ES+APCI) (M+H)$^+$ 440.

Characterization of Compound 45:
IR ν$_{max}$ (cm$^{-1}$): 3323, 2219, 1668, 1051; $^1$H NMR (CDCl$_3$, 300 MHz): δ 8.79-8.71 (s, 1H, Pyr-H), 8.53-7.48 (s, 1H, Pyr-H), 7.69-7.21 (m, 7H, Ar—H), 6.76 (s, 2H, —NH$_2$), 4.35 (s, 1H, methine), 2.64 (m, 2H, —CH$_2$—), 2.51 (s, 3H, —CH$_3$), 1.59 (t, 3H, —CH$_3$); LCMS (MM:ES+APCI) (M–H)$^-$ 454.

Characterization of Compound 46:
IR $v_{max}$ (cm$^{-1}$): 3330, 2219, 1665, 1043; $^1$H NMR (CDCl$_3$, 300 MHz): δ 8.65 (s, 1H, Pyr-H), 8.41 (s, 1H, Pyr-H), 7.69-7.13 (m, 7H, Ar—H), 6.58 (s, 2H, —NH$_2$), 4.61 (s, 1H, methine), 3.79 (s, 3H, —OCH$_3$), 2.87 (s, 3H, —CH$_3$); LCMS (MM:ES+APCI) (M+H)$^+$ 456.

Characterization of Compound 47:
IR $v_{max}$ (cm$^{-1}$): 3328, 2218, 1644, 1049; $^1$H NMR (CDCl$_3$, 300 MHz): -δ 8.99 (s, 1H, —OH), 8.65 (s, 1H, Py-H), 8.28 (s, 1H, Pyr-H), 7.85-7.21 (s, 7H, Ar—H), 6.59 (s, 2H, —NH$_2$), 4.23 (s, 1H, methine), 2.59 (s, 3H, —CH$_3$); LCMS (MM:ES+APCI) (M+H)$^+$ 442.

Characterization of Compound 48:
IR $v_{max}$(cm$^{-1}$): 3332, 2215, 1667, 1039; $^1$H NMR (CDCl$_3$, 300 MHz): -δ 8.63 (s, 1H, Pyr-H), 8.25 (s, 1H, Pyr-H), 7.78-7.14 (s, 7H, Ar—H), 5.96 (s, 2H, —NH$_2$), 5.11 (s, 2H, —NH$_2$), 4.45 (s, 1H, methine), 2.68 (s, 3H, —CH$_3$); LCMS (MM:ES+APCI) (M+H)$^+$ 477.

Characterization of Compound 49:
IR $v_{max}$ (cm$^{-1}$): 3286, 2197, 1667, 1052; $^1$H NMR (CDCl$_3$, 300 MHz): δ 7.79-7.77 (s, 1H, Ar—H), 7.77-7.7.5 (m, 1H, Ar—H), 7.49-7.46 (m, 2H, Ar—H), 7.37-7.33 (m, 6H, Ar—H), 7.19-7.18 (m, 1H, Ar—H), 6.93-6.91 (m, 1H, Ar—H), 3.86 (s, 1H, Methine), 3.75-3.75 (s, 3H, —OCH$_3$); LCMS (MM:ES+APCI) (M–H)$^+$ 421.

Characterization of Compound 50:
IR $v_{max}$ (cm$^{-1}$): 3319, 2195, 1665, 1046; $^1$H NMR (CDCl$_3$, 300 MHz): δ 7.88-7.19 (m, 11H, Ar—H), 6.61 (s, 2H, —NH$_2$), 4.30 (s, 1H, methine), 3.71 (s, 3H, —OCH$_3$), 2.42 (s, 6H, —CH$_3$); LCMS (MM:ES+APCI) (M+H)$^+$ 437.

Characterization of Compound 51:
IR $v_{max}$(cm$^{-1}$): 3323, 2219, 1668, 1051; $^1$H NMR (CDCl$_3$, 300 MHz): δ 7.71-7.10 (m, 11H, Ar—H), 6.76 (s, 2H, —NH$_2$), 4.35 (s, 1H, methine), 3.56 (s, 3H, —OCH$_3$), 2.64 (m, 2H, —CH$_2$—), 1.59 (t, 3H, —CH$_3$); LCMS (MM:ES+APCI) (M+H)$^+$ 451.

Characterization of Compound 52:
IR $v_{max}$ (cm$^{-1}$): 3330, 2219, 1665, 1043; $^1$H NMR (CDCl$_3$, 300 MHz): δ 7.79-7.13 (m, 11H, Ar—H), 6.88 (s, 2H, —NH$_2$), 4.32 (s, 1H, methine), 3.79 (s, 6H, —OCH$_3$); LCMS (MM:ES+APCI) (M+H)$^+$ 453.

Characterization of Compound 53:
IR $v_{max}$(cm$^{-1}$): 3321, 2222, 1651, 1050; $^1$H NMR (CDCl$_3$, 300 MHz): -δ 8.99 (s, 1H, —OH), 7.85-7.11 (s, 11H, Ar—H), 6.59 (s, 2H, —NH$_2$), 4.23 (s, 1H, methine), 2.59 (s, 3H, —CH$_3$); LCMS (MM:ES+APCI) (M+H)$^+$ 439.

Characterization of Compound 54:
IR $v_{max}$ (cm$^{-1}$): 3332, 2215, 1667, 1039; $^1$H NMR (CDCl$_3$, 300 MHz): -δ 7.89-7.12 (s, 11H, Ar—H), 6.26 (s, 2H, —NH$_2$), 5.81 (s, 2H, —NH$_2$), 4.32 (s, 1H, methine), 3.68 (s, 3H, —OCH$_3$); LCMS (MM:ES+APCI) (M+H)$^+$ 437.

Characterization of Compound 55:
IR $v_{max}$ (cm$^{-1}$): 3288, 2196, 1668, 1057; $^1$H NMR (CDCl$_3$, 300 MHz): δ 7.77-7.75 (m, 1H, Ar—H), 7.35-7.34 (m, 3H, Ar—H), 7.26 (m, 3H, Ar—H), 7.03-6.90 (m, 4H, Ar—H), 4.62 (s, 1H, Methine), 3.73 (s, 3H, —OCH$_3$), 2.06 (s, 3H, —CH$_3$); LCMS (MM:ES+APCI) (M–H)$^-$ 435.

Characterization of Compound 56:
IR $v_{max}$(cm$^{-1}$): 3325, 2225, 1670, 1041; $^1$H NMR (CDCl$_3$, 300 MHz): δ 7.77-7.17 (m, 10H, Ar—H), 6.52 (s, 2H, —NH$_2$), 4.41 (s, 1H, methine), 3.79 (s, 3H, —OCH$_3$), 2.42 (s, 6H, —CH$_3$); LCMS (MM:ES+APCI) (M+H)$^+$ 451.

Characterization of Compound 57:
IR $v_{max}$(cm$^{-1}$): 3321, 2220, 1670, 1043; $^1$H NMR (CDCl$_3$, 300 MHz): δ 7.69-7.14 (m, 10H, Ar—H), 6.76 (s, 2H, —NH$_2$), 4.35 (s, 1H, methine), 3.56 (s, 3H, —OCH$_3$), 2.64 (m, 2H, —CH$_2$—), 1.59 (t, 3H, —CH$_3$); LCMS (MM:ES+APCI) (M+H)$^+$ 465.

Characterization of Compound 58:
IR $v_{max}$ (cm$^{-1}$): 3330, 2219, 1665, 1043; $^1$H NMR (CDCl$_3$, 300 MHz): δ 7.83-7.14 (m, 10H, Ar—H), 6.71 (s, 2H, —NH$_2$), 4.84 (s, 1H, methine), 3.56 (s, 6H, —OCH$_3$), 2.67 (s, 3H, —CH$_3$); LCMS (MM:ES+APCI) (M+H)$^+$ 467.

Characterization of Compound 59:
IR $v_{max}$ (cm$^{-1}$): 3330, 2216, 1648, 1045; $^1$H NMR (CDCl$_3$, 300 MHz): -δ 9.61 (s, 1H, —OH), 7.88-7.09 (m, 10H, Ar—H), 5.86 (s, 2H, —NH$_2$), 4.38 (s, 1H, methine), 3.77 (s, 3H, —OCH$_3$), 2.24 (s, 3H, —CH); LCMS (MM:ES+APCI) (M+H)$^+$ 453.

Characterization of Compound 60:
IR $v_{max}$ (cm$^{-1}$): 3331, 2221, 1670, 1042; $^1$H NMR (CDCl$_3$, 300 MHz): -δ 7.95-7.31 (m, 10H, Ar—H), 6.21 (s, 2H, —NH$_2$), 5.64 (s, 2H, —NH$_2$), 4.81 (s, 1H, methine), 3.68 (s, 3H, —OCH$_3$), 2.24 (s, 3H, —CH$_3$); LCMS (MM:ES+APCI) (M–H)$^-$ 452.

Characterization of Compound 61:
IR $v_{max}$(cm$^{-1}$): 3287, 2197, 1669, 1053; $^1$H NMR (CDCl$_3$, 300 MHz): δ 7.79-7.77 (s, 1H, Ar—H), 7.61-7.57 (m, 2H, Ar—H), 7.35-7.33 (m, 3H, Ar—H), 7.26 (m, 1H, Ar—H), 7.06-7.03 (m, 2H, Ar—H), 6.93-6.90 (m, 2H, Ar—H), 6.84 (m, 11H, Ar—H), 3.81 (s, 1H, Methine), 3.77 (s, 6H —OCH$_3$); $^{13}$C NMR (DMSO-D$_6$, 75 MHz): δ 161.52, 160.25, 154.12, 152.74, 132.13, 126.98, 126.17, 125.01, 124.45, 123.85; 123.11, 122.92, 121.51, 119.25, 116.52, 113.32, 110.59, 100.50, 60.15, 56.72, 55.91, 36.71; LCMS (MM:ES+APCI) (M–H)$^-$ 451.

Characterization of Compound 62:
IR $v_{max}$(cm$^{-1}$): 3330, 2221, 1671, 1052; $^1$H NMR (CDCl$_3$, 300 MHz): δ 7.98-7.26 (m, 10H, Ar—H), 6.53 (s, 2H, —NH$_2$), 4.84 (s, 1H, methine), 3.51 (s, 6H, —OCH$_3$), 2.31 (s, 3H, —CH$_3$); LCMS (MM:ES+APCI) (M+H)$^+$ 467.

Characterization of Compound 63:
IR $v_{max}$(cm$^{-1}$): 3325, 2218, 1671, 1050; $^1$H NMR (CDCl$_3$, 300 MHz): δ 7.95-7.24 (m, 10H, Ar—H), 6.88 (s, 2H, —NH$_2$), 4.41 (s, 1H, methine), 3.78 (s, 3H, —OCH$_3$), 2.41 (m, 2H, —CH$_2$—), 1.83 (t, 3H, —CH$_3$); LCMS (MM:ES+APCI) (M+H)$^+$ 481.

Characterization of Compound 64:
IR $v_{max}$ (cm$^{-1}$): 3328, 2221, 1668, 1045; $^1$H NMR (CDCl$_3$, 300 MHz): δ 7.78-7.11 (m, 10H, Ar—H), 6.67 (s, 2H, —NH$_2$), 4.84 (s, 1H, methine), 3.76 (s, 9H, —OCH$_3$); LCMS (MM:ES+APCI) (M–H)$^-$ 481.

Characterization of Compound 65:
IR $v_{max}$ (cm$^{-1}$): 3325, 2218, 1651, 1053; $^1$H NMR (CDCl$_3$, 300 MHz): -δ 9.58 (s, 1H, —OH), 7.76-7.15 (m, 10H, Ar—H), 5.98 (s, 2H, —NH$_2$), 4.72 (s, 1H, methine), 3.83 (s, 6H, —OCH$_3$); LCMS (MM:ES+APCI) (M+H)$^+$ 469.

Characterization of Compound 66:
IR $v_{max}$ (cm$^{-1}$): 3340, 2219, 1671, 1049; $^1$H NMR (CDCl$_3$, 300 MHz): -δ 7.86-7.33 (m, 10H, Ar—H), 6.09 (s, 2H, —NH$_2$), 5.81 (s, 2H, —NH$_2$), 4.54 (s, 1H, methine), 3.71 (s, 6H, —OCH$_3$); LCMS (MM:ES+APCI) (M+H)$^+$ 468

Characterization of Compound 67:
IR $v_{max}$(cm$^{-1}$): 3301, 2198, 1671, 1053; $^1$H NMR (CDCl$_3$, 300 MHz): -δ 7.92-7.88 (m, 2H, Ar—H), 7.81 (s, 1H, Ar—H), 7.65-7.55 (m, 2H, Ar—H), 7.45-7.32 (m, 3H, Ar—H), 7.25 (m, 2H, Ar—H), 6.98 (s, 1H, Ar—H), 4.29 (s, 1H, Methine), 3.30 (s, 3H, —OCH$_3$); $^{13}$C NMR (CDCl$_3$, 75 MHz) δ 162.19, 161.28, 159.14, 158.34, 133.65, 131.28, 129.52, 125.87, 125.19, 124.57, 124.01, 123.85, 123.08, 122.12, 117.12, 115.28, 103.52, 59.28, 55.71, 36.17; LCMS (MM:ES+APCI) (M+H)+ 491.

Characterization of Compound 68:

IR $v_{max}$ (cm$^{-1}$): 3328, 2215, 1666, 1050; $^1$H NMR (CDCl$_3$, 300 MHz): δ 7.87-7.33 (m, 10H, Ar—H), 5.96 (s, 2H, —NH$_2$), 4.55 (s, 1H, methine), 3.79 (s, 3H, —OCH$_3$), 2.26 (s, 3H, —CH$_3$); LCMS (MM:ES+APCI) (M+H)+ 505.

Characterization of Compound 69:

IR $v_{max}$ (cm$^{-1}$): 3322, 2214, 1677, 1052; $^1$H NMR (CDCl$_3$, 300 MHz): δ 7.88-7.32 (m, 10H, Ar—H), 6.52 (s, 2H, —NH$_2$), 4.51 (s, 1H, methine), 3.67 (s, 3H, —OCH$_3$), 2.38 (m, 2H, —CH$_2$—), 1.65 (t, 3H, —CH$_3$); LCMS (MM:ES+APCI) (M+H)+ 519.

Characterization of Compound 70:

IR $v_{max}$ (cm$^{-1}$): 3330, 2196, 1665, 1042; $^1$H NMR (CDCl$_3$, 300 MHz): δ 7.85-7.09 (m, 10H, Ar—H), 6.77 (s, 2H, —NH$_2$), 4.61 (s, 1H, methine), 3.78 (s, 6H, —OCH$_3$); LCMS (MM:ES+APCI) (M+H)+ 521.

Characterization of Compound 71:

IR $v_{max}$(cm$^{-1}$): 3321, 2220, 1642, 1051; $^1$H NMR (CDCl$_3$, 300 MHz): –δ 9.61 (s. 1H, —OH), 7.76-7.14 (m, 10H, Ar—H), 6.24 (s, 2H, —NH$_2$), 4.51 (s, 1H, methine), 3.77 (s, 3H, —OCH$_3$); LCMS (MM:ES+APCI) (M+H)+ 507.

Characterization of Compound 72:

IR $v_{max}$(cm$^{-1}$): 3335, 2225, 1667, 1041; $^1$H NMR (CDCl$_3$, 300 MHz): –δ 7.94-7.44 (m, 10H, Ar—H), 6.15 (s, 2H, —NH$_2$), 5.33 (s, 2H, —NH$_2$), 4.33 (s, 1H, methine), 3.86 (s, 3H, —OCH$_3$); LCMS (MM:ES+APCI) (M–H)– 504.

Characterization of Compound 73:

IR $v_{max}$ (cm$^{-1}$): 3288, 2198, 1671, 1055; $^1$H NMR (CDCl$_3$, 300 MHz): –δ 7.81-7.79 (d, 1H, Ar—H), 7.63-7.61 (m, 2H, Ar—H), 7.59-7.57 (m, 2H, Ar—H), 7.50 (m, 2H, Ar—H), 7.39-7.51 (m, 2H, Ar—H), 6.86-6.84 (s, 1H, Ar—H), 4.57 (s, 1H, Methine), 3.78 (s, 3H —OCH$_3$); $^{13}$C NMR (DMSO-D$_6$, 75 MHz) δ 161.57, 160.16, 158.91, 144.15, 135.46, 133.48, 132.19, 125.45, 124.89, 124.25, 123.10, 122.59, 121.85, 121.41, 119.32, 116.28, 114.11, 113.42, 101.41, 59.12, 55.72, 36.29; LCMS (MM:ES+APCI) (M–H)– 523.

Characterization of Compound 74:

IR $v_{max}$ (cm$^{-1}$): 3332, 2217, 1658, 1049; $^1$H NMR (CDCl$_3$, 300 MHz): δ 7.76-7.18 (m, 9H, Ar—H), 6.12 (s, 2H, —NH$_2$), 4.90 (s. 1H, methine), 3.78 (s, 3H, —OCH$_3$), 2.31 (s, 3H, —CH$_3$); LCMS (MM:ES+APCI) (M+H)+ 539.

Characterization of Compound 75:

IR $v_{max}$ (cm$^{-1}$): 3335, 2223, 1665, 1041; $^1$H NMR (CDCl$_3$, 300 MHz): δ 7.72-7.05 (m, 9H, Ar—H), 6.35 (s, 2H, —NH$_2$), 4.33 (s, 1H, methine), 3.81 (s, 3H, —OCH$_3$), 2.12 (m, 2H, —CH$_2$—), 1.57 (t, 3H, —CH$_3$); LCMS (MM:ES+APCI) (M+H)+ 553.

Characterization of Compound 76:

IR $v_{max}$ (cm$^{-1}$): 3328, 2226, 1671, 1047; $^1$H NMR (CDCl$_3$, 300 MHz): δ 7.62-6.95 (m, 9H, Ar—H), 6.34 (s, 2H, —NH$_2$), 4.29 (s, 1H, methine), 3.69 (s, 6H, —OCH$_3$); LCMS (MM:ES+APCI) (M–H)– 553.

Characterization of Compound 77:

IR $v_{max}$(cm$^{-1}$): 3316, 2223, 1650, 1044; $^1$H NMR (CDCl$_3$, 300 MHz): –δ 8.75 (s, 1H, —OH), 7.59-6.98 (m, 9H, Ar—H), 5.86 (s, 2H, —NH$_2$), 4.37 (s, 1H, methine), 3.82 (s, 3H, —OCH$_3$); LCMS (MM:ES+APCI) (M+H)+ 541.

Characterization of Compound 78:

IR $v_{max}$ (cm$^{-1}$): 3327, 2217, 1663, 1049; $^1$H NMR (CDCl$_3$, 300 MHz): –δ 7.87-7.35 (m, 9H, Ar—H), 6.08 (s, 2H, —NH$_2$), 5.84 (s, 2H, —NH$_2$), 4.29 (s, 1H, methine), 3.76 (s, 3H, —OCH$_3$); LCMS (MM:ES+APCI) (M+H)+ 540.

Characterization of Compound 79:

IR $v_{max}$ (cm$^{-1}$): 3292, 2199, 1674, 1066; $^1$H NMR (CDCl$_3$, 300 MHz): –δ 8.71 (s, 1H, Pyr-H), 8.60 (s, 1H, Pyr-H), 8.11-7.94 (m, 2H, Pyr-H), 7.81-7.76 (m, 1H, Ar—H), 7.60-7.58 (m, 2H, Ar—H), 7.51-7.31 (m, 4H, Ar—H), 4.62 (s, 1H, Methine), 3.65 (s, 3H —OCH$_3$) LCMS (MM:ES+APCI) (M–H)– 422.

Characterization of Compound 80:

IR $v_{max}$(cm$^{-1}$): 3329, 2217, 1647, 1050; $^1$H NMR (CDCl$_3$, 300 MHz): δ 8.52 (s, 1H, Pyr-H), 8.47-8.25 (m, 3H, Pyr-H), 7.87-7.28 (m, 6H, Ar—H), 6.44 (s, 2H, —NH$_2$), 4.34 (s, 1H, methine), 3.80 (s, 3H, —OCH$_3$), 2.44 (s, 3H, —CH$_3$); LCMS (MM:ES+APCI) (M+H)+ 438.

Characterization of Compound 81:

IR $v_{max}$ (cm$^{-1}$): 3331, 2219, 1663, 1046; $^1$H NMR (CDCl$_3$, 300 MHz): δ 8.55 (s, 1H, Pyr-H), 8.38-8.21 (m, 3H, Pyr-H), 7.89-7.11 (m, 6H, Ar—H), 5.95 (s, 2H, —NH$_2$), 4.61 (s, 1H, methine), 3.67 (s, 3H, —OCH$_3$), 2.25 (m, 2H, —CH$_2$—), 1.62 (t, 3H, —CH$_3$); LCMS (MM:ES+APCI) (M+H)+ 452.

Characterization of Compound 82:

IR $v_{max}$(cm$^{-1}$): 3331, 2219, 1665, 1039; $^1$H NMR (CDCl$_3$, 300 MHz): δ 8.62 (s, 1H, Pyr-H), 8.33-8.15 (m, 3H, Pyr-H), 7.99-7.20 (m, 6H, Ar—H), 6.52 (s, 2H, —NH$_2$), 4.26 (s, 1H, methine), 3.71 (s, 6H, —OCH$_3$); LCMS (MM:ES+APCI) (M+H)+ 454.

Characterization of Compound 83:

IR $v_{max}$ (cm$^{-1}$): 3320, 2217, 1651, 1048; $^1$H NMR (CDCl$_3$, 300 MHz): –δ 9.32 (s, 1H, —OH), 8.67 (s, 1H, Pyr-H), 8.41-8.26 (m, 3H, Pyr-H), 7.84-7.16 (m, 6H, Ar—H), 6.41 (s, 2H, —NH$_2$), 4.51 (s, 1H, methine), 3.77 (s, 3H, —OCH$_3$); LCMS (MM:ES+APCI) (M–H)– 439.

Characterization of Compound 84:

IR $v_{max}$(cmi): 3325, 2214, 1670, 1050; $^1$H NMR (CDCl$_3$, 300 MHz): –δ 8.59 (s, 1H, Pyr-H), 8.39-8.11 (m, 3H, Pyr-H), 7.92-7.21 (m, 6H, Ar—H), 6.24 (s, 2H, —NH$_2$), 5.65 (s, 2H, —NH$_2$), 4.31 (s, 1H, methine), 3.59 (s, 3H, —OCH$_3$); LCMS (MM:ES+APCI) (M+H)+ 439.

Characterization of Compound 85:

IR $v_{max}$: 3228 cm$^{-1}$ $v_{(NH2)}$, 2193 cm$^{-1}$ $v_{(CN)}$, 1671 cm$^{-1}$ $v_{(C-O)}$, 1051 cm$^{-1}$ $v_{(C=O)}$; $^1$H NMR (CDCl$_3$, 300 MHz): –δ 8.60 (s, 1H, Ar—N—CH), 7.71-7.18 (m, 8H, Ar—H), 4.11 (s, 1H, Methine), 3.60 (s, 3H, —OCH$_3$); LCMS (MM:ES+APCI) (M+H)+ 493.

Characterization of Compound 86:

IR $v_{max}$ (cm$^{-1}$): 3331, 2222, 1639, 1042; $^1$H NMR (CDCl$_3$, 300 MHz): δ 8.88 (s, 1H, Pyr-H), 8.67 (s, 1H, Pyr-H), 7.72-7.25 (m, 6H, Ar—H), 6.61 (s, 2H, —NH$_2$), 4.56 (s, 1H, methine), 3.77 (s, 3H, —OCH$_3$), 2.39 (s, 3H, —CH$_3$); LCMS (MM:ES+APCI) (M+H)+ 506.

Characterization of Compound 87:

IR $v_{max}$(cm$^{-1}$): 3329, 2217, 1658, 1045; $^1$H NMR (CDCl$_3$, 300 MHz): δ 8.72 (s, 1H, Pyr-H), 8.48 (s, 1H, Pyr-H), 7.48-7.05 (m, 6H, Ar—H), 6.11 (s, 2H, —NH$_2$), 4.90 (s, 1H, methine), 3.82 (s, 3H, —OCH$_3$), 2.42 (m, 2H, —CH$_2$—), 1.77 (t, 3H, —CH$_3$); LCMS (MM:ES+APCI) (M−H)$^-$ 518.

Characterization of Compound 88:

IR $v_{max}$ (cm$^{-1}$): 3329, 2226, 1670, 1049; $^1$H NMR (CDCl$_3$, 300 MHz): δ 8.90 (s, 1H, Pyr-H), 8.56 (s, 1H, Pyr-H), 7.84-7.37 (m, 6H, Ar—H), 6.70 (s, 2H, —NH$_2$), 4.35 (s, 1H, methine), 3.84 (s, 6H, —OCH$_3$); LCMS (MM:ES+APCI) (M+H)$^+$ 522.

Characterization of Compound 89:

IR $v_{max}$(cm$^{-1}$): 3320, 2217, 1651, 1048; $^1$H NMR (CDCl$_3$, 300 MHz): -δ 9.50 (s, 1H, —OH), 8.88 (s, 1H, Pyr-H), 8.57 (s, 1H, Pyr-H), 7.75-7.06 (lm, 6H, Ar—H), 5.92 (s, 2H, —NH$_2$), 4.33 (s, 1H, methine), 3.69 (s, 3H, —OCH$_3$); LCMS (MM:ES+APCI) (M+H)$^+$ 508.

Characterization of Compound 90:

IR $v_{max}$ (cm$^{-1}$): 3323, 2219, 1668, 1049; $^1$H NMR (CDCl$_3$, 300 MHz): -δ 8.62 (s, 1H, Pyr-H), 8.45 (s, 1H, Pyr-H), 7.89-7.25 (m, 6H, Ar—H), 6.30 (s, 2H, —NH$_2$), 5.98 (s, 2H, —NH$_2$), 4.31 (s, 1H, methine), 3.83 (s, 3H, —OCH$_3$); LCMS (MM:ES+APCI) (M+H)$^+$ 507.

Characterization of Compound 91:

IR $v_{max}$ (cm$^{-1}$): 3292, 2199, 1674, 1066; $^1$H NMR (CDCl$_3$, 300 MHz): -δ 9.79 (s, 2H, —NH$_2$), 8.015-7.043 (m, 9H, Ar—H), 4.688 (s, 1H, Methine), 3.855 (s, 3H, —CH$_3$), 2.251 (s, 3H, —CH$_3$); $^{13}$C NMR (DMSO-D$_6$, 75 MHz) δ 161.21, 160.45, 158.51, 157.28, 155.19, 135.28, 134.91, 132.36, 129.85, 128.71, 125.26, 124.92, 123.31, 122.82, 120.85, 117.28, 115.11, 113.28, 105.21, 59.28, 51.11, 35.12, 15.86; LCMS (MM:ES+APCI) (M+H)$^+$ 456.

Characterization of Compound 92:

IR $v_{max}$ (cm$^{-1}$): 3328, 2218, 1640, 1039; $^1$H NMR (CDCl$_3$, 300 MHz): δ 8.57 (s, 1H, Pyr-H), 7.83-7.29 (m, 6H, Ar—H), 6.82 (s, 2H, —NH$_2$), 4.35 (s, 1H, methine), 3.81 (s, 3H, —OCH$_3$), 2.42 (s, 3H, —CH$_3$); LCMS (MM:ES+APCI) (M+H)$^+$ 470.

Characterization of Compound 93:

IR $v_{max}$ (cm$^{-1}$): 3331, 2220, 1663, 1051; $^1$H NMR (CDCl$_3$, 300 MHz): δ 8.59 (s, 1H, Pyr-H) 7.68-7.16 (m, 6H, Ar—H), 6.23 (s, 2H, —NH$_2$), 4.85 (s, 1H, methine), 3.59 (s, 3H, —OCH$_3$), 2.33 (m, 2H, —CH$_2$—), 1.86 (t, 3H, —CH$_3$); LCMS (MM:ES+APCI) (M+H)$^+$ 484.

Characterization of Compound 94:

IR $v_{max}$(cm$^{-1}$): 3331, 2229, 1669, 1051; $^1$H NMR (CDCl$_3$, 300 MHz): δ 8.78 (s, 1H, Pyr-H), 7.58-7.22 (m, 6H, Ar—H), 6.52 (s, 2H, —NH$_2$), 4.48 (s, 1H, methine), 3.72 (s, 6H, —OCH$_3$); LCMS (MM:ES+APCI) (M+H)$^+$ 486

Characterization of Compound 95:

IR $v_{max}$ (cm$^{-1}$): 3318, 2221, 1662, 1050; $^1$H NMR (CDCl$_3$, 300 MHz): -δ 9.41 (s, 1H, —OH), 8.59 (s, 1H, Pyr-H) 7.66-7.03 (m, 6H, Ar—H), 6.41 (s, 2H, —NH$_2$), 4.52 (s, 1H, methine), 3.74 (s, 3H, —OCH$_3$); LCMS (MM:ES+APCI) (M−H)$^-$ 470.

Characterization of Compound 96:

IR $v_{max}$ (cm$^{-1}$): 3331, 2220, 1670, 1052; $^1$H NMR (CDCl$_3$, 300 MHz): -δ 8.78 (s, 1H, Pyr-H), 7.76-7.33 (m, 6H, Ar—H), 5.91 (s, 2H, —NH$_2$), 5.21 (s, 2H, —NH$_2$), 4.52 (s, 1H, methine), 3.80 (s, 3H, —OCH$_3$); LCMS (MM:ES+APCI) (M+H)$^+$ 471.

General Synthetic Protocol 3

Synthetic procedure to provide Compounds of Formula G (Subset of Compounds of Formula (I))

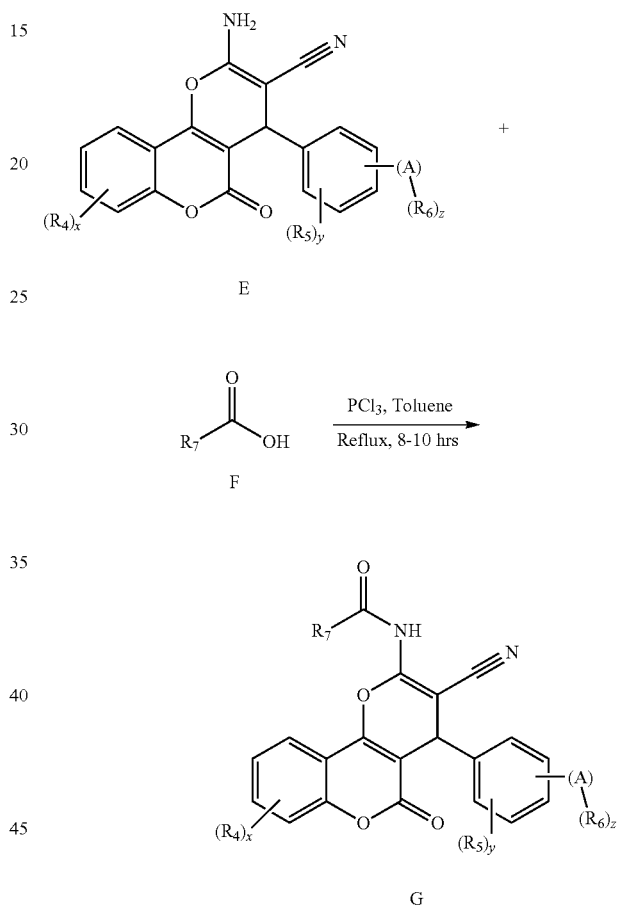

Scheme 2: Compounds of Formula G were obtained from acid-amine coupling reaction of Compounds of Formula E with various substituted aryl/hetero aryl carboxylic acids of Formula F. R$_4$, R$_5$, R$_6$, R$_7$, (A), x, y and z correspond to the groups mentioned in the compound of Formula (I) as disclosed hereinbefore.

The Compounds of Formula G were prepared by the reaction of Compounds of Formula E (1 eq) with various substituted aryl/hetero aryl carboxylic acids (1 eq; Compounds of Formula F). The reaction was carried out in toluene and phosphorous trichloride (1 eq) for 8-10 hrs, at 110° C. Formation of product was monitored by TLC. After the reaction was considered complete, the reaction mixture was treated with 10% NaHCO$_3$ (2×10 ml), distilled water (15 ml) and the product was extracted into ethyl acetate layer and this organic layer was vacuum evaporated to provide the pure product without need for further purification.

Example 2: Compounds 97-106

Compounds 97-106 were prepared following General Synthetic Protocol 3 above. The compounds made, and their starting materials, are outlined in Table 3 below.

TABLE 3

| Starting Material (Compound of Formula E) | Carboxylic acid (F) | Compounds 97-106 (Compound of Formula G/(I)) |
|---|---|---|

TABLE 3-continued
| Starting Material (Compound of Formula E) | Carboxylic acid (F) | Compounds 97-106 (Compound of Formula G/(I)) |
|---|---|---|
| | 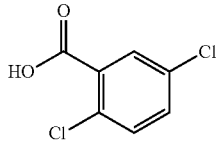 [SMILES: O=C(O)c1cc(Cl)ccc1Cl] | 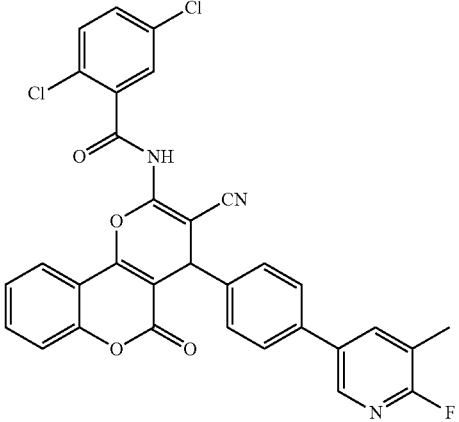
100 |
| | 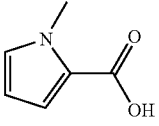 | 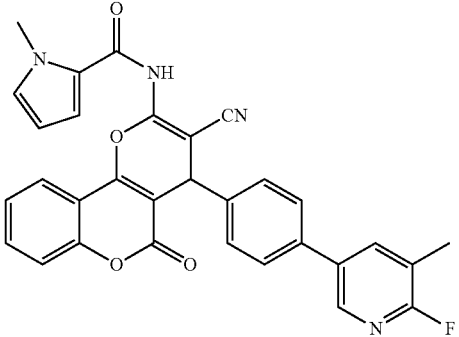
101 |
| 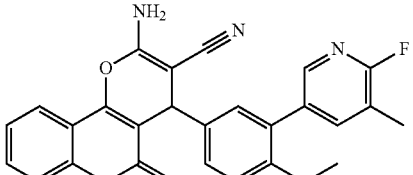 | 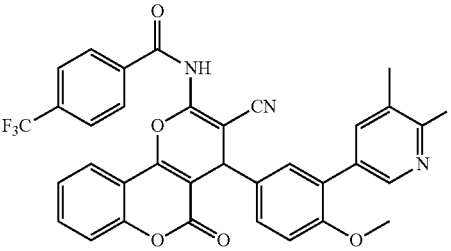 | 
102 |

TABLE 3-continued
| Starting Material (Compound of Formula E) | Carboxylic acid (F) | Compounds 97-106 (Compound of Formula G/(I)) |
|---|---|---|
| | 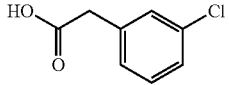 [SMILES: O=C(O)Cc1cccc(Cl)c1] | 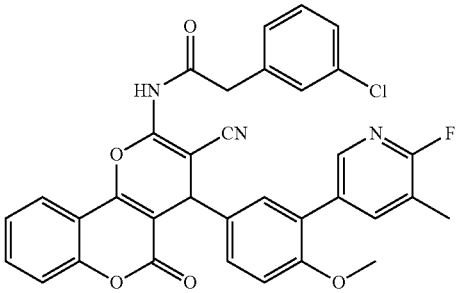<br>103 |
| | 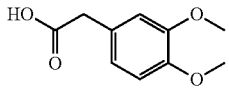 | 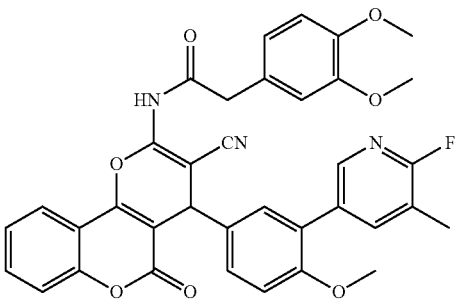<br>104 |
| | 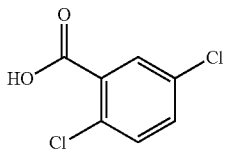 | 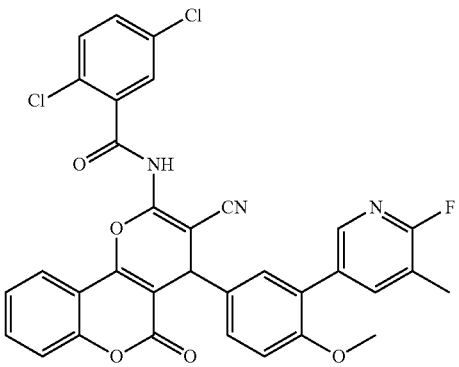<br>105 |
| | 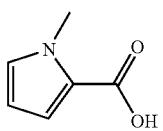 | 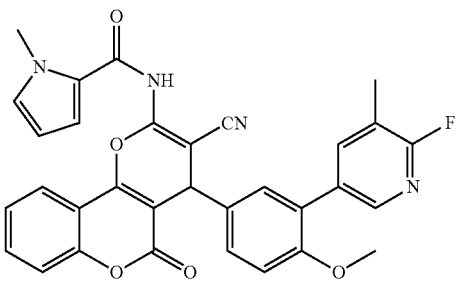<br>106 |

Characterization of Compound 97:

IR $v_{max}$ (cm$^{-1}$): 3280, 2210, 1662, 1055; $^1$H NMR (DMSO-D$_6$, 400 MHz): –δ 9.36 (s, 1H, —NH—), 8.35 (s, 1H, Py-H), 7.98 (s, 1H, Ar—H), 7.41-7.38 (m, 2H, Ar—H), 7.30-7.20 (m, 4H, Ar—H), 7.11-6.97 (m, 2H, Ar—H), 6.86-6.77 (m, 4H, Ar—H), 3.96 (s, 1H, Methine), 2.47 (s, 3H, —CH$_3$); $^{13}$C NMR (DMSO-D$_6$, 100 MHz) δ 167.54, 166.19, 163.88, 163.64, 153.90, 143.81, 135.99, 135.96, 131.59, 131.41, 129.51, 129.42, 129.32, 129.24, 124.76, 124.65, 124.47, 124.28, 116.54, 116.17, 116.05, 115.94, 115.84, 110.72, 110.60, 110.53, 58.35, 43.51, 14.45; LCMS (MM:ES+APCI) (M-H)$^-$ 596.

Characterization of Compound 98:

IR $v_{max}$ (cm$^{-1}$): 3291, 2225, 1658, 1049; $^1$H NMR (CDCl$_3$, 300 MHz): –δ 9.56 (s, 1H, —NH—), 8.38 (s, 1H, Py-H), 8.29 (s, 1H, Py-H), 8.15-7.98 (m, 2H, Ar—H), 7.87-7.65 (m, 2H, Ar—H), 7.50-7.11 (m, 3H, Ar—H), 7.03 (s, 1H, Ar—H), 6.98-6.75 (m, 4H, Ar—H), 5.03 (s, 1H, Mathine), 3.87 (s, 2H, —CH$_2$—), 2.46 (s, 3H, —CH$_3$); LCMS (MM:ES+APCI) (M+H)$^+$ 578.

Characterization of Compound 99:

IR $v_{max}$(cm$^{-1}$): 3310, 2210, 1665, 1048; $^1$H NMR (CDCl$_3$, 300 MHz): –δ 9.63 (s, 1H, —NH—), 8.58 (s, 1H, Py-H), 8.40 (s, 1H, Py-H), 8.33-8.19 (m, 2H, Ar—H), 8.06-7.88 (m, 2H, Ar—H), 7.61-7.33 (m, 4H, Ar—H), 7.21 (s, 1H, Ar—H), 7.09 (s, 1H, Ar—H), 4.97 (s, 1H, Methine), 3.85 (s, 2H, Methylene), 3.76 (s, 6H, Methoxy), 2.44 (s, 3H, Methyl); LCMS (MM:ES+APCI) (M+H)$^+$ 604.

Characterization of Compound 100:

IR $v_{max}$ (cm$^{-1}$): 3328, 2221, 1665, 1042; $^1$H NMR (CDCl$_3$, 300 MHz): –δ 9.79 (s, 1H, —NH—), 8.38 (s, 1H, Py-H), 8.11 (s, 1H, Py-H), 8.02-7.97 (m, 3H, Ar—H), 7.81-7.50 (m, 4H, Ar—H), 7.38-7.04 (m, 4H, Ar—H), 5.08 (s, 1H, Methine), 2.31 (s, 3H, Methyl); LCMS (MM:ES+APCI) (M+H)$^+$ 599.

Characterization of Compound 101:

IR $v_{max}$(cm$^{-1}$): 3330, 2225, 1669, 1043; $^1$H NMR (CDCl$_3$, 300 MHz): –δ 10.01 (s, 1H, —NH—), 8.45 (s, 1H, Py-H), 8.22 (s, 1H, Py-H), 8.13-7.97 (m, 2H, Ar—H), 7.85-7.63 (m, 3H, Ar—H), 7.52-7.34 (m, 2H, Pyl-H), 7.19-6.92 (m, 3H, Ar—H), 6.77 (m, 1H, Ar—H), 5.19 (s, 1H, Methine), 3.94 (s, 3H, Pyl-Methyl), 2.36 (s, 3H, Methyl); LCMS (MM:ES+APCI) (M+H)$^+$ 533.

Characterization of Compound 102:

IR $v_{max}$: 3290, 2195, 1670, 1068; $^1$H NMR (DMSO-D$_6$, 400 MHz): –δ 9.76 (s, 1H, —NH—), 8.05 (s, 1H, Py-H), 7.69 (s, 1H, Py-H), 7.48-7.43 (m, 3H, Ar—H), 7.34 (m, 1H, Ar—H), 7.23-7.19 (m, 4H, Ar—H), 7.06-7.03 (m, 2H, Pyl-H), 6.32 (s, 1H, Ar—H), 4.32 (s, 1H. Methine), 3.87 (s, 3H, Pyl-Methyl), 2.47 (s, 3H, Methyl); $^{13}$C NMR (DMSO-D$_6$, 100 MHz) 167.08, 164.00, 161.30, 158.17, 152.95, 148.80, 147.32, 145.58, 143.23, 138.38, 137.09, 134.50, 128.27, 129.10, 125.01, 124.80, 123.73, 123.67, 122.08, 121.99, 121.01, 120.36, 115.91, 113.11, 111.00, 108.31, 62.13, 43.99, 36.11, 17.35; LCMS (MM:ES+APCI) (M+H)$^+$ 533.

Characterization of Compound 103:

IR $v_{max}$: 3320, 2225, 1670, 1068; $^1$H NMR (CDCl$_3$, 300 MHz): –δ 9.86 (s, 1H, —NH—), 8.55 (s, 1H, Py-H), 8.39 (s, 1H, Py-H), 8.12 (s, 1H, Ar—H), 7.95-7.74 (m, 4H, Ar—H), 7.60-7.35 (m, 4H, Ar—H), 7.22-7.03 (m, 2H, Ar—H), 4.87 (s, 1H, Methine), 3.82 (s, 2H, Methylene), 3.76 (s, 3H, Methoxy), 2.36 (s, 3H, Methyl); LCMS (MM:ES+APCI) (M+H)$^+$ 609.

Characterization of Compound 104:

IR $v_{max}$: 3321, 2229, 1668, 1055; $^1$H NMR (CDCl$_3$, 300 MHz): –δ 9.79 (s, 1H, —NH—), 8.49 (s, 1H, Py-H), 8.31 (s, 1H, Py-H), 8.21 (s, 1H, Ar—H), 7.98-7.70 (m, 4H, Ar—H), 7.35-7.19 (m, 2H, Ar—H), 6.89 (s, 1H, Ar—H), 6.51 (s, 2H, Ar—H), 4.91 (s, 1H, Methine), 3.90 (s, 2H, Methylene), 3.84 (s, 3H, Methoxy), 3.79 (s, 3H, Methoxy), 2.40 (s, 3H, Methyl).

Characterization of Compound 105:

IR $v_{max}$: 3330, 2221, 1670, 1042; $^1$H NMR (CDCl$_3$, 300 MHz): –δ 10.08 (s, 1H, —NH—), 8.35 (s, 1H, Py-H), 8.11 (s, 1H, Py-H), 8.03 (s, 1H, Ar—H), (m, 2H, Ar—H), 7.85 (s, 1H, Ar—H), 7.74-7.59 (m, 2H, Ar—H), 7.43-7.22 (m, 4H, Ar—H), 7.11-6.97 (m, 2H, Ar—H), 4.89 (s, 1H, Methine), 3.81 (s, 3H, Methoxy), 2.35 (s, 3H, Methyl).

Characterization of Compound 106:

IR $v_{max}$: 3329, 2225, 1665, 1049; $^1$H NMR (CDCl$_3$, 300 MHz): –δ 9.75 (s, 1H, —NH—), 8.49 (s, 1H, Py-H), 8.26 (s, 1H, Py-H), 8.12 (s, 1H, Ar—H), 7.95-7.78 (m, 3H, Ar—H), 7.63-7.41 (m, 3H, Ar—H), 7.20-7.06 (m, 3H, Ar—H), 5.12 (s, 1H, Methine), 3.89 (s, 3H, N-Methyl), 3.76 (s, 3H, Methoxy), 2.46 (s, 3H, Methyl); LCMS (MM:ES+APCI) (M+H)$^+$ 563.

General Synthetic Protocol 4

Synthetic Procedure to Provide Compounds of Formula J (Subset of Compounds of Formula (I))

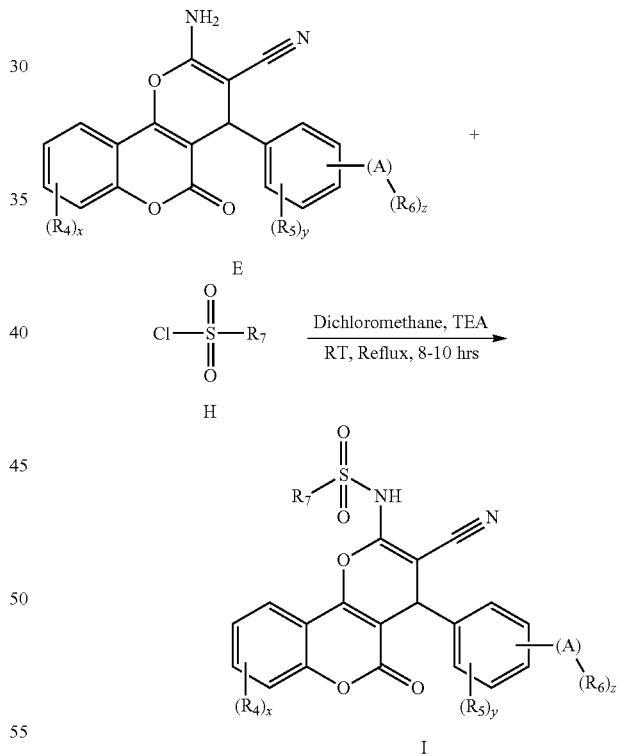

Synthetic Scheme 3

Scheme 3: The sulphonyl chloride-amine coupling reaction of Compounds of formula E with various substituted aryl/hetero aryl sulfonylchlorides (compounds of formula H) resulted in the formation of the compounds of formula J. R$_4$, R$_5$, R$_6$, R$_7$, (A), x, y and z correspond to the groups mentioned in the compound of Formula (i) as disclosed hereinbefore.

The Compounds of Formula J (a subset of the compounds of Formula (I)) were prepared by the reaction of Compounds of Formula E (1 eq) with reacting various substituted aryl sulphonyl chlorides (1.2 eq; Compounds of Formula H). The reaction was carried out in dichloromethane solvent and triethyl amine for 8-10 hrs at room temperature. Formation of product was monitored by TLC. After the reaction was considered complete by TLC, the reaction mixture was treated with 10% HCl (2×10 ml), distilled water (15 ml) and the product was extracted to ethyl acetate layer and the organic layer was vacuum evaporated to provide the pure product without further need for purification.

Example 3: Compounds 107-112

Compounds 107-112 were prepared following General Synthetic Protocol 4 above. The compounds made, and their starting materials, are outlined in Table 4 below.

TABLE 4

| Compounds of Formula E | Aryl sulphonyl chloride (H) | Compounds 107-112 (Compounds of Formula J/(I)) |
|---|---|---|
| 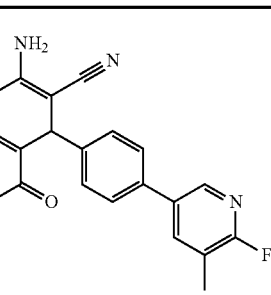 | 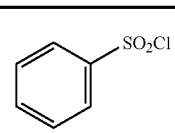 | 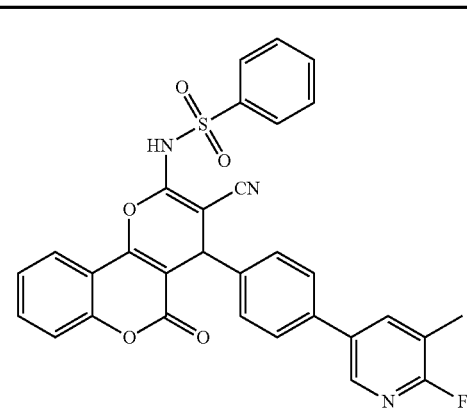 107 |
| | 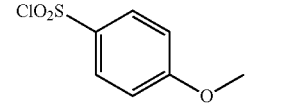 | 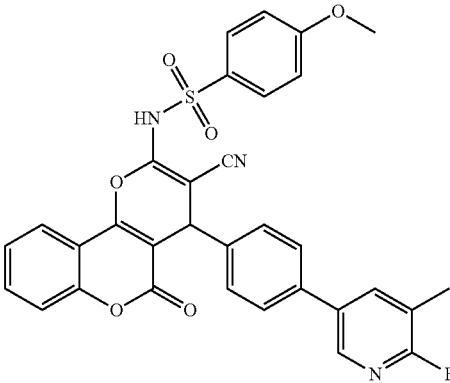 108 |

TABLE 4-continued
| Compounds of Formula E | Aryl sulphonyl chloride (H) | Compounds 107-112 (Compounds of Formula J/(I)) |
|---|---|---|
| | 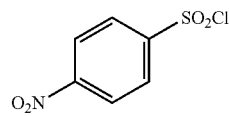 [SMILES: O=[N+]([O-])c1ccc(S(=O)(=O)Cl)cc1] | 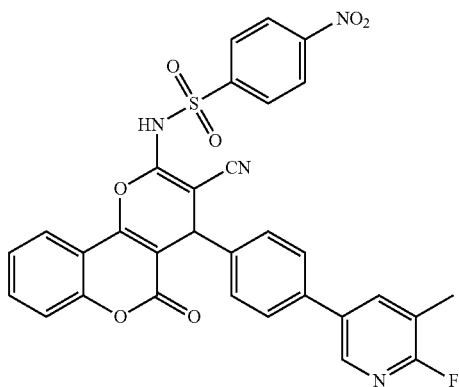 109 |
| 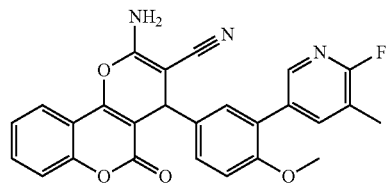 [SMILES: COc1ccc(C2C(C#N)=C(N)Oc3c2c(=O)oc2ccccc32)cc1-c1cnc(F)c(C)c1] | 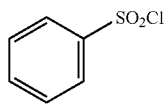 | 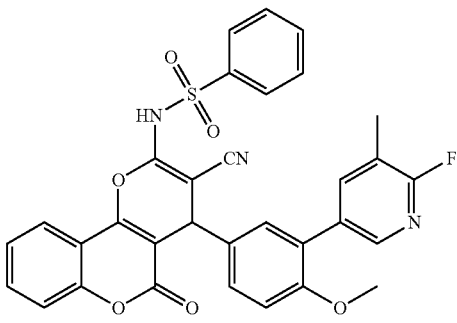 110 |

| Compounds of Formula E | Aryl sulphonyl chloride (H) | Compounds 107-112 (Compounds of Formula J/(I)) |
|---|---|---|
| | 4-methoxybenzenesulfonyl chloride | Compound 111 |
| | 4-nitrobenzenesulfonyl chloride | Compound 112 |

Characterization of Compound 107:

¹H NMR (CDCl$_3$, 300 MHz): −δ 8.69 (s, 1H, Py-H): 8.37 (s, 1H, Py-H), 8.11-7.98 (m, 4H, Ar—H), 7.85-7.63 (m, 5H, Ar—H), 7.51-7.22 (m, 4H, Ar—H), 7.03 (s, 1H, —NH—), 5.12 (s, 1H, Methine), 2.41 (s, 3H, Methyl); ¹³C NMR (CDCl$_3$, 75 MHz) δ 163.25, 159.12, 158.69, 153.48, 149.62, 145.59, 139.54, 136.39, 134.11, 131.97, 130.05, 129.15, 128.68, 127.16, 126.02, 125.95, 125.18, 123.88, 123.32, 122.76, 122.05, 120.15, 118.91, 116.52, 113.86, 106.91, 60.51, 43.17, 14.55; LCMS (MM:ES+APCI) (M+H)$^+$ 566.

Characterization of Compound 108:

¹H NMR (CDCl$_3$, 300 MHz): −δ 8.53 (s, 1H, Py-H), 8.21 (s, 1H, Py-H), 8.07-7.83 (m, 4H, Ar—H), 7.70-7.49 (m, 4H, Ar—H), 7.31-7.10 (m, 4H, Ar—H), 6.98 (s, 1H, —NH—), 4.97 (s, 1H, Methine), 3.85 (s, 3H, Methoxy), 2.31 (s, 3H, Methyl); LCMS (MM:ES+APCI) (M+H)$^+$ 596.

Characterization of Compound 109:

¹H NMR (CDCl$_3$, 300 MHz): −δ 8.29 (s, 1H, Py-H), 8.08 (s, 1H, Py-H), 7.96-7.74 (m, 4H, Ar—H), 7.61-7.38 (m, 4H, Ar—H), 7.27-7.03 (m, 4H, Ar—H), 6.89 (s, 1H, —NH—), 4.99 (s, 1H, Methine), 2.48 (s, 3H, Methyl).

Characterization of Compound 110:

¹H NMR (CDCl$_3$, 300 MHz): −δ 8.35 (s, 1H, Py-H), 8.18 (s, 1H, Py-H), 8.03 (s, 1H, Ar—H), 7.91-7.78 (m, 3H, Ar—H), 7.62-7.44 (m, 3H, Ar—H), 7.25-7.12 (m, 3H, Ar—H), 7.08-6.93 (m, 2H, Ar—H), 6.87 (s, 1H, —NH—), 5.10 (s, 1H, Methine), 3.80 (s, 3H, Methoxy), 2.35 (s, 3H, Methyl); LCMS (MM:ES+APCI) (M+H)$^+$ 596

Characterization of Compound 111:

¹H NMR (CDCl$_3$, 300 MHz): −δ 8.33 (s, 1H, Py-H), 8.18 (s, 1H, Py-H), 8.01 (s, 1H, Ar—H), 7.93-7.80 (m, 4H, Ar—H), 7.67-7.38 (m, 4H, Ar—H), 7.26-7.11 (m, 2H, Ar—H), 7.05 (s, 1H, —NH—), 4.91 (s, 1H, Methine), 3.83 (s, 3H, Methoxy), 2.56 (s, 3H, Methyl).

Characterization of Compound 112:

¹H NMR (CDCl$_3$, 300 MHz): −δ 8.47 (s, 1H, Py-H), 8.23 (s, 1H, Py-H), 8.08 (s, 1H, Ar—H), 7.90-7.76 (m, 4H, Ar—H), 7.61-7.31 (m, 4H, Ar—H), 7.20-7.05 (m, 2H, Ar—H), 6.93 (s, 1H, —NH—), 5.17 (s, 1H, Methine), 3.78 3.79 (s, 6H, Methoxy), 2.46 (s, 3H, Methyl).

General Synthetic Protocols 5-7

Synthetic Procedure to Provide Compounds of Formula K, M and N (Subset of Compounds of Formula (I))

Synthetic Scheme 4 is detailed below. Compounds of Formulae K, M and N were obtained by a series of reactions as shown using procedures in Scheme 4. $R_4$, $R_5$, $R_6$, (A), x, y and z correspond to the groups mentioned in the compound of Formula (I) as disclosed hereinbefore. R* (when present) corresponds to a substituent or substituents as disclosed in relation to corresponding compounds of Formula (I).

Scheme 4

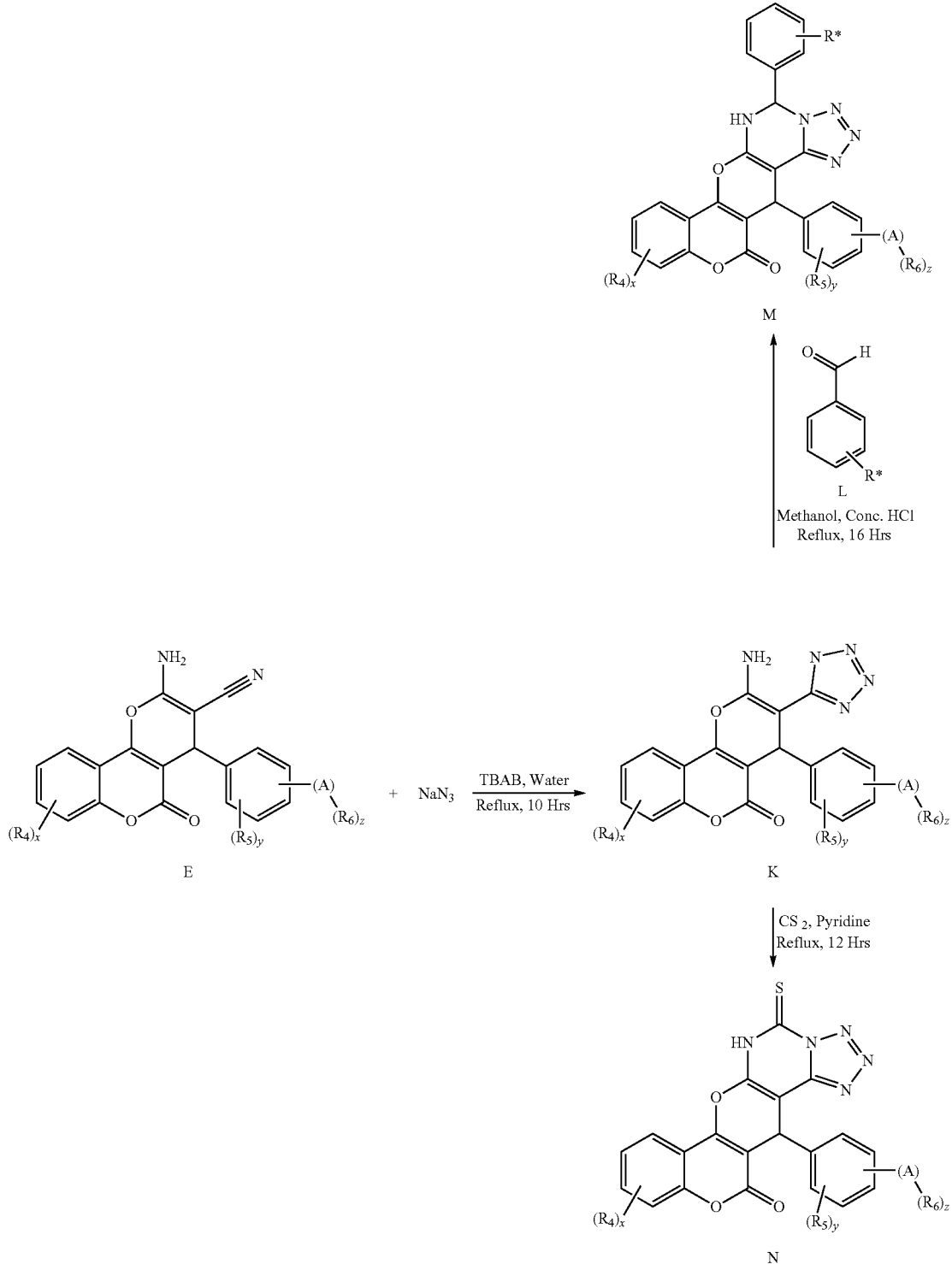

General Protocol 5

Compounds of Formula K were prepared by the reaction of a Compound of Formula E (1 eq) with sodium azide (1.2 eq) and TBAB (0.8 eq) in water. The reaction mixture was refluxed for 10-12 hrs. Formation of product was monitored by TLC. After the reaction was considered complete, the reaction mixture was cooled and a precipitate was obtained that was filtered off, washed and dried to provide the desired compound.

General Protocol 6 Compounds of Formula M were obtained by refluxing a compound of Formula K (1.0 eq) with an aromatic aldehyde (1.0 eg; Compounds of Formula L) in the presence of concentrated hydrochloric acid and methanol solvent for 16 hours. Formation of product was monitored by TLC. After the reaction was considered complete, the reaction mixture was cooled and a precipitate was obtained that was filtered off, washed and dried to provide the desired compound.

General Protocol 6 Compounds of Formula N were obtained by heating compound K (1.0 eq) with carbon disulfide (1.2 eq) in pyridine for 16 hrs. After completion of the reaction (monitored by TLC), the reaction mixture was cooled then poured into ice water and neutralized with dil. HCl, whereupon a precipitate was obtained that was filtered off, washed and dried to provide the desired compound.

Example 4: Compounds 113-114

Compounds 113-114 were prepared following General Synthetic Protocol 5 above. The compounds made, and their starting materials, are outlined in Table 5 below.

TABLE 5

| Compounds of Formula E | Compounds 113 and 114 (Compounds of Formula K/(I)) |
|---|---|
| 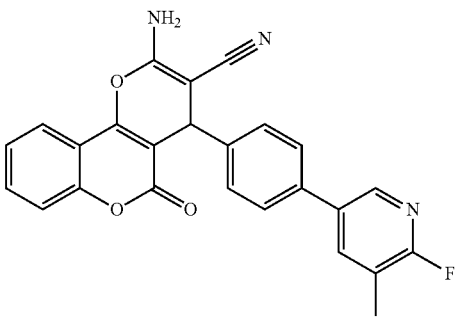 [SMILES: Cc1cc(-c2ccc(C3C(C#N)=C(N)Oc4c3c(=O)oc3ccccc43)cc2)cnc1F] | 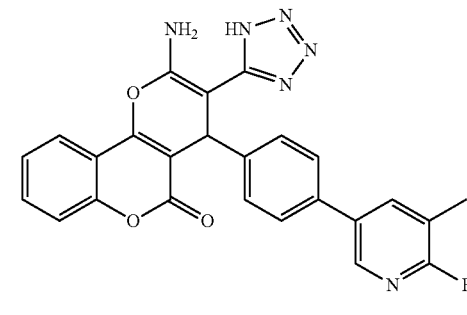113 |
| 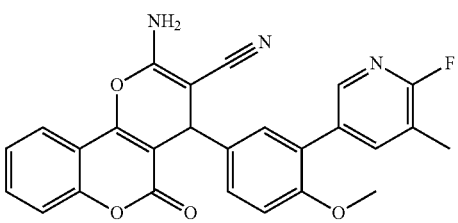 [SMILES: COc1ccc(C2C(C#N)=C(N)Oc3c2c(=O)oc2ccccc32)cc1-c1cnc(F)c(C)c1] | 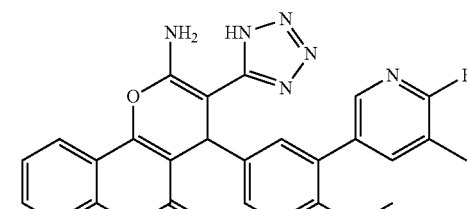114 |

Characterization of Compound 113:
$^1$H NMR (CDCl$_3$, 300 MHz): −δ 10.11 (s, 1H, Tet-NH—), 8.55 (s, 1H, Py-H), 8.38 (s, 1H, Py-H), 8.03-7.82 (m, 4H, Ar—H), 7.77-7.41 (m, 4H, Ar—H), 6.33 (s, 2H, —NH$_2$), 5.04 (s, 1H, Methine), 2.41 (s, 3H, Methyl); $^{13}$C NMR (CDCl$_3$, 75 MHz) δ 162.38, 160.19, 159.01, 156.74, 151.25, 145.64, 141.22, 138.94, 135.69, 133.42, 132.34, 128.95, 127.83, 126.74, 124.54, 122.33, 118.97, 114.54, 113.49, 104.51, 88.70, 34.26, 13.48; LCMS (MM:ES+APCI) (M+H)$^+$ 469.

Characterization of Compound 114:
$^1$H NMR (CDCl$_3$, 300 MHz): −δ 9.83 (s, 1H, Tet-NH—), 8.28 (s, 1H, Py-H), 8.11 (s, 1H, Py-H), 7.98 (s, 1H, Ar—H), 7.86-7.59 (m, 4H, Ar—H), 7.30-7.14 (m, 2H, Ar—H), 6.41 (s, 2H, NH$_2$), 4.05 (s, 1H, Methine), 3.79 (s, 3H, —CH$_3$), 2.46 (s, 3H, —CH$_3$); LCMS (MM:ES+APCI) (M+H)$^+$ 499.

Example 5: Compounds 115-118

Compounds 115-118 were prepared following General Synthetic Protocol 6 above. The compounds made, and their starting materials, are outlined in Table 6 below.

TABLE 6

| Compound of Formula K | Aldehyde (L) | Compounds 115-118 (Compounds of Formula M/(I)) |
|---|---|---|
| (structure) | (structure) | (structure) 115 |
| (structure) | (structure) | (structure) 116 |

TABLE 6-continued

| Compound of Formula K | Aldehyde (L) | Compounds 115-118 (Compounds of Formula M/(I)) |
|---|---|---|
| (structure) | (structure) | 117 |
| (structure) | (structure) | 118 |

Characterization of Compound 115:

$^1$H NMR (CDCl$_3$, 400 MHz): –δ 8.55 (s, 1H, Py-H), 7.84-7.82 (d, 1H, Ar—H), 7.65-7.61 (m, 1H, Ar—H), 7.42-7.23 (m, 11H, Ar—H) 6.11 (s, 1H, Meyhine), 5.14 (s, 1H, Methyne), 2.41 (s, 3H, Methyl), 2.1 (s, 1H, NH); $^{13}$C NMR (CDCl$_3$, 100 MHz) δ 163.8, 161.9, 157.4, 152.5, 146.4, 142.2, 139.4, 138.6, 136.9, 134.2, 133.4, 129.5, 128.5, 128.3, 128.3, 126.9, 126.7, 125.4, 123.3, 120.8, 119.1, 116.4, 105.3, 87.0, 78.2, 32.9, 13.8; LCMS (MM:ES+APCI) (M+H)$^+$ 557.8.

Characterization of Compound 116:

$^1$H NMR (CDCl$_3$, 400 MHz): –δ 8.61 (s, 1H, Py-H), 8.39 (s. 1H, Py-H), 8.34 (s, 1H, Ar—H), 7.86-7.84 (d, 1H, Ar—H), 7.64-7.60 (m, 1H, Ar—H), 7.43-7.23 (m, 10H, Ar—H) 6.14 (s, 1H, Meyhine), 5.16 (s, 1H, Methyne), 3.84 (s, 3H, Metoxy), 2.42 (s, 3H, Methyl), 2.1 (s, 1H, NH): LCMS (MM:ES+APCI) (M+H)$^+$ 587.2.

Characterization of Compound 117:

$^1$H NMR (CDCl$_3$, 400 MHz): –δ 8.64 (s, 1H, Py-H), 8.32 (s, 1H, Ar—H), 7.84-7.82 (d, 1H, Ar—H), 7.68-7.65 (m, 2H, Ar—H), 7.40-7.21 (m, 7H, Ar—H), 7.08-7.05 (m, 1H, Ar—H), 6.93-6.89 (m, 1H, Ar—H), 6.10 (s, 1H, Meyhine), 5.11 (s, 1H, Methyne), 3.84 (S, 3H), 2.39 (s, 3H, Methyl), 2.1 (s, 1H, NH); $^{13}$C NMR (CDCl$_3$, 100 MHz) δ 163.8, 160.1, 157.4, 152.1, 145.9, 139.4, 139.1, 136.2, 134.1, 132.9, 130.0, 128.5, 128.3, 126.9, 125.7, 125.4, 123.3, 120.8, 119.1, 116.4, 105.3, 86.8, 78.6, 32.9, 13.8; LCMS (MM:ES+APCI) (M+H)$^+$ 587.8.

Characterization of Compound 118:

$^1$H NMR (CDCl$_3$, 400 MHz): –δ 8.63 (s, 1H, Py-H), 8.31 (s, 1H, Ar—H), 7.83-7.81 (d, 1H, Ar—H), 7.67-7.64 (m, 2H, Ar—H), 7.39-7.21 (m, 7H, Ar—H), 7.07-7.03 (m, 1H, Ar—H), 6.93-6.89 (m, 1H, Ar—H), 6.12 (s, 1H, Meyhine), 5.14 (s, 1H, Methyne), 3.84 (S, 3H), 3.83 (s, 3H, Methoxy), 2.38 (s, 3H, Methyl), 2.1 (s, 1H, NH): LCMS (MM:ES+APCI) (M+H)$^+$ 617.2.

Example 6: Compounds 119-120

Compounds 115-118 were prepared following General Synthetic Protocol 7 above. The compounds made, and their starting materials, are outlined in Table 7 below.

TABLE 7

| Compounds of Formula K | Compounds 115-118 (Compounds of Formula n/(I)) |
|---|---|
| (structure) | 119 |
| (structure) | 120 |

Characterization of Compound 119:

$^1$H NMR (CDCl$_3$, 400 MHz): –δ 11.03 (s, 1H, Tet-NH—), 8.60 (s, 1H, Py-H), 8.31 (s, 1H, Ar—H), 7.84-7.83 (d, 1H, Ar—H), 7.68-7.65 (m, 2H, Ar—H), 7.42-7.39 (m, 2H, Ar—H), 7.08-7.06 (d, 1H, Ar—H), 6.93-6.91 (d, 1H, Ar—H), 4.90 (s, 1H, Methine), 3.83 (s, 3H, —OCH$_3$), 2.46 (s, 3H, —CH$_3$); $^{13}$C NMR (CDCl$_3$, 100 MHz) δ 182.1, 163.3, 161.9, 157.4, 154.3, 152.5, 146.4, 139.4, 136.9, 135.0, 134.2, 131.4, 130.0, 128.3, 125.4, 123.3, 119.9, 115.3, 105.3, 87.0, 56.1, 32.9, 13.6. LCMS (MM:ES+APCI) (M+H)$^+$ 541.8.

Characterization of Compound 120:

$^1$H NMR (CDCl$_3$, 400 MHz): –δ 10.04 (s, 1H, Tet-NH—), 8.61 (s, 1H, Py-H), 8.32 (s, 1H, Ar—H), 7.83-7.82 (d, 1H, Ar—H), 7.68-7.64 (m, 2H, Ar—H), 7.41-7.37 (m, 2H, Ar—H), 7.06-7.04 (d, 1H, Ar—H), 6.92-6.90 (d, 1H, Ar—H), 4.95 (s, 1H, Methine), 2.41 (s, 3H, —CH$_3$): LCMS (MM:ES+APCI) (M+H)$^+$ 511.2.

While representative compounds and their synthesis have been shown and described in Examples 1 to 7, various modifications and substitutions may be made thereto without departing from the spirit and scope of the present disclosure. Accordingly, it is to be understood that the compounds synthesized in Example 1 are representative compounds of the Compound of Formula (I), and a person of average skill in the art can arrive at all other possible compounds of the Compound of Formula (I) through corresponding synthetic procedure based on the description/examples of the present disclosure. Arriving at such new compounds of the Compound of Formula (I) is within the scope of present disclosure.

Example 8

Biological Activity of Selected Compounds

Oncogenicity Assays

The above synthesised compounds were initially evaluated against a range of carcinoma cells using an AlamarBlue™ cell viability assay (using the protocol discussed above). The tested compounds were generally efficacious at reducing the viability of various carcinoma cells compared to vehicle (DMSO) treated cells. Table 8 provides selected IC$_{50}$ data for certain of the compounds synthesised herein against MCF-7.

TABLE 8
| Compound | IC$_{50}$ (μM) | Chemical Structure |
|---|---|---|
| 1 | 22.56 | 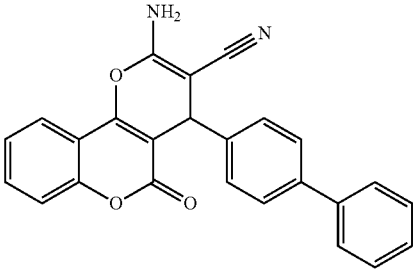 |
| 25 | 18.45 | 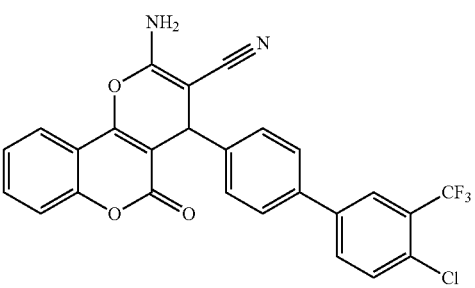 |
| 13 | 17.84 | 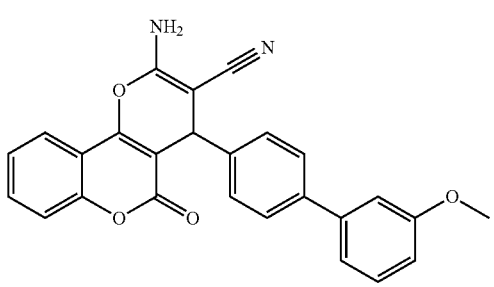 |
| 79 | 9.15 | 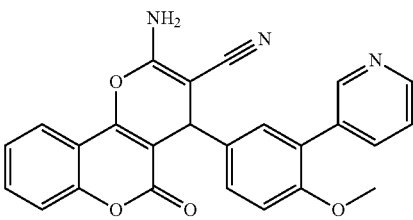 |
| 73 | 14.84 | 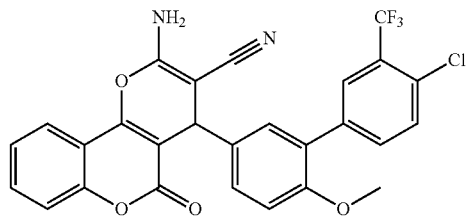 |

TABLE 8-continued
| Compound | IC$_{50}$ (μM) | Chemical Structure |
|---|---|---|
| 43 (AMPC) | 3.21 | 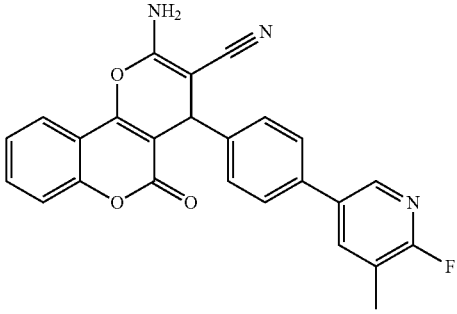 43 |
| 61 | 8.94 | 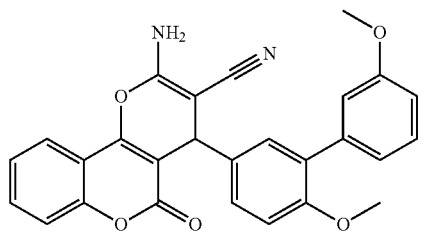 61 |
| 91 (methoxy-AMPC) | 11.84 | 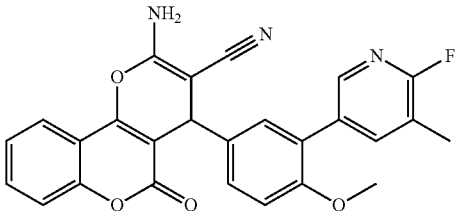 91 |
| 31 | 5.21 | 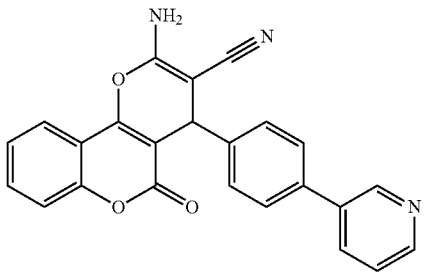 31 |
| 49 | 28.17 | 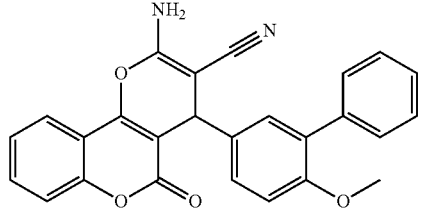 49 |

TABLE 8-continued

| Compound | IC$_{50}$ (μM) | Chemical Structure |
|---|---|---|
| 55 | 18.61 | 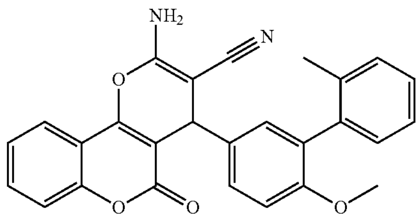 |
| 107 | 19.46 | 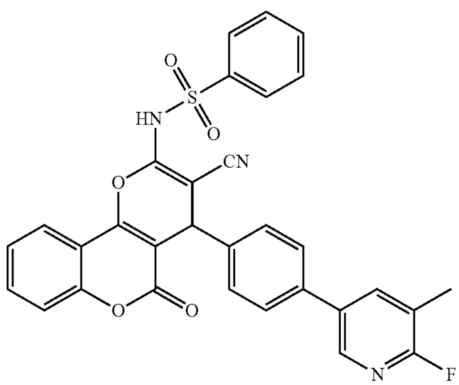 |
| 109 | 34.94 | 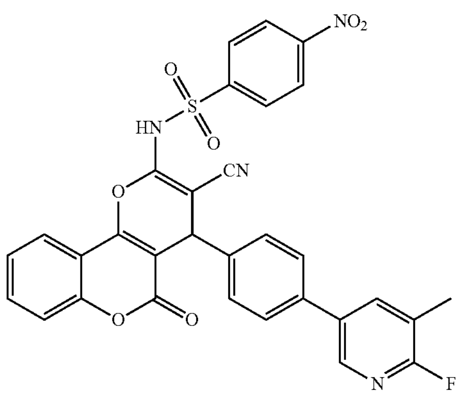 |
| 113 | 33.09 | 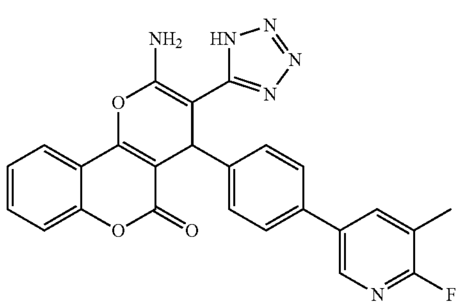 [SMILES: Cc1cc(-c2ccc(C3C(c4nnn[nH]4)=C(N)Oc4c3c(=O)oc3ccccc43)cc2)cnc1F] |

TABLE 8-continued
| Compound | IC$_{50}$ (μM) | Chemical Structure |
|---|---|---|
| 98 | 58.33 | 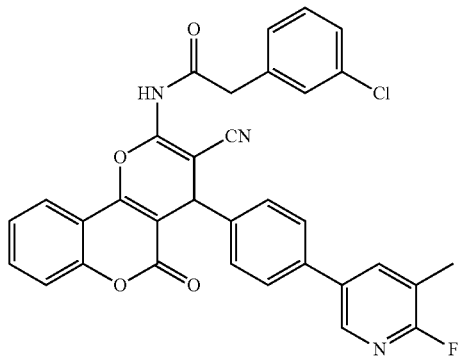<br>98 |
| 99 | 33.36 | 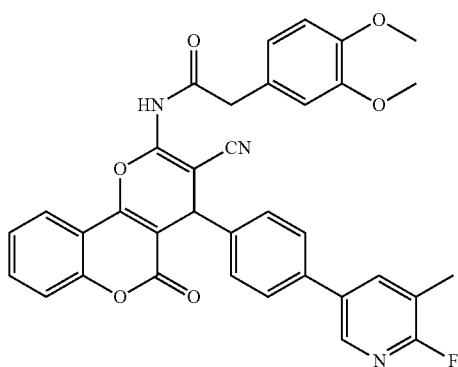<br>99 |
| 100 | 177.43 | 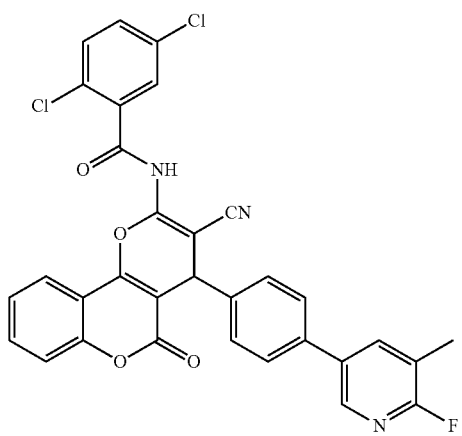<br>100 |

TABLE 8-continued
| Compound | IC$_{50}$ (μM) | Chemical Structure |
|---|---|---|
| 101 | 40.4 | 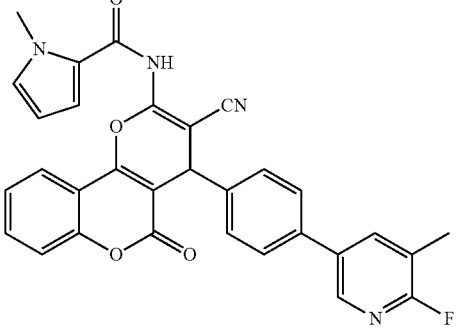<br>101 |
| 102 | 33 | 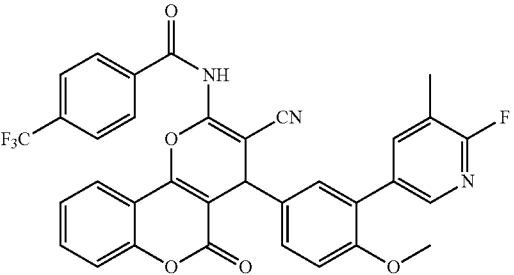<br>102 |
| 111 | 39.27 | 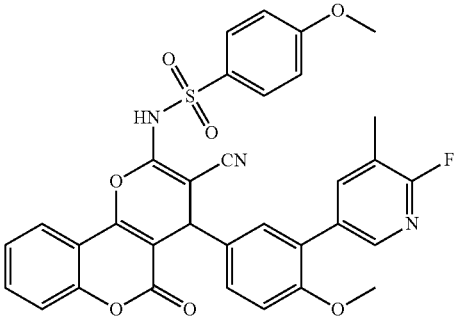<br>111 |
| 112 | 100.97 | 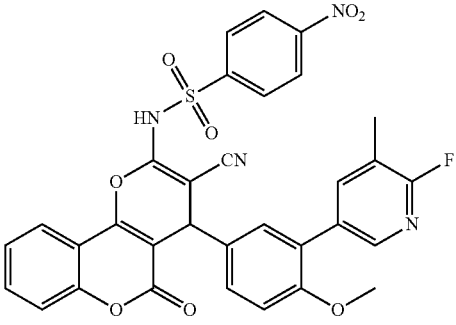<br>112 |

TABLE 8-continued
| Compound | IC$_{50}$ (μM) | Chemical Structure |
|---|---|---|
| 114 | 39.77 | 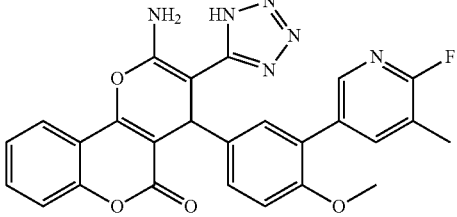<br>114 |
| 103 | 40.03 | 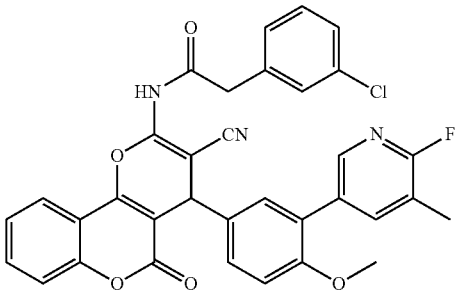<br>103 |
| 104 | 8.96 | 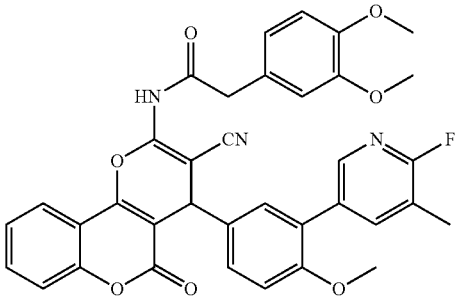<br>104 |
| 105 | 23.7 | 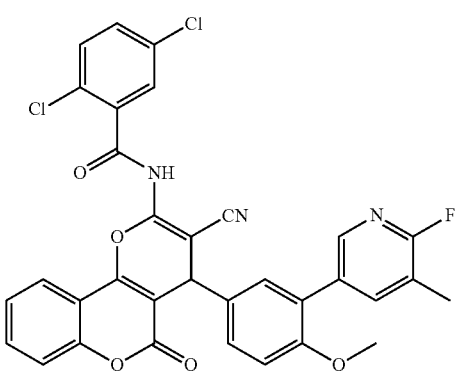<br>105 |

TABLE 8-continued

| Compound | IC$_{50}$ (μM) | Chemical Structure |
|---|---|---|
| 106 | 55.02 | 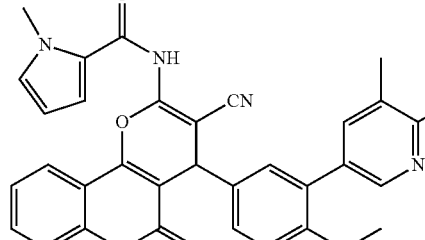 |
| 110 | 67.41 | 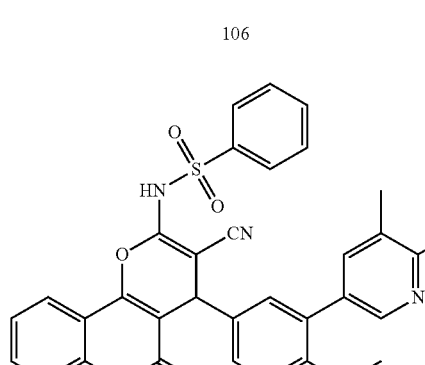 |

As an example of the data generated across a range of cancer cell lines, FIGS. 1-5 and Tables 9-10 show the efficacy of compound 43 (AMPC) against a range of cell lines, particularly where the cell line expresses TFF3. Further details of these experiments are contained within the "Drawings" section hereinbefore.

The invention claimed is:
1. A compound of formula I:

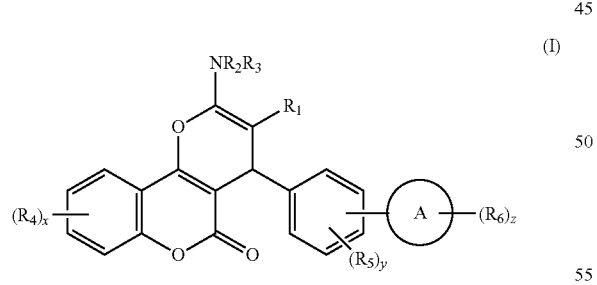

(I)

wherein:
R$_1$ represents CN or Het$^a$, which latter group is unsubstituted or substituted by halo, C$_{1-6}$ alkyl, C$_{2-6}$ alkenyl, C$_{2-6}$ alkynyl, or C$_{3-6}$ cycloalkyl, which latter four groups are unsubstituted or substituted by one or more substituents selected from halo, OH and NH$_2$;
R$_2$ and R$_3$ independently represent H, C(O)R$_7$, S(O)$_{x'}$ R$_{7'}$, C$_{1-6}$ alkyl, C$_{2-6}$ alkenyl, C$_{2-6}$ alkynyl, or C$_{3-6}$ cycloalkyl, which latter four groups are unsubstituted or substituted by one or more substituents selected from halo, OH and NH$_2$; or R$_1$ and R$_2$ and/or R$_3$, together with the atoms they are attached to, form a heterocyclic or heteroaromatic ring system having from 9 to 10 atoms in the ring system, which ring system is unsubstituted or substituted by one or more groups selected from =S, =O, halo, C$_{1-6}$ alkyl, C$_{2-6}$ alkenyl, C$_{2-6}$ alkynyl, C$_{3-6}$ cycloalkyl, aryl, or Het$^b$, which latter six groups are unsubstituted or substituted by one or more substituents selected from halo, OR$_8$ and NR$_9$R$_{10}$;
each R$_4$ independently represents halo, C$_{1-6}$ alkyl, C$_{2-6}$ alkenyl, C$_{2-6}$ alkynyl, C$_{3-6}$ cycloalkyl, (which latter four groups are unsubstituted or substituted by one or more substituents selected from halo, OH and NH$_2$), OR$_{11}$, or NR$_{12}$R$_{13}$,
each R$_5$ independently represents halo, C$_{1-6}$ alkyl, C$_{2-6}$ alkenyl, C$_{2-6}$ alkynyl, C$_{3-6}$ cycloalkyl, (which latter four groups are unsubstituted or substituted by one or more substituents selected from halo, OH and NH$_2$), OR$_{14}$, or NR$_{15}$R$_{16}$;
each R$_6$ independently represents halo, C$_{1-6}$ alkyl, C$_{2-6}$ alkenyl, C$_{2-6}$ alkynyl, C$_{3-6}$ cycloalkyl, (which latter four groups are unsubstituted or substituted by one or more substituents selected from halo, OH, NH$_2$, and =O), OR$_{17}$, or NR$_{18}$R$_{19}$;
R$_7$ and R$_{7'}$ independently represent Het$^c$, aryl, C$_{1-6}$ alkyl, C$_{2-6}$ alkenyl, C$_{2-6}$ alkynyl, or C$_{3-6}$ cycloalkyl, which latter five groups are unsubstituted or substituted by one or more substituents selected from aryl (which group is unsubstituted or substituted by one or more of C$_{1-6}$ alkyl, alkoxy, halo, NO$_2$, OH and NH$_2$), alkoxy, C$_{1-3}$ alkyl, Het$^d$, halo, OH and NH$_2$;
R$_8$, R$_{11}$, R$_{14}$ and R$_{17}$ each independently represent at each occurrence thereof H, C$_{1-6}$ alkyl, C$_{2-6}$ alkenyl, C$_{2-6}$ alkynyl, or C$_{3-6}$ cycloalkyl, which latter four groups are unsubstituted or substituted by one or more substituents selected from halo, alkoxy, OH and NH$_2$;

R$_9$, R$_{10}$, R$_{12}$, R$_{13}$, R$_{15}$, R$_{16}$, R$_{18}$, and R$_{19}$ each independently represent at each occurrence thereof H, C$_{1-6}$ alkyl, C$_{2-6}$ alkenyl, C$_{2-6}$ alkynyl, or C$_{3-6}$ cycloalkyl, which latter four groups are unsubstituted or substituted by one or more substituents selected from halo, alkoxy, OH and NH$_2$;

Het$^a$ to Het$^d$ independently represent, at each occurrence, a 5- or 6-membered heterocyclic or heteroaromatic groups containing one or more heteroatoms selected from O, S and N, which heterocyclic groups are optionally substituted by one or more substituents selected from =O, =S, halo, OH, C$_{1-4}$ alkyl and C$_{1-4}$ alkoxy, which latter two groups are optionally substituted by one or more substituents selected from halo, OH and NH$_2$;

A represents a 5- to 13-membered carbocyclic or heterocyclic ring system that is aromatic and/or non-aromatic;

x is from 0 to 4;

x' is from 1 to 2;

y is from 0 to 5; and z is from 0 to 5, or a pharmaceutically acceptable salt or solvate, or a deuteriated compound of the Formula I thereof;

with the proviso that a compound of formula I excludes the following compounds:

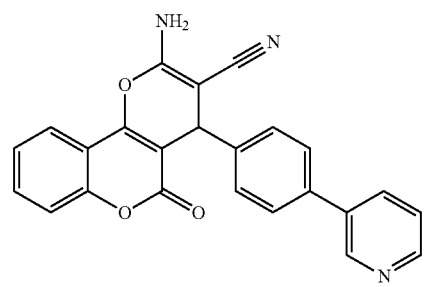

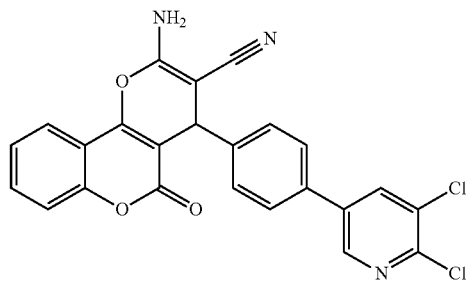

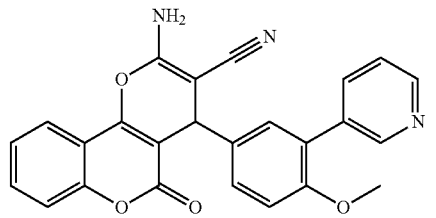

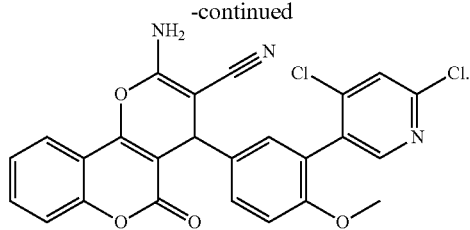

2. The compound of claim 1, wherein R$_1$ represents CN or Het$^a$, which latter group is unsubstituted or substituted by halo, C$_{1-6}$ alkyl, C$_{2-6}$ alkenyl, C$_{2-6}$ alkynyl, or C$_{3-6}$ cycloalkyl, which latter four groups are unsubstituted or substituted by one or more substituents selected from halo, OH and NH$_2$.

3. The compound of claim 1, wherein R$_2$ and R$_3$ independently represent H, C(O)R$_7$, S(O)$_x$R$_7$, C$_{1-6}$ alkyl, C$_{2-6}$ alkenyl, C$_{2-6}$ alkynyl, or C$_{3-6}$ cycloalkyl, which latter four groups are unsubstituted or substituted by one or more substituents selected from halo, OH and NH$_2$.

4. The compound of claim 3, wherein R$_2$ and R$_3$ independently represent H, C(O)R$_7$ and S(O)$_2$R$_{7'}$.

5. The compound of claim 1, wherein Het$^a$ to Het$^d$ independently represent, at each occurrence, a 5- or 6-membered heteroaromatic group containing one or more heteroatoms selected from 0 and N, which heterocyclic groups are unsubstituted or substituted by one or more substituents selected from =O, halo, OH, C$_{1-4}$ alkyl and C$_{1-4}$ alkoxy, which latter two groups are optionally substituted by one or more substituents selected from halo, OH and NH$_2$.

6. The compound of claim 1, wherein A represents a 6- to 10-membered aromatic or heterocyclic ring system, optionally wherein A represents a 6-membered aromatic or heterocyclic ring system.

7. The compound of claim 1, wherein:
x is from 0 to 2; and/or
x', when present, is 2; and/or
y is from 1 to 3; and/or
z is from 1 to 3.

8. The compound of claim 1, wherein:
R$_1$ represents CN or Het$^a$, which latter group is unsubstituted or substituted by halo, C$_{1-6}$ alkyl, which latter four group is unsubstituted or substituted by one or more substituents selected from halo, OH and NH$_2$;
R$_2$ and R$_3$ independently represent H, C(O)R$_7$, S(O)$_x$R$_{7'}$, C$_{1-6}$ alkyl, which latter group is unsubstituted or substituted by one or more substituents selected from halo, OH and NH$_2$;
each R$_4$ independently represents halo, C$_{1-6}$ alkyl (which latter group is unsubstituted or substituted by one or more substituents selected from halo, OH and NH$_2$), OR$_{11}$, or NR$_{12}$R$_{13}$,
each R$_5$ independently represents halo, C$_{1-6}$ alkyl (which latter group is unsubstituted or substituted by one or more substituents selected from halo, OH and NH$_2$), OR$_{14}$, or NR$_{15}$R$_{16}$;
each R$_6$ independently represents halo, C$_{1-6}$ alkyl (which latter group is unsubstituted or substituted by one or more substituents selected from halo, OH and NH$_2$), OR$_{17}$, or NR$_{18}$R$_{19}$;
R$_7$ and R$_{7'}$ independently represent Het$^c$, aryl, C$_{1-6}$ alkyl, which latter two groups are unsubstituted or substituted by one or more substituents selected from aryl (which group is unsubstituted or substituted by one or more of C$_{1-6}$ alkyl, alkoxy, halo, NO$_2$, OH and NH$_2$), alkoxy, C$_{1-3}$ alkyl, Het$^d$, halo, OH and NH$_2$;

R$_{11}$, R$_{14}$ and R$_{17}$ each independently represent at each occurrence thereof H, C$_{1-6}$ alkyl, C$_2$-6 alkenyl, C$_{2-6}$ alkynyl, or C$_{3-6}$ cycloalkyl, which latter four groups are unsubstituted or substituted by one or more substituents selected from halo, alkoxy, OH and NH$_2$;

R$_{12}$, R$_{13}$, R$_{15}$, R$_{16}$, R$_{18}$, and R$_{19}$ each independently represent at each occurrence thereof H, C$_{1-6}$ alkyl, which latter group is unsubstituted or substituted by one or more substituents selected from halo, alkoxy, OH and NH$_2$;

Het$^a$, Het$^c$ and Het$^d$ independently represent, at each occurrence, a 5- or 6-membered heterocyclic or heteroaromatic group containing one or more heteroatoms selected from O, S and N, which heterocyclic groups are optionally substituted by one or more substituents selected from =O, =S, halo, OH, C$_{1-4}$ alkyl and C$_{1-4}$ alkoxy, which latter two groups are optionally substituted by one or more substituents selected from halo, OH and NH$_2$;

A represents a 5- to 13-membered carbocyclic or heterocyclic ring system that is aromatic and/or non-aromatic;

x is from 0 to 4;

x' is from 1 to 2;

y is from 0 to 5; and z is from 0 to 5.

9. The compound according to claim 1, wherein the compound is selected from:

1
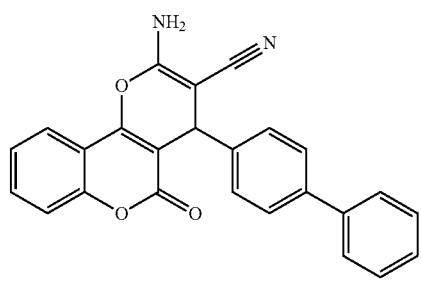

2
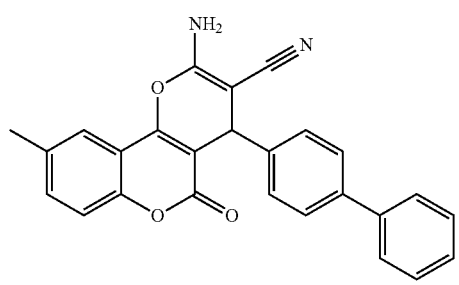

3
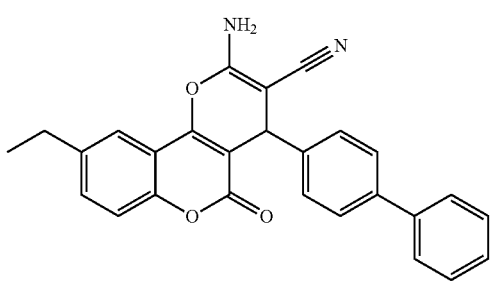

-continued

4
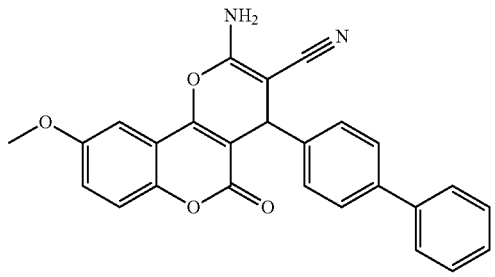

5
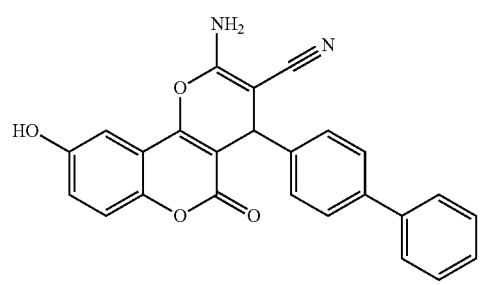

6
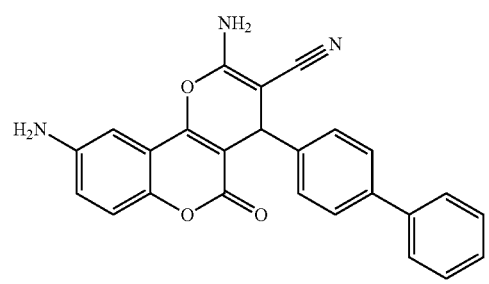

7
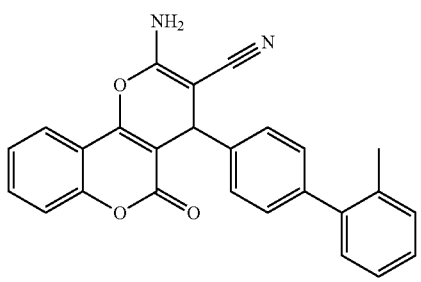

8
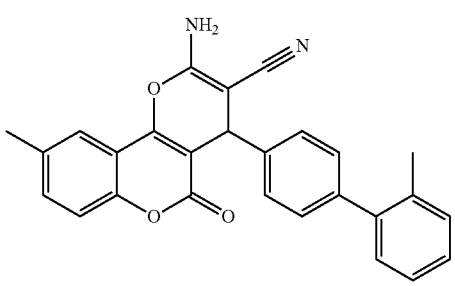

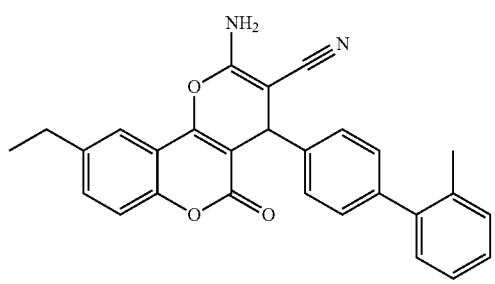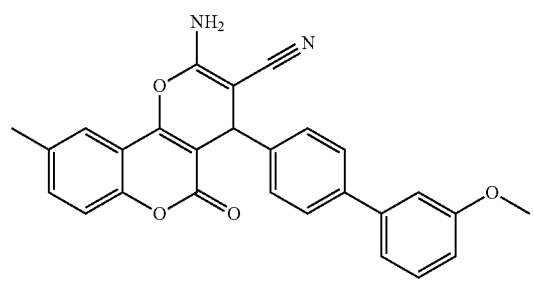

-continued
19
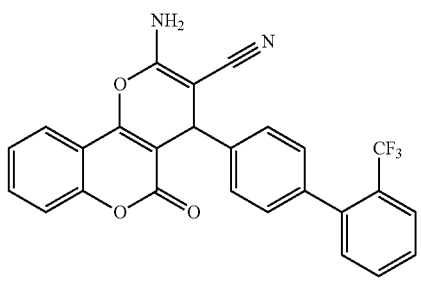
20
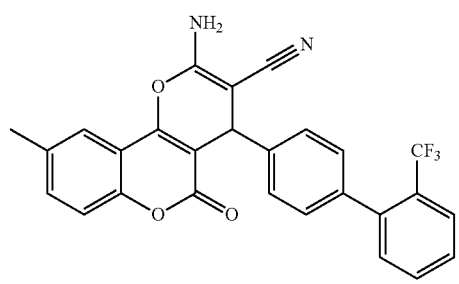
21
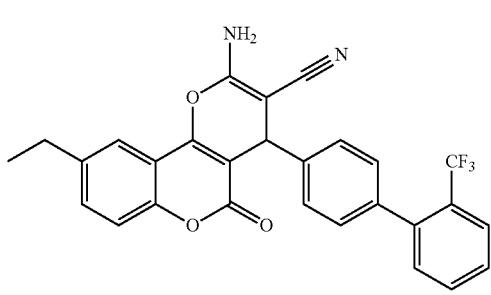
22
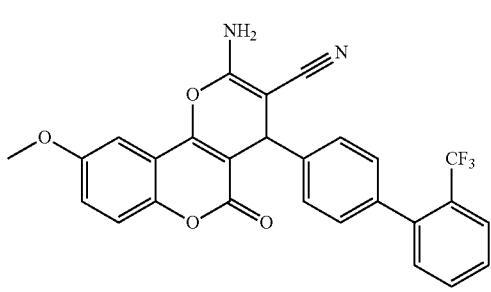
23
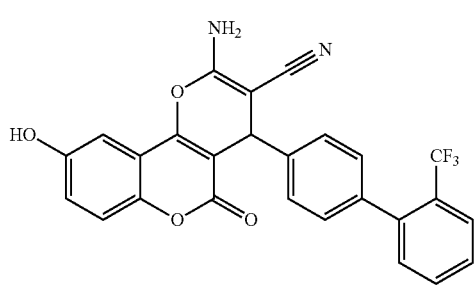
-continued
24
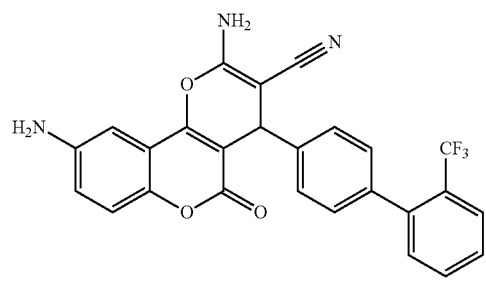
25
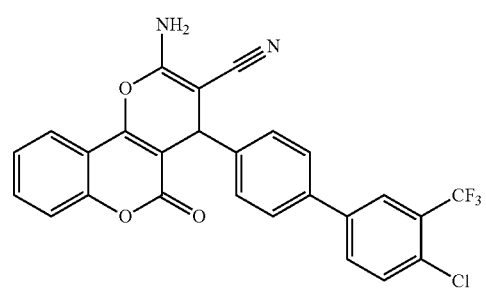
26
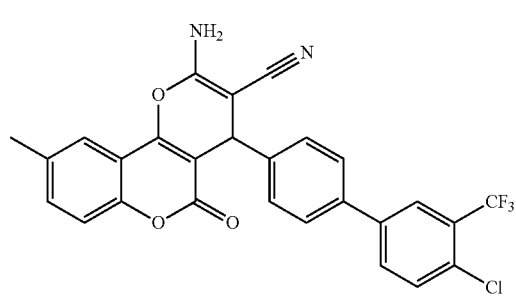
27
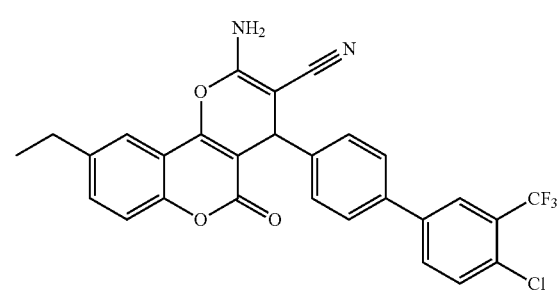
28
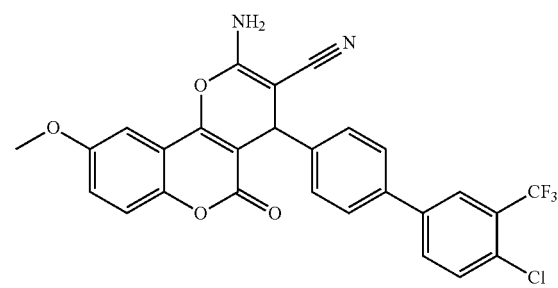

29
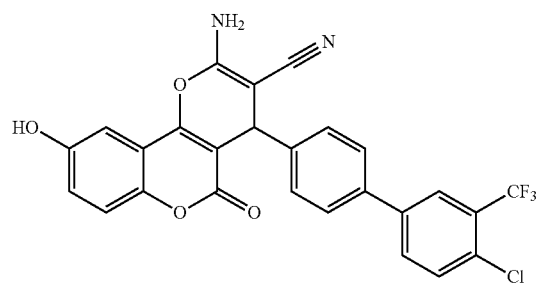
30
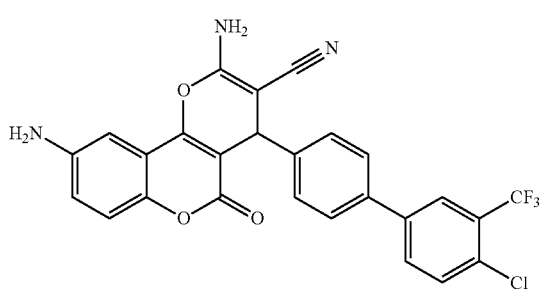
32
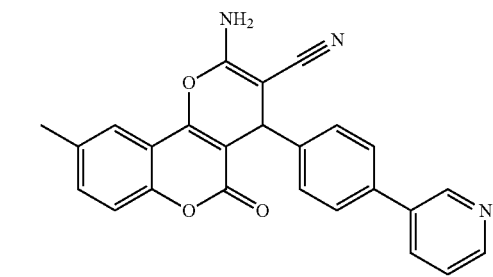
33
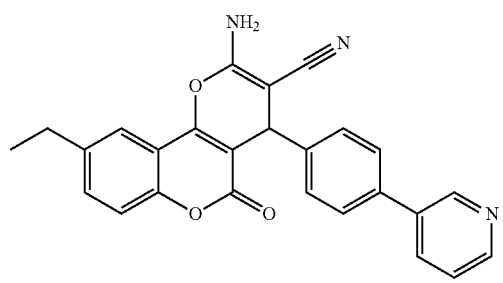
34
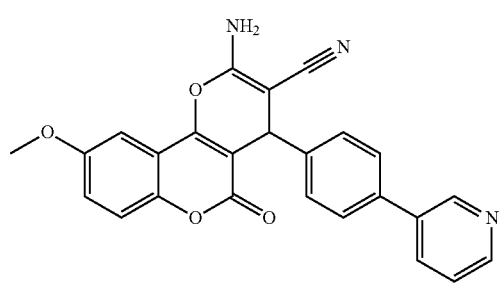
35
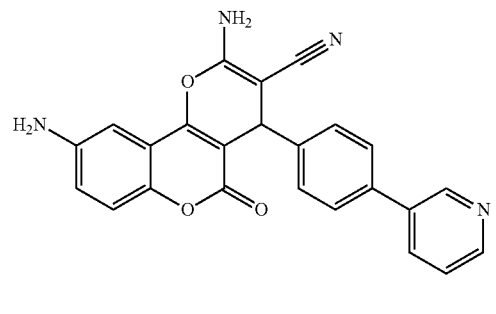
36
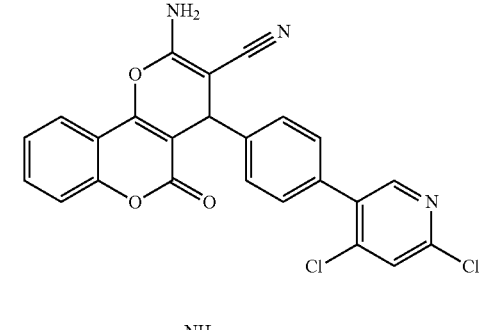
37
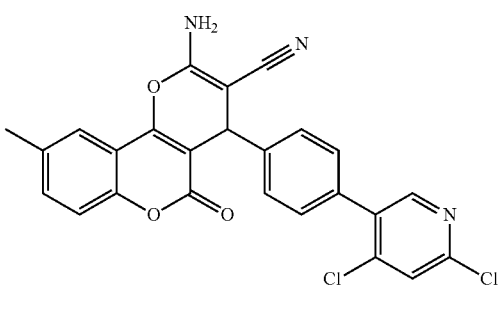
38
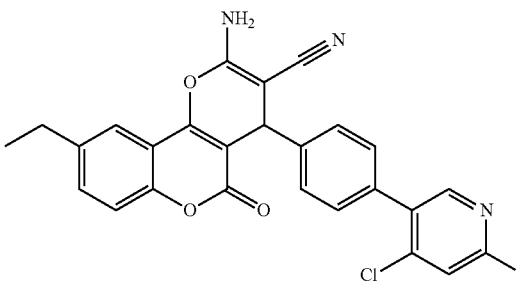
39
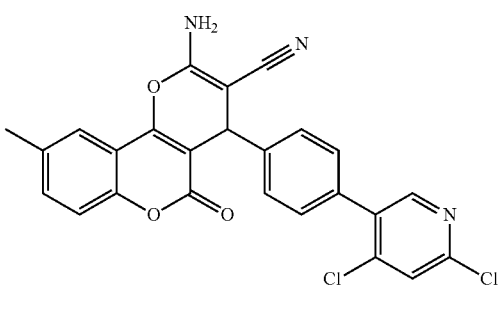

40
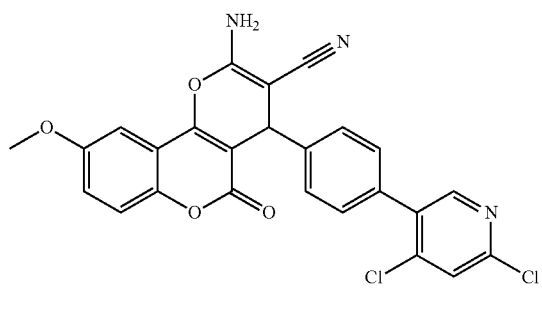
41
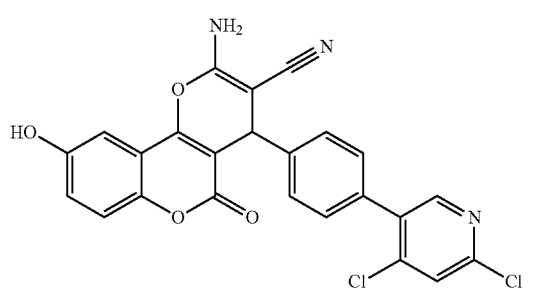
42
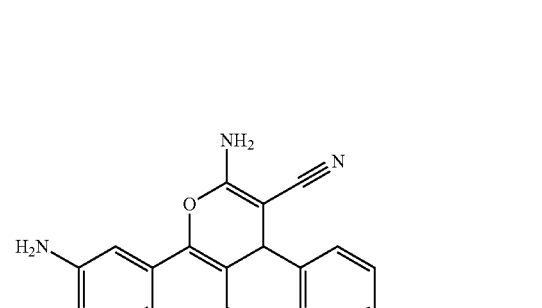
43
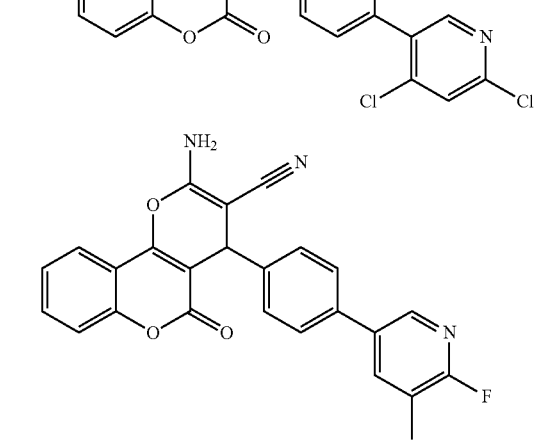
44
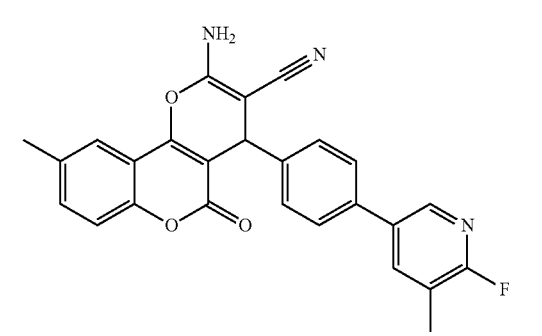
45
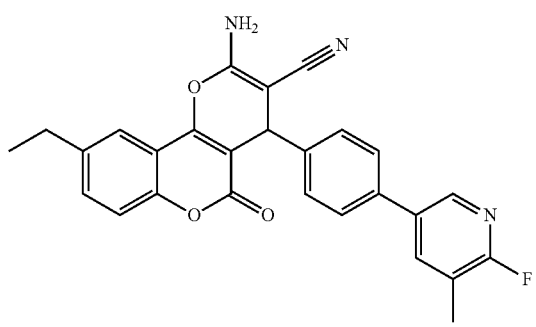
46
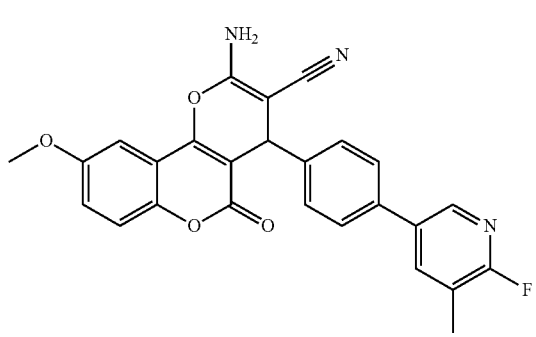
47
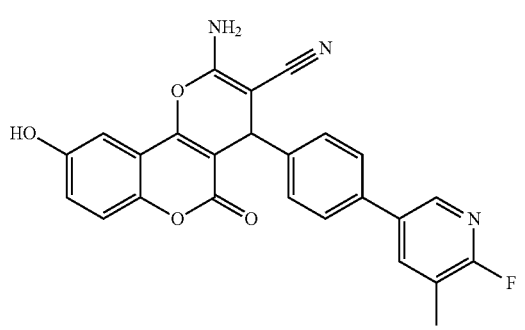
48
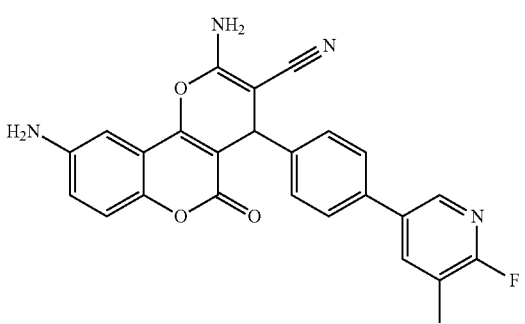
49
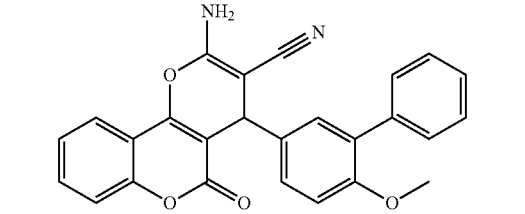

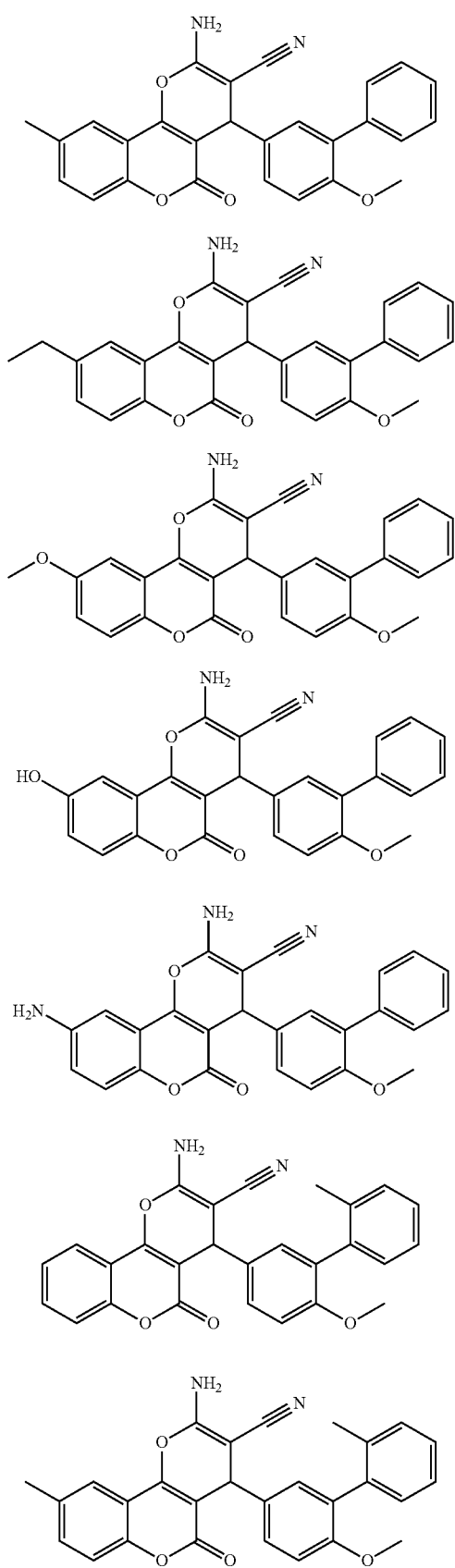
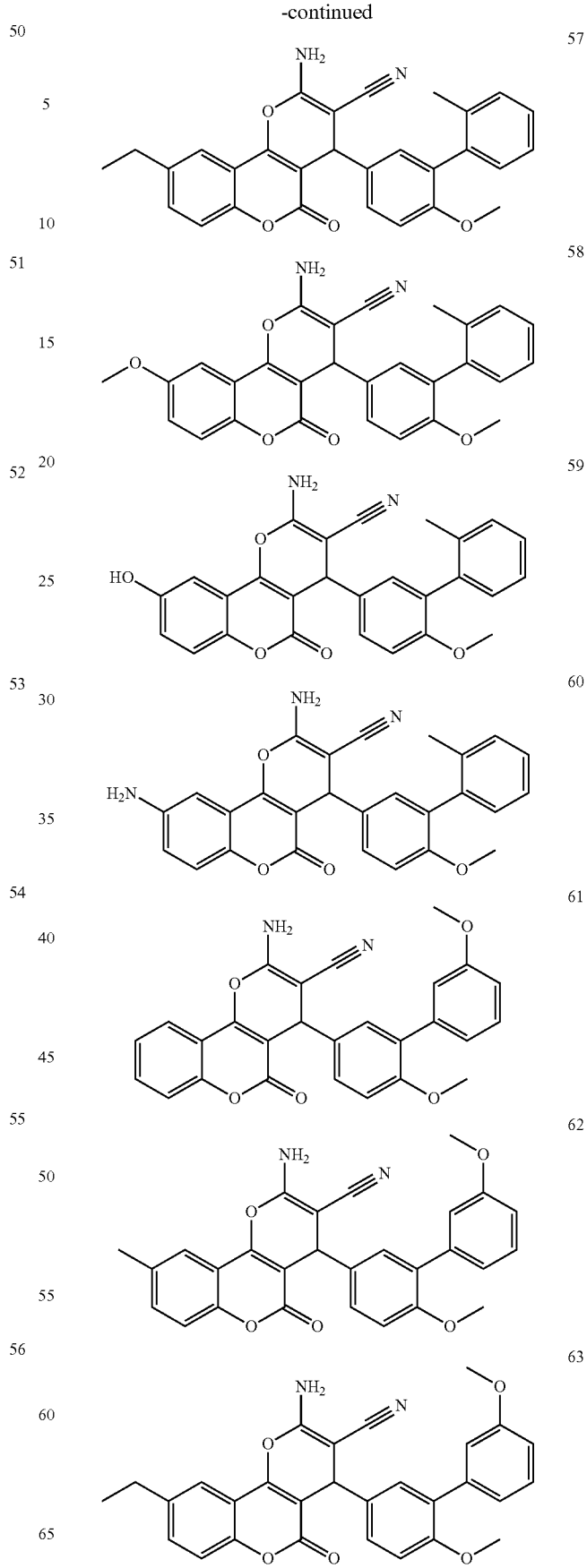

64
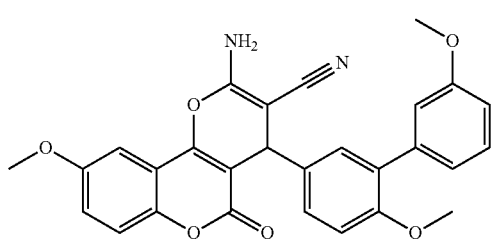
65
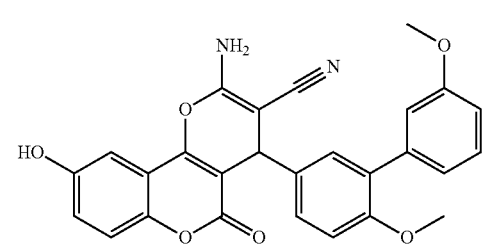
66
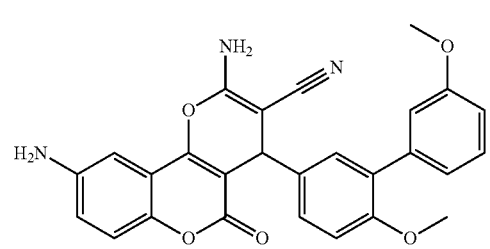
67
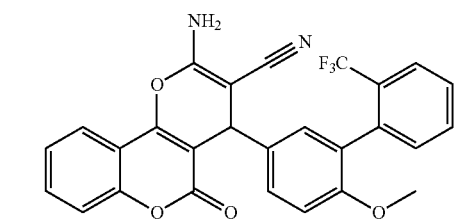
68
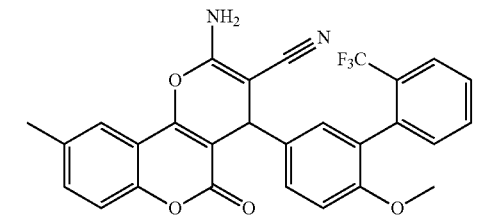
69
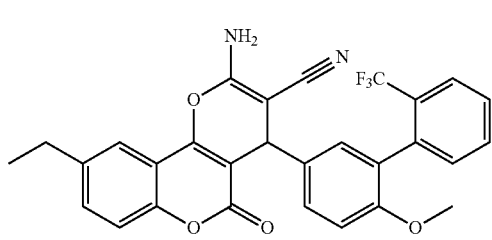
70
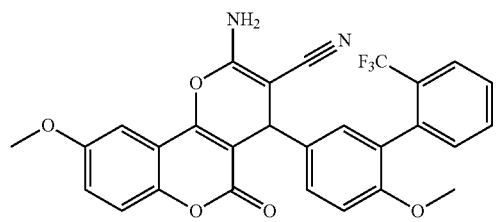
71
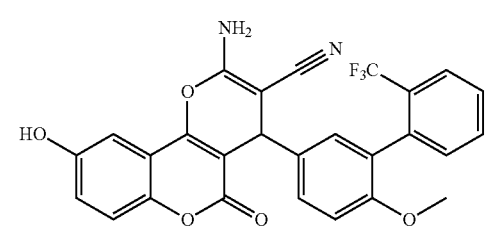
72
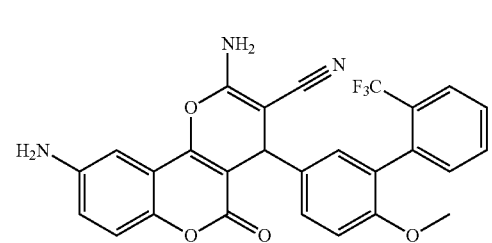
73
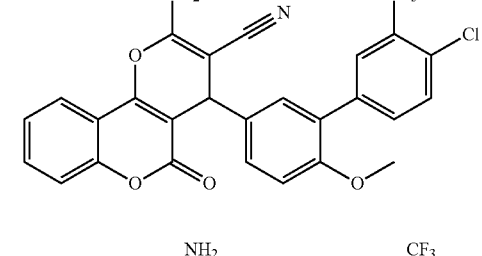
74
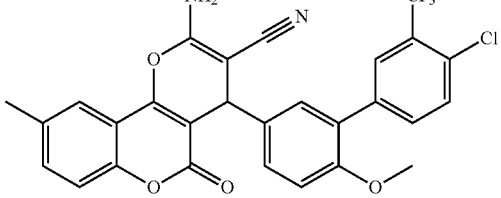
75
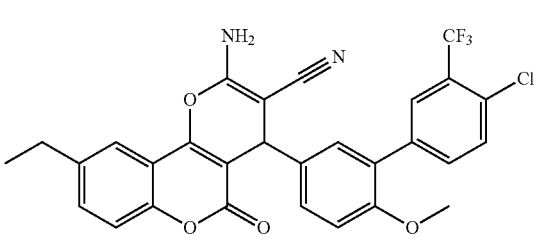

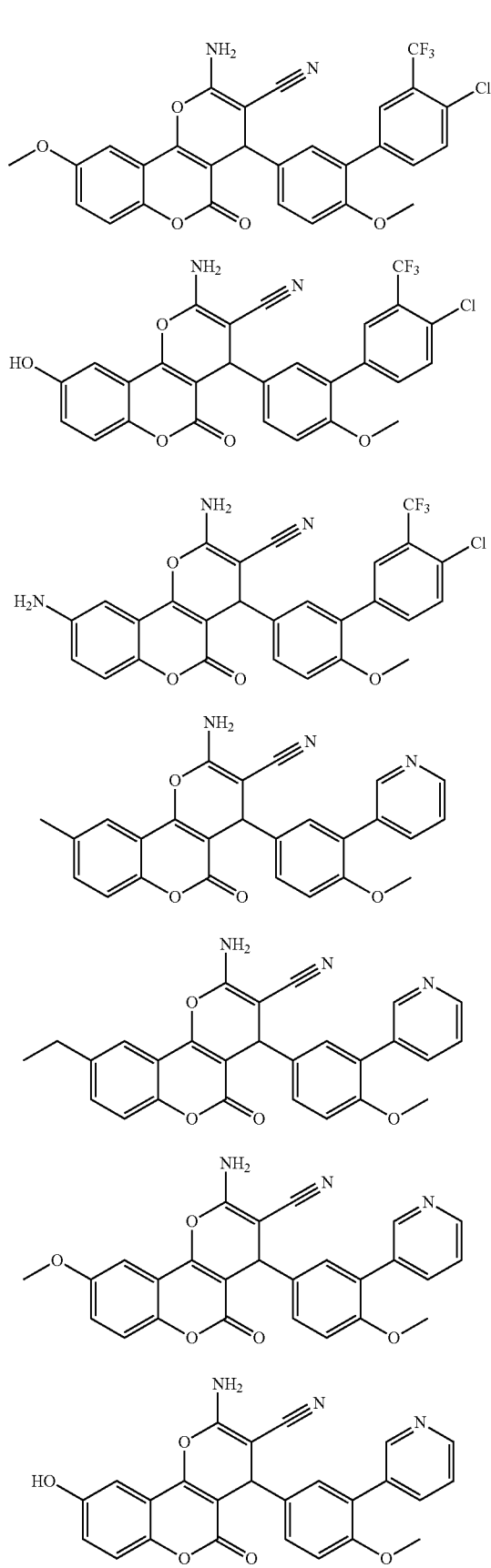
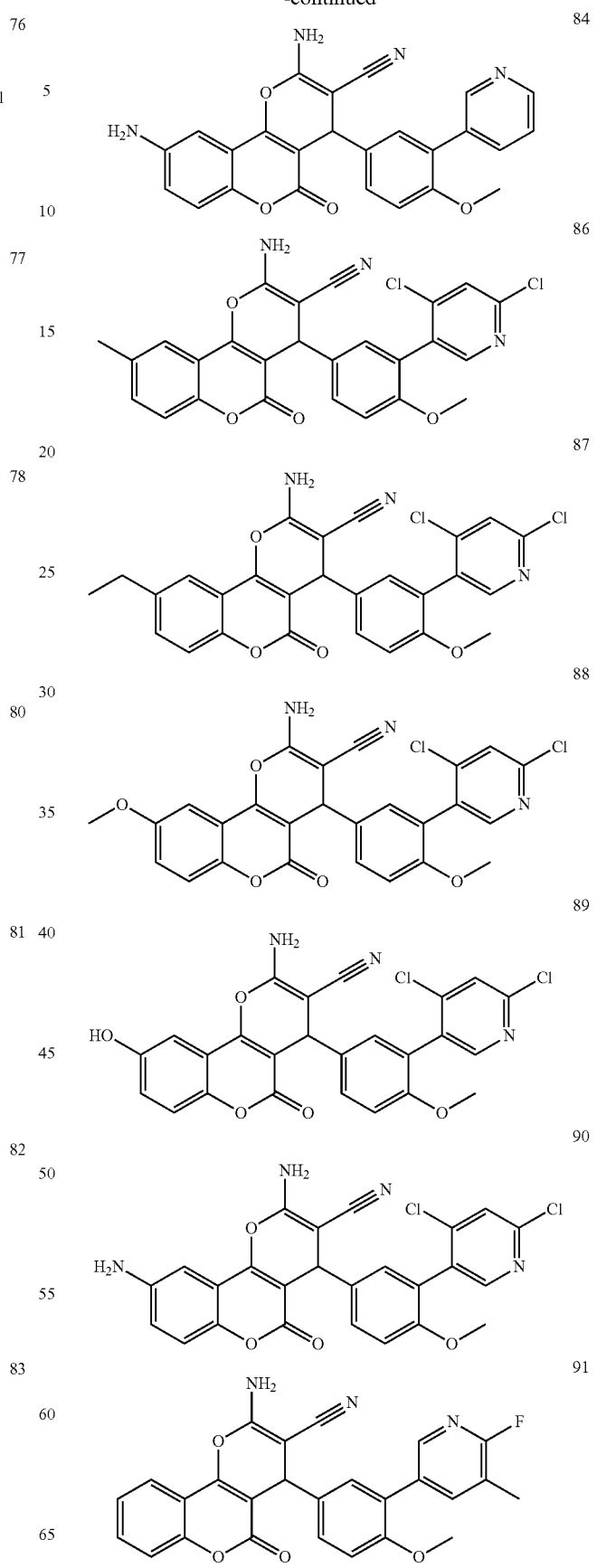

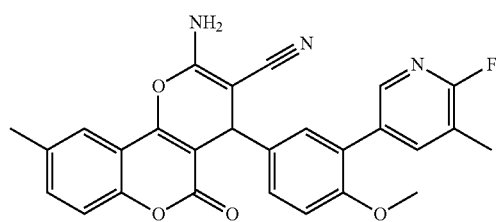
92
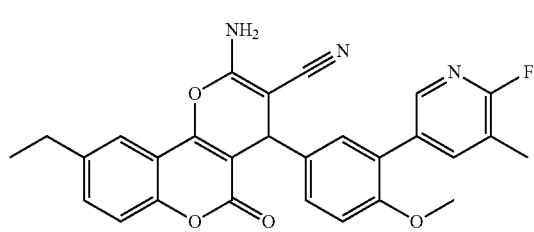
93
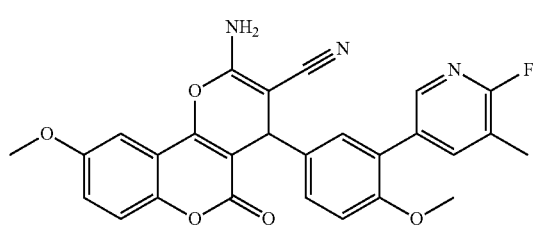
94
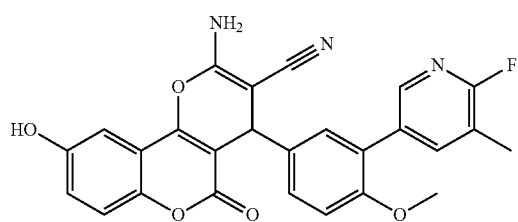
95
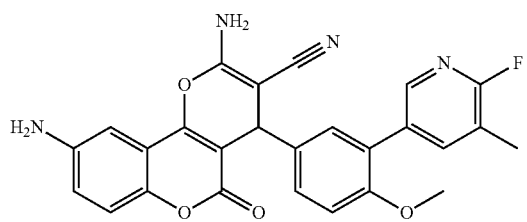
96
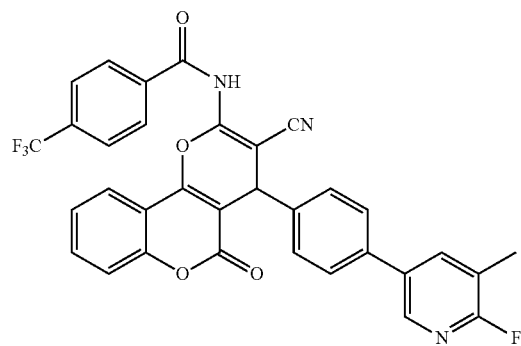
97
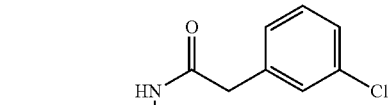
98
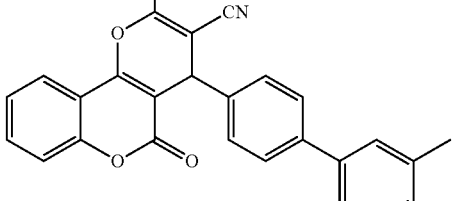
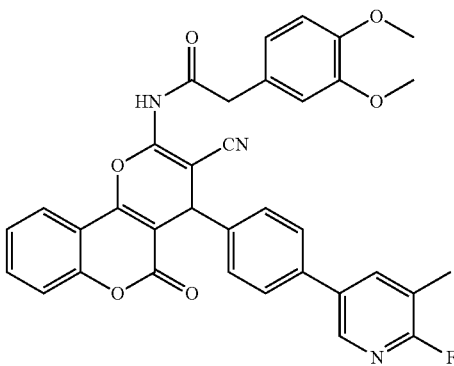
99
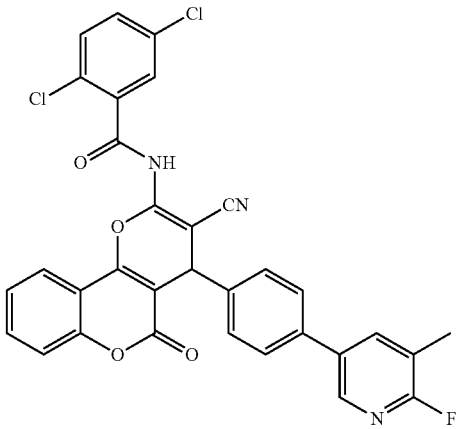
100
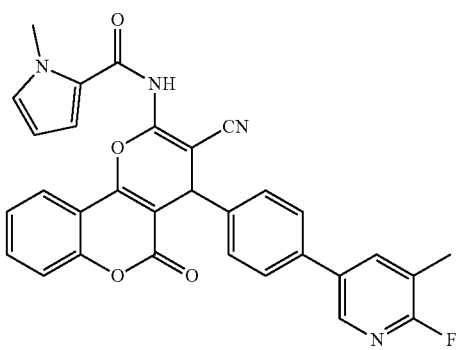
101

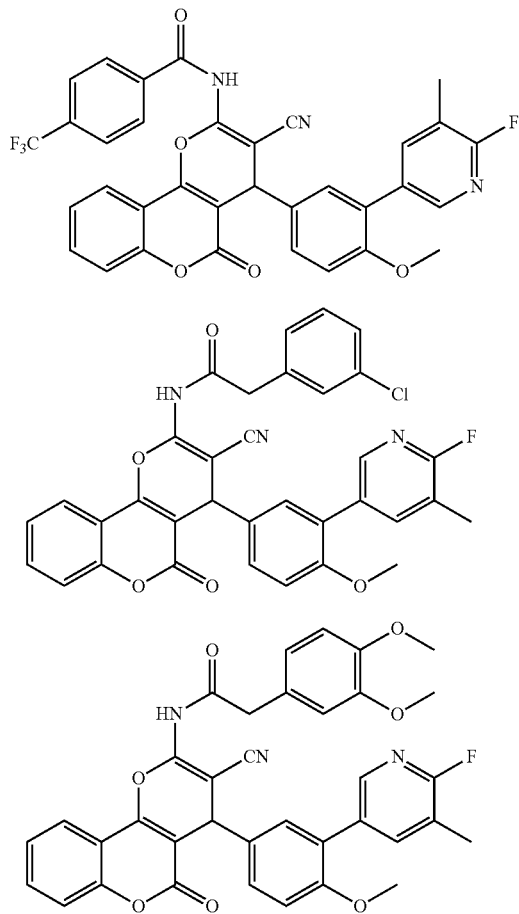
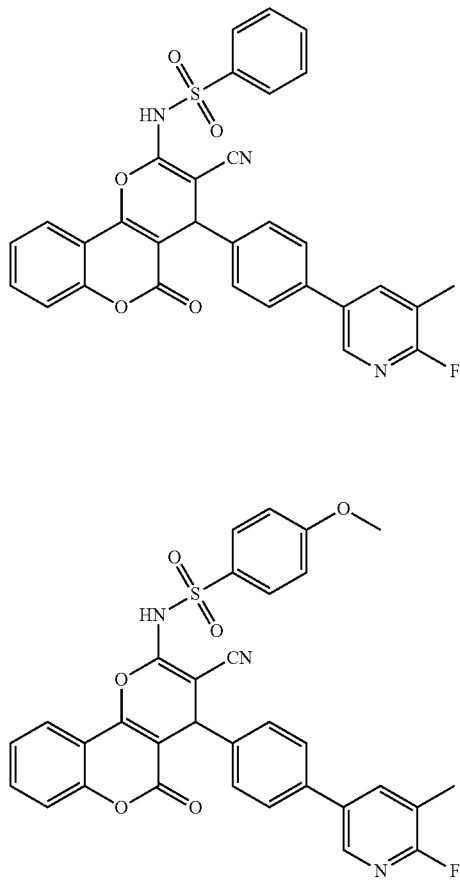
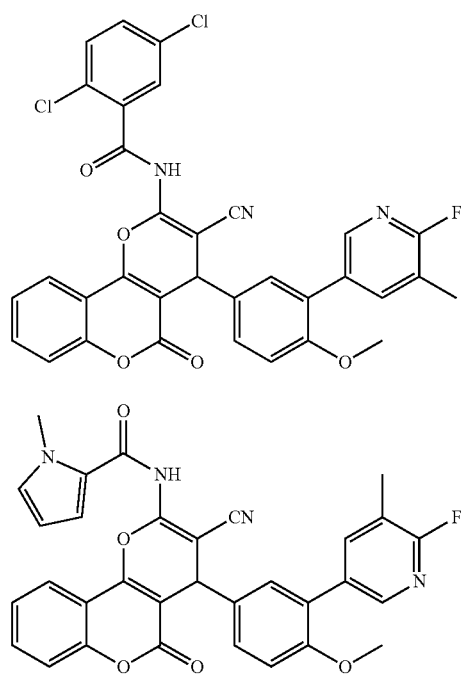

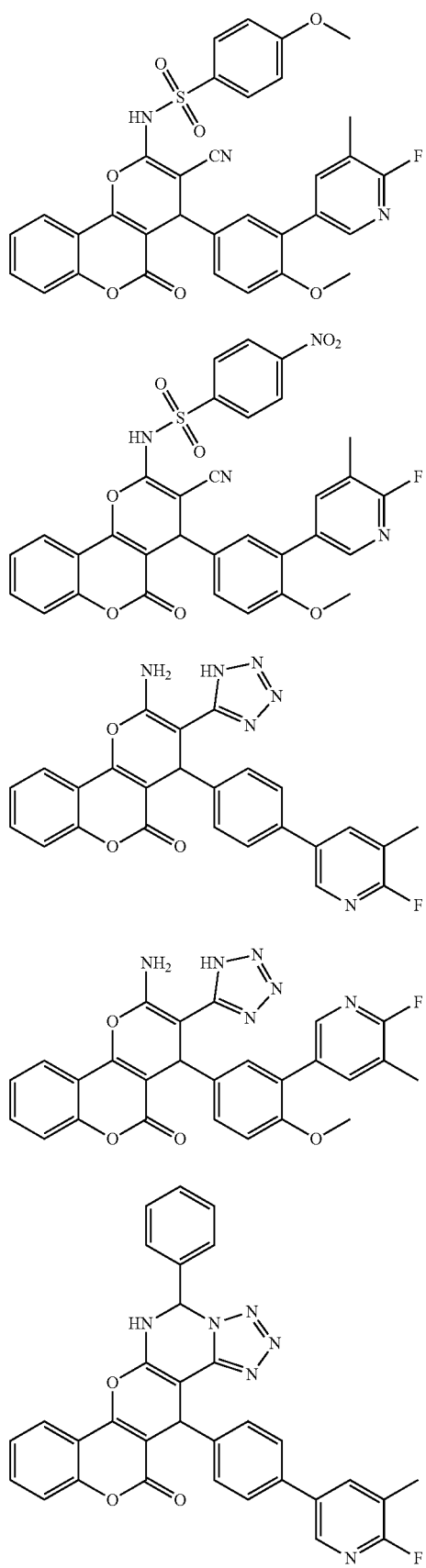
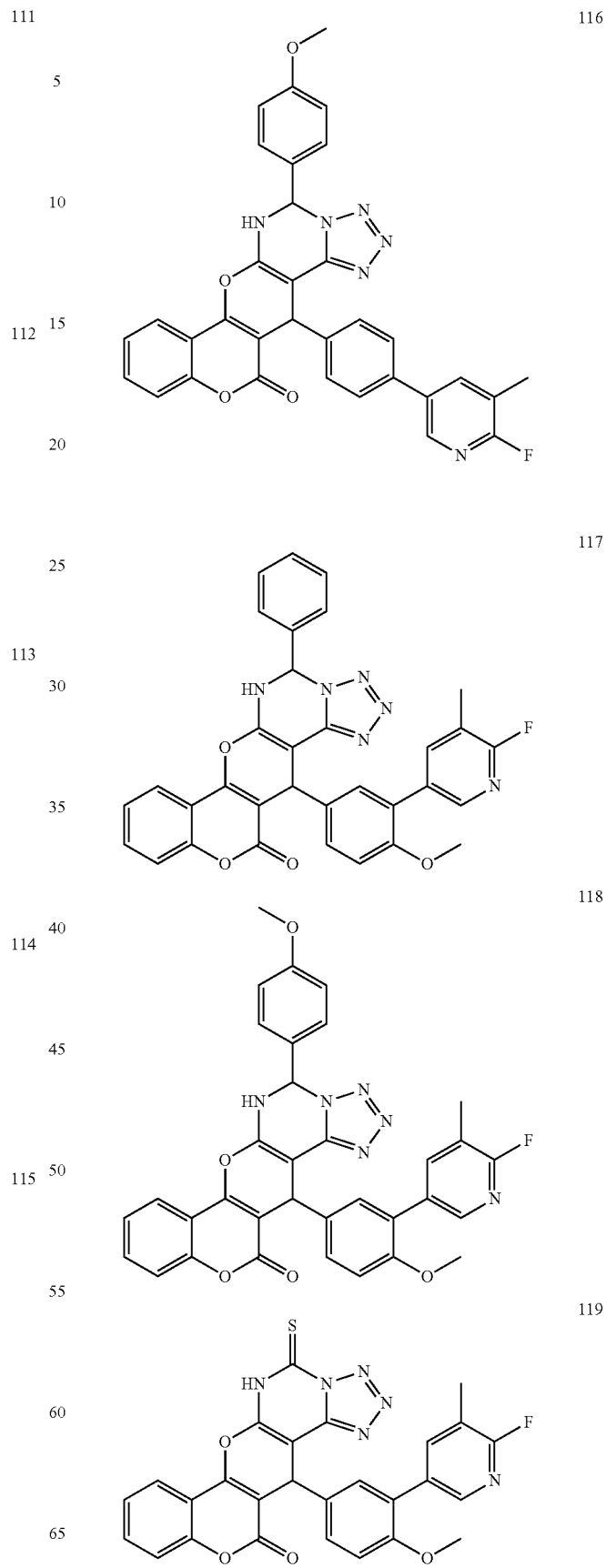

120 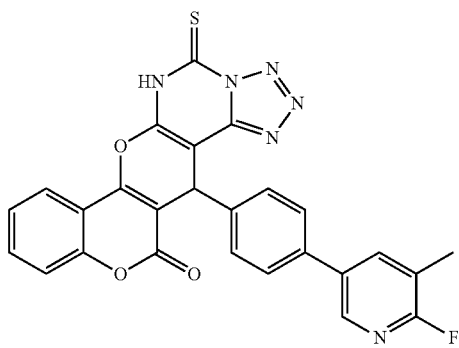
121 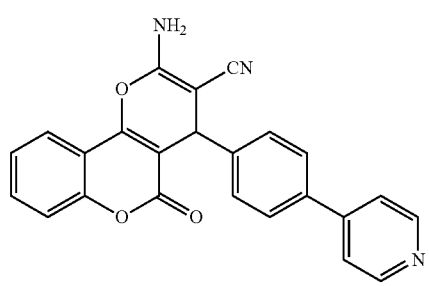
122 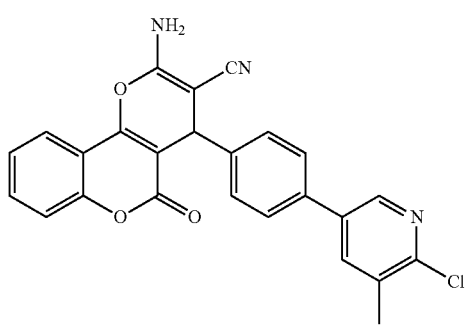
123 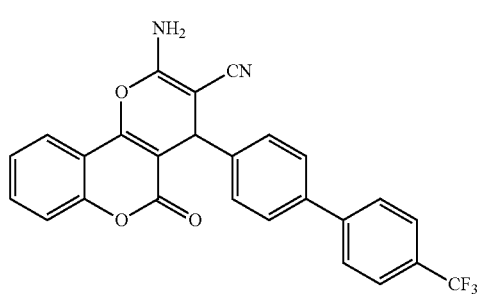
124 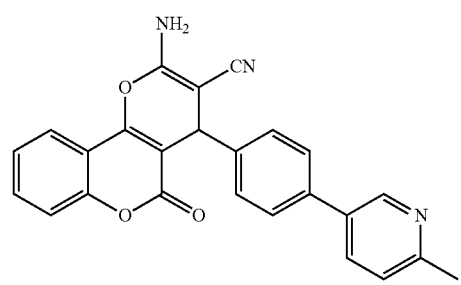
125 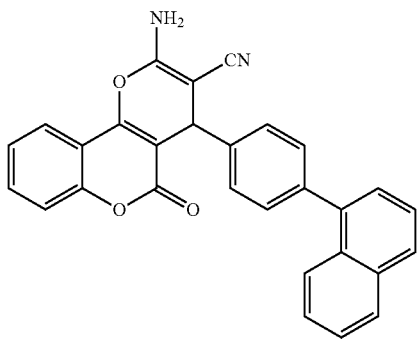
126 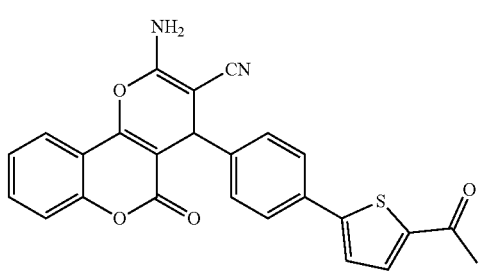
127 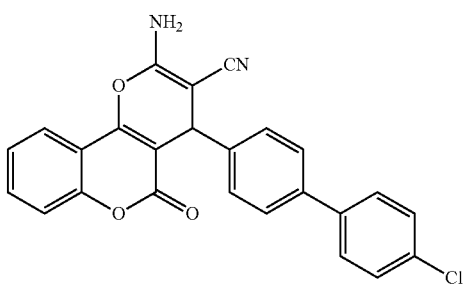
128 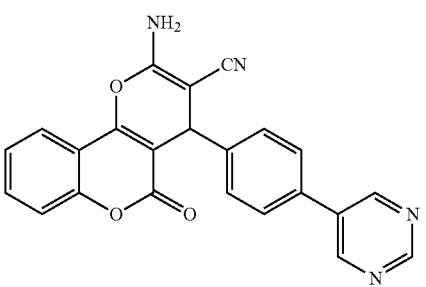
129 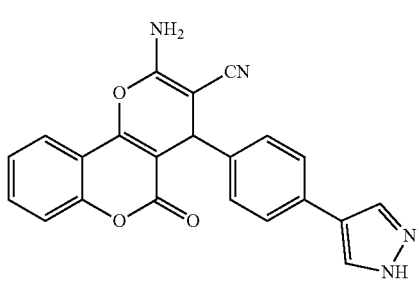

-continued
130
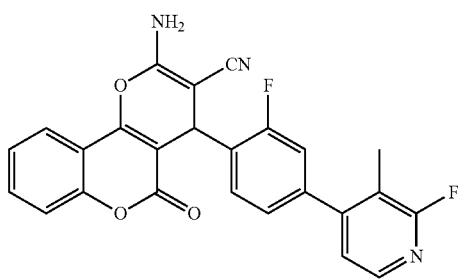
131
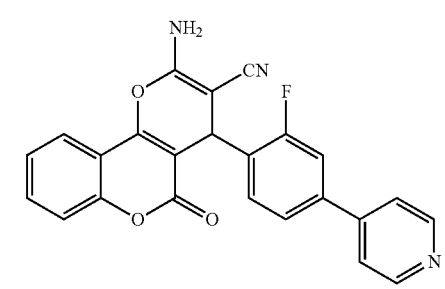
132
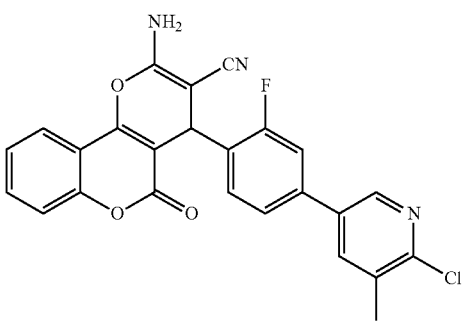
133
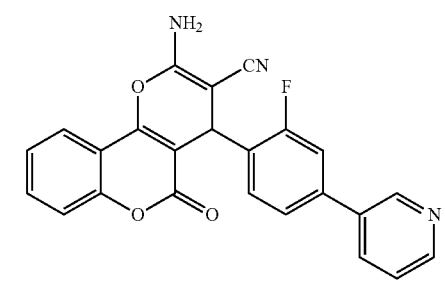
134
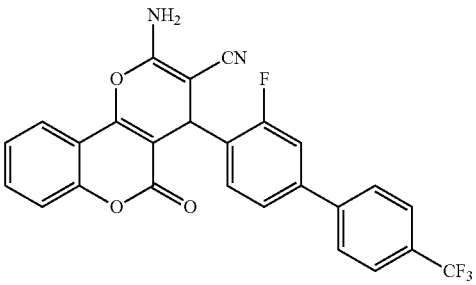
-continued
135
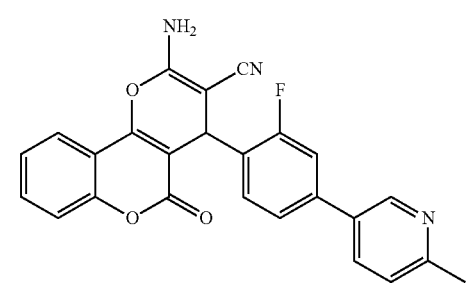
136
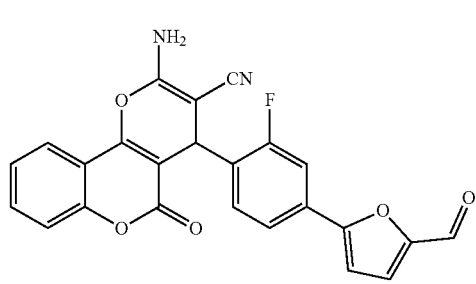
137
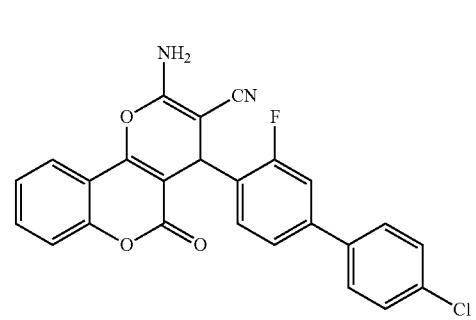
138
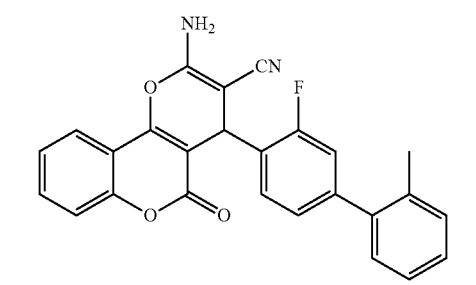
139
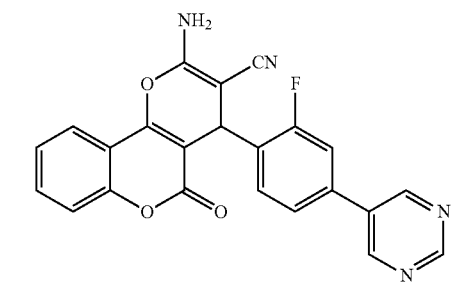

140
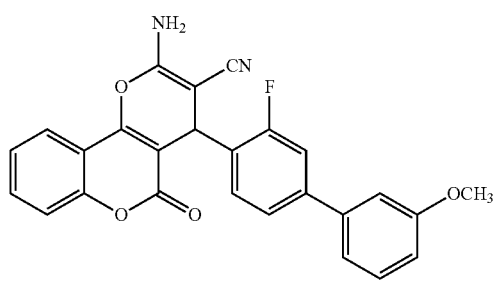
141
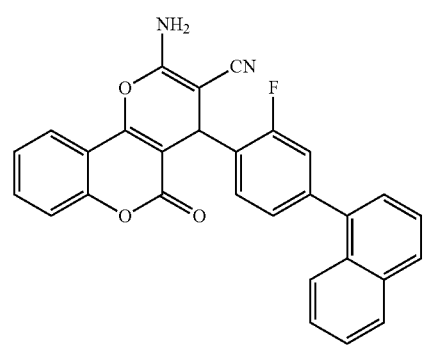
142
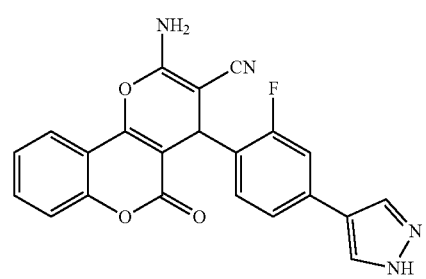
143
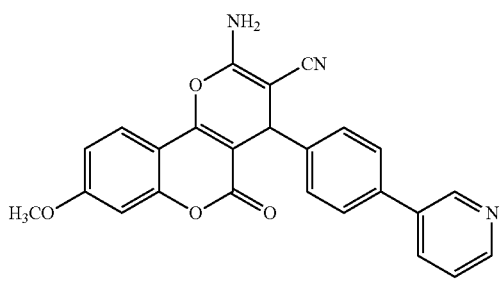
144
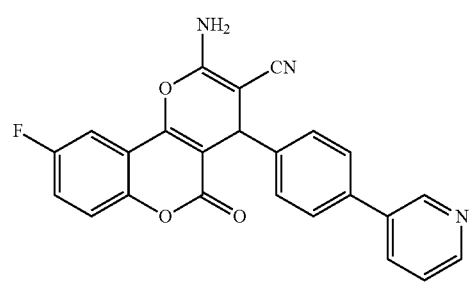
145
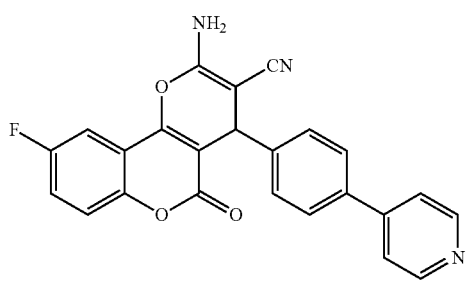
146
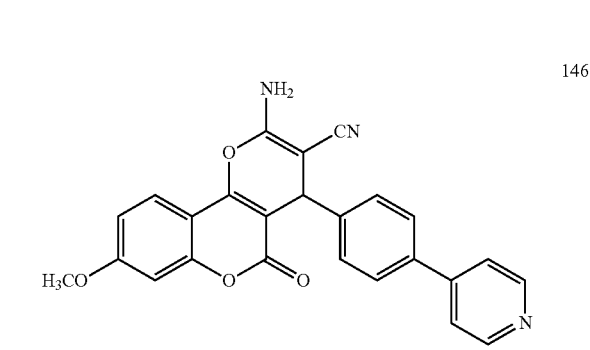
147
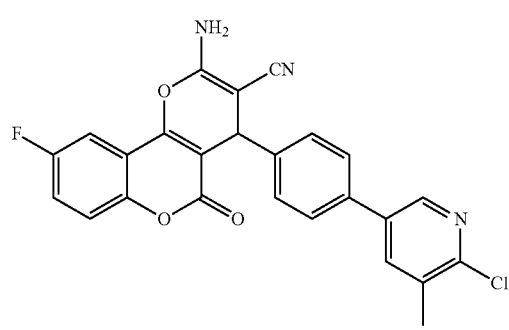
148
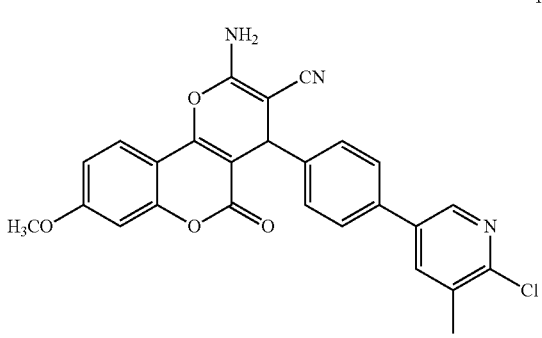
149
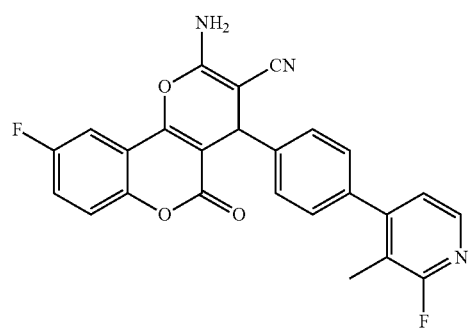

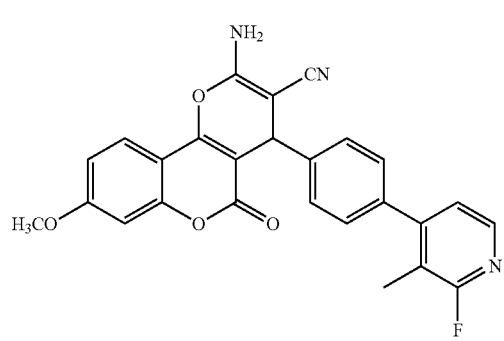
150
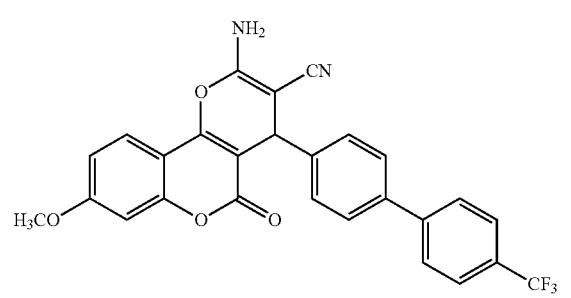
151
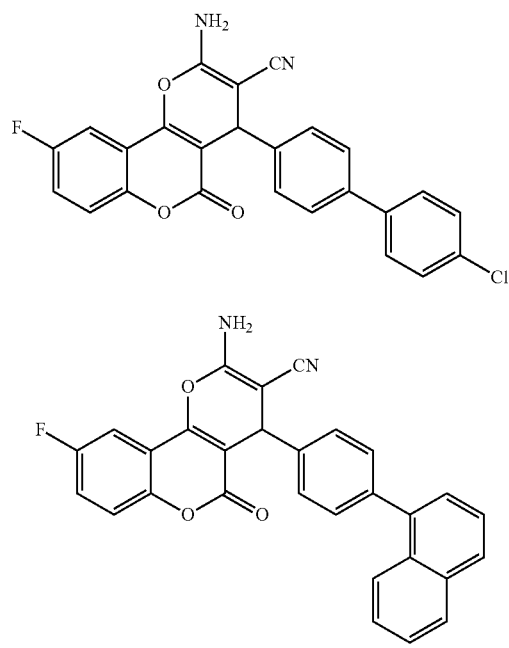
152
153
154
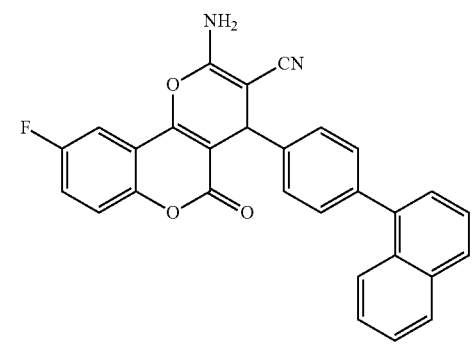
155
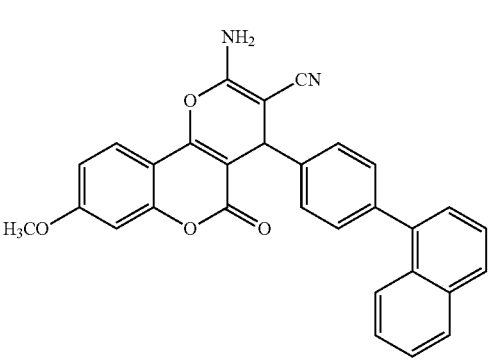
156
157
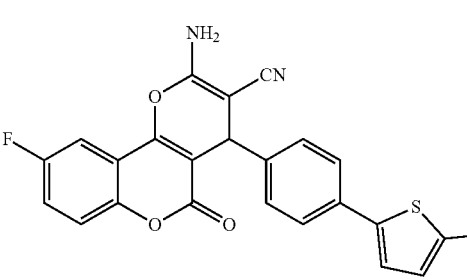
158
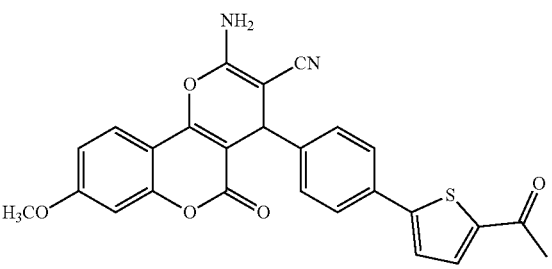
159

-continued
160
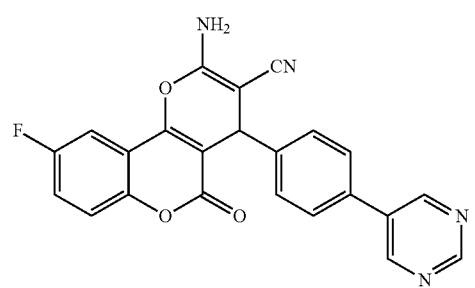
161
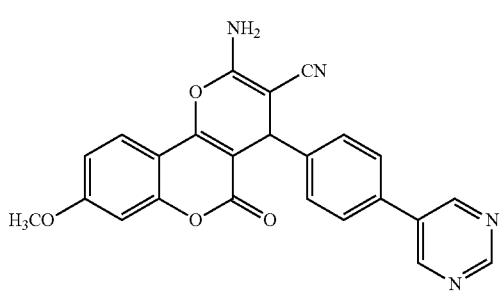
162
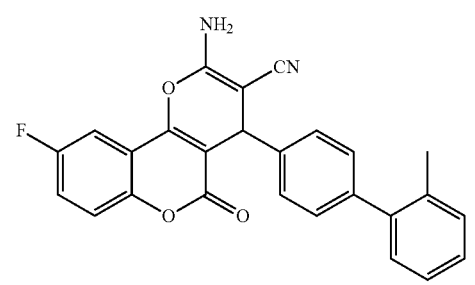
163
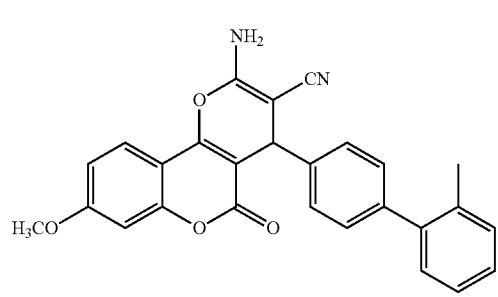
164
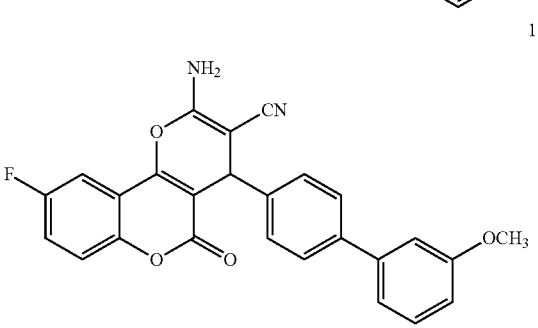
-continued
165
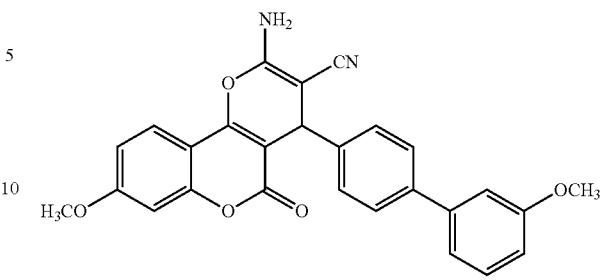
166
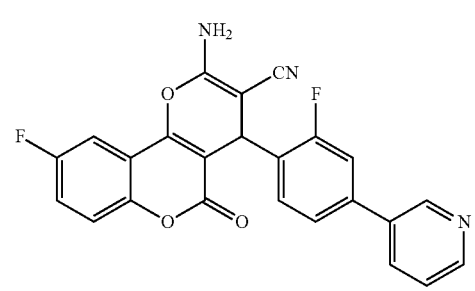
167
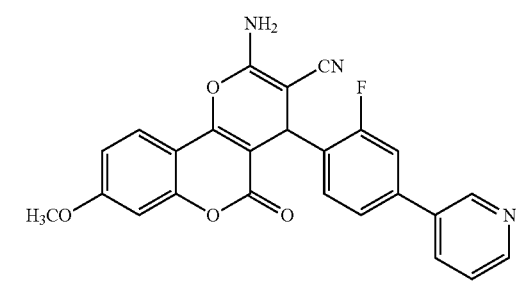
168
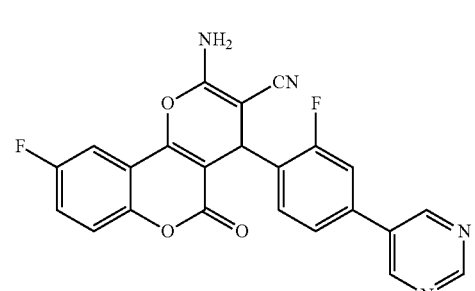
169
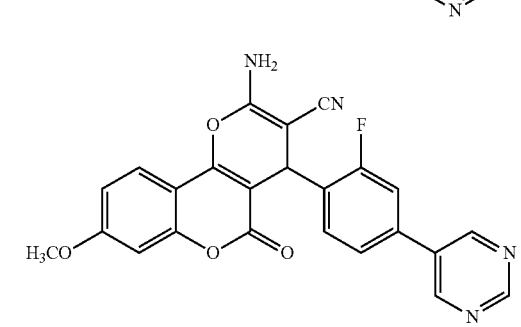

170
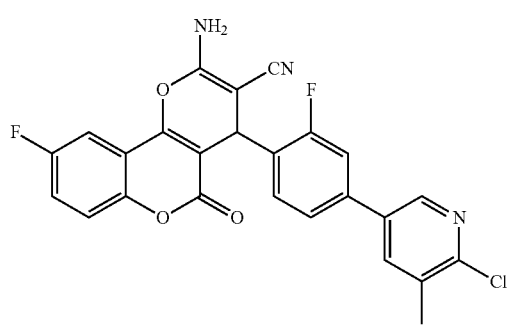
171
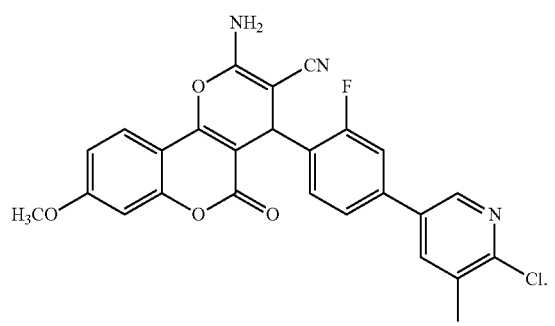
10. The compound according claim 9, wherein the compound is selected from:
1
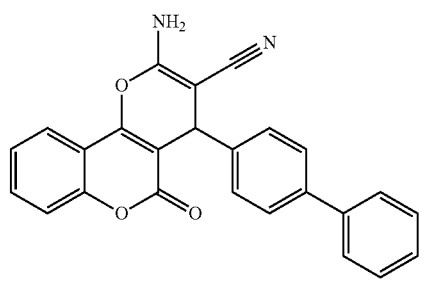
13
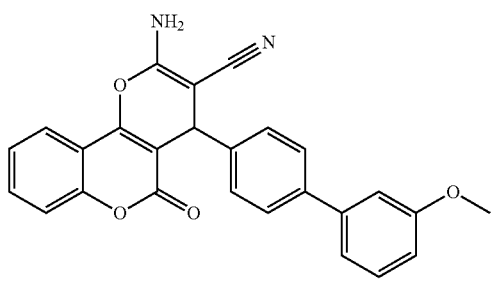
25
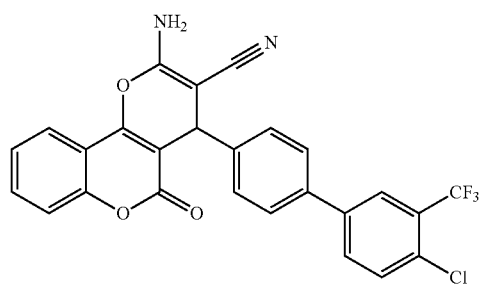
43
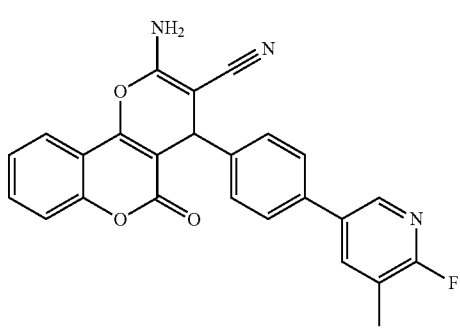
49
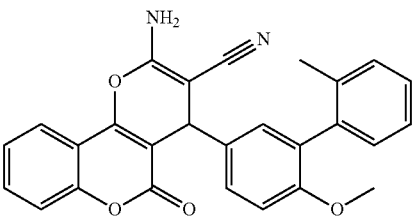
55
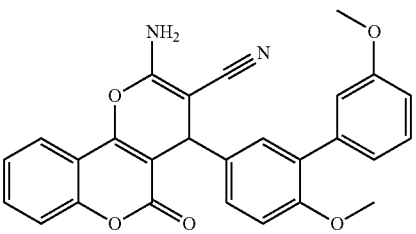
61
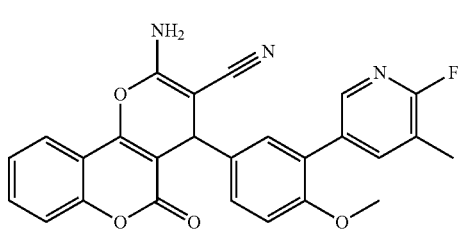
73
91

-continued
98
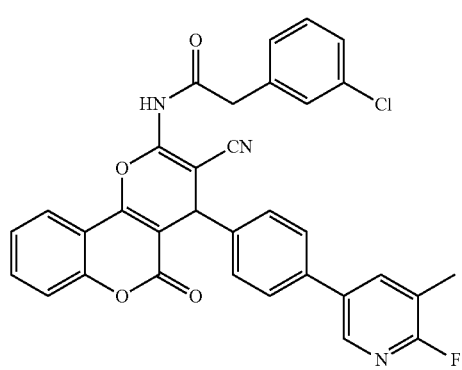
99
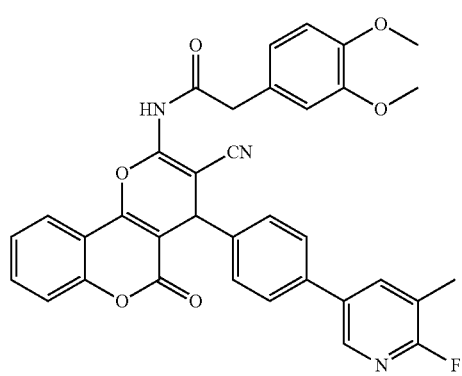
100
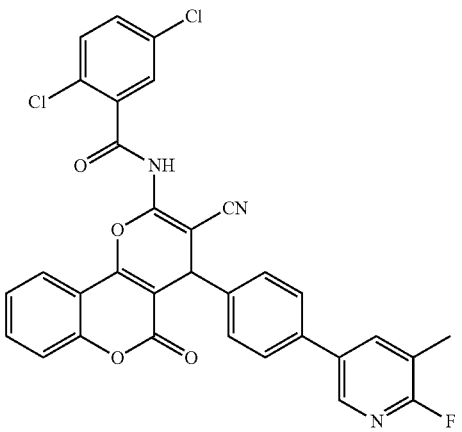
101
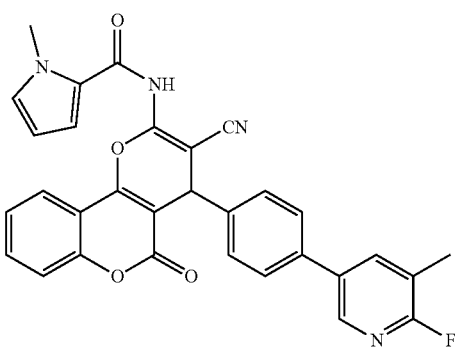
-continued
102
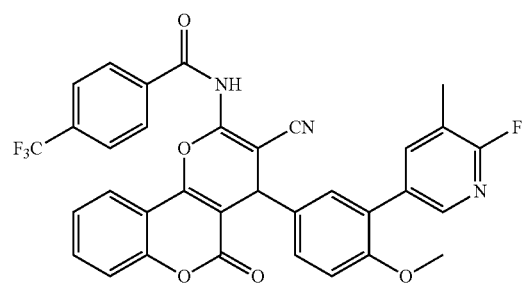
107
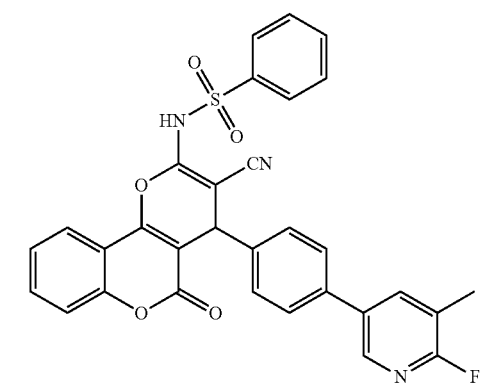
109
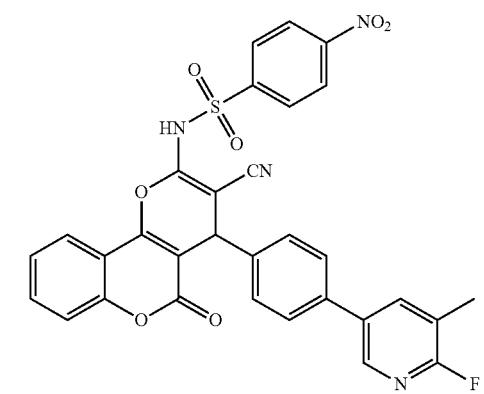
111
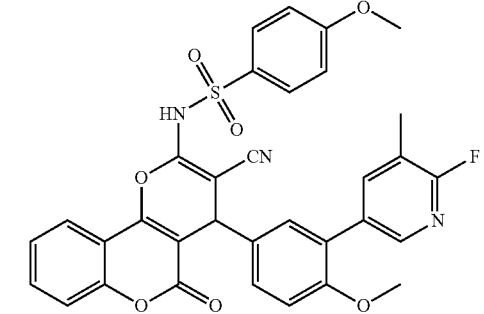

113
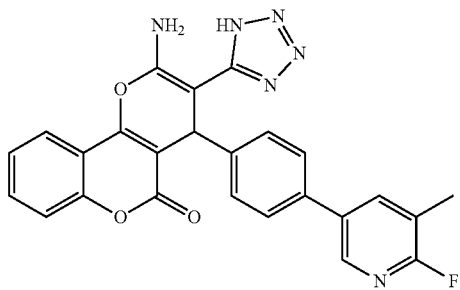
127
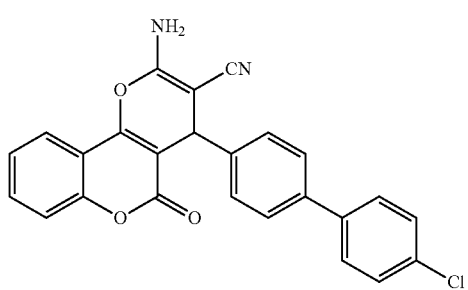
136
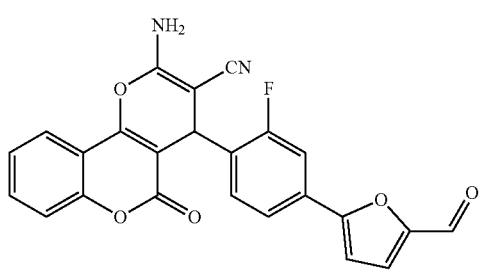
138
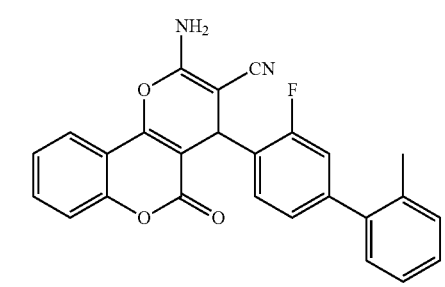
144
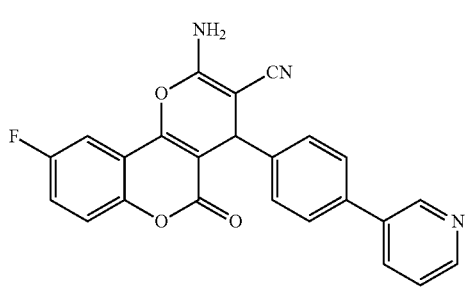
147
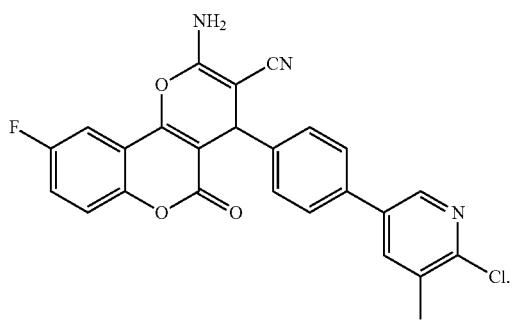
11. The compound according claim 10, wherein the compound is selected from:
1
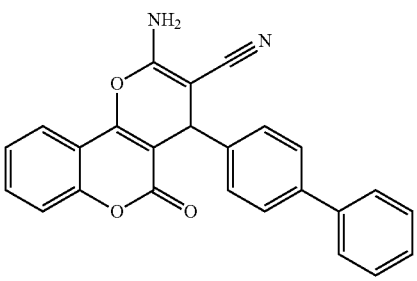
13
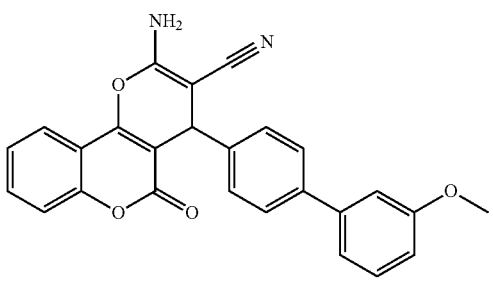
25
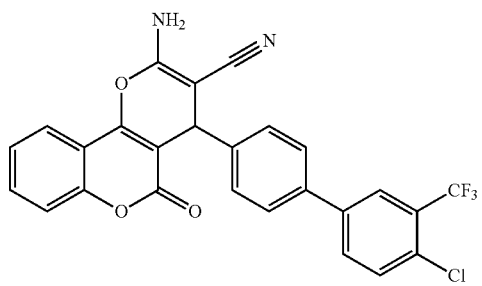
43
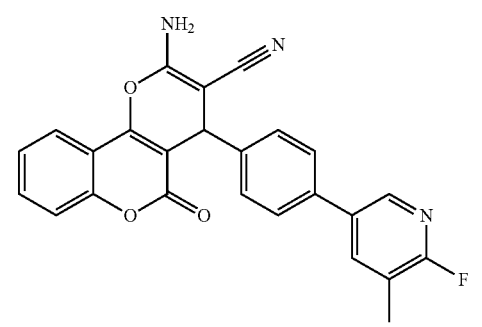

49
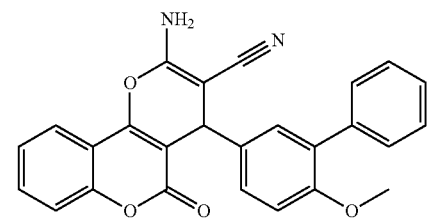
55
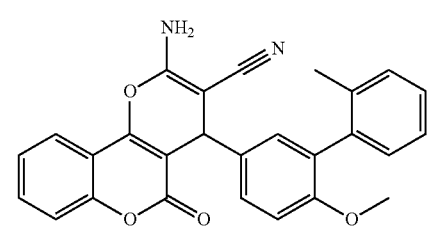
61
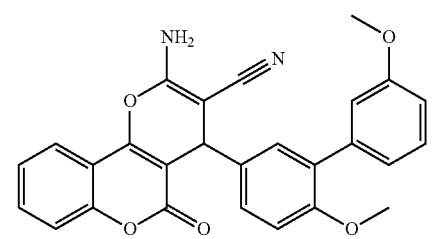
73
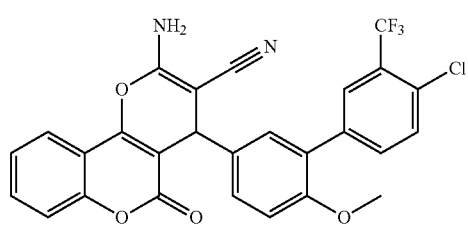
91
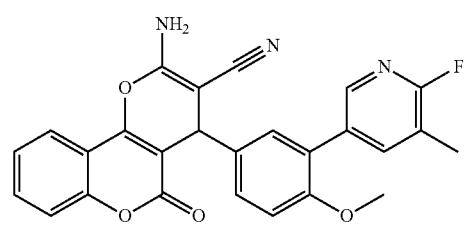
107
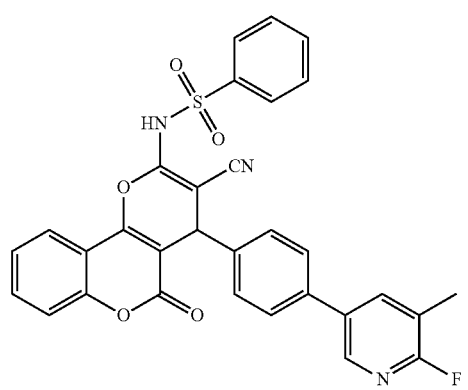
127
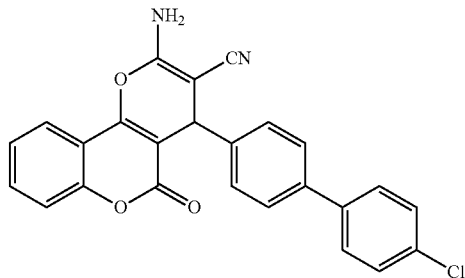
136
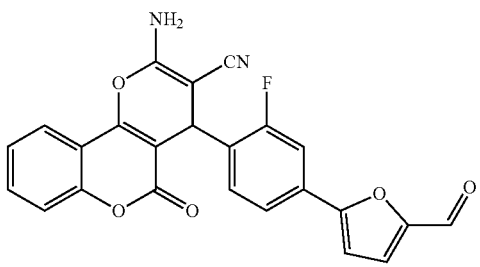
138
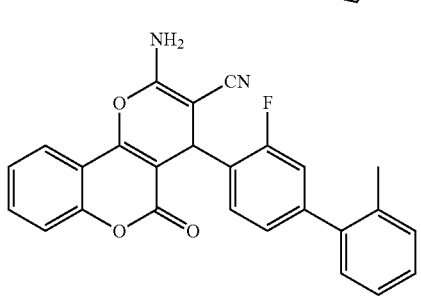
144
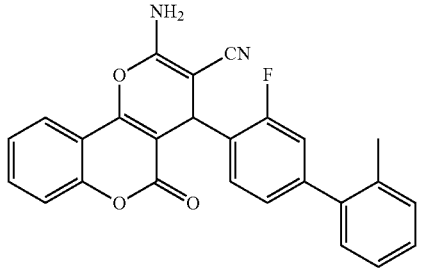
147
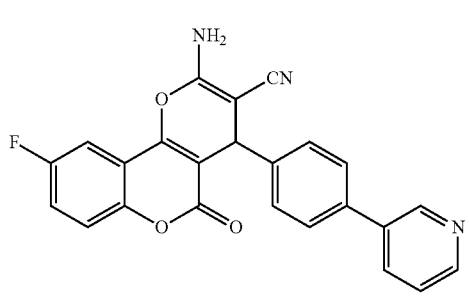
12. A pharmaceutical formulation including a compound of formula I, as defined in claim 1, and another therapeutic agent, in admixture with a pharmaceutically-acceptable adjuvant, diluent or carrier.
13. A compound of formula I as defined in claim 1, or a pharmaceutically acceptable salt or solvate thereof, for use in medicine.

14. A method of treatment of a cancer, which method comprises the administration of an effective amount of a compound of formula I as defined in claim 1, or a pharmaceutically acceptable salt or solvate thereof, to a patient in need of such treatment.

15. A method of treatment of a cancer, which method comprises the administration of an effective amount of a compound of formula I, as defined in claim 1, and another therapeutic agent to a patient in need of such treatment.

16. A combination product comprising
    (A) a compound of formula I, as defined in claim 1, and
    (B) another therapeutic agent,
    wherein each of components (A) and (B) is formulated in admixture with a pharmaceutically-acceptable adjuvant, diluent or carrier.

17. A method of treatment of a cancer, which method comprises the administration of an effective amount of a combination product as defined in claim 16.

18. A pharmaceutical formulation including a compound of formula I, as defined in claim 1, and another therapeutic agent, in admixture with a pharmaceutically-acceptable adjuvant, diluent or carrier.

19. A kit of parts comprising components:
    (i) a pharmaceutical formulation including a compound of formula I, as defined in claim 1, in admixture with a pharmaceutically-acceptable adjuvant, diluent or carrier; and
    (ii) a pharmaceutical formulation including another therapeutic agent, in admixture with a pharmaceutically-acceptable adjuvant, diluent or carrier, which components (i) and (ii) are each provided in a form that is suitable for administration in conjunction with the other.

\* \* \* \* \*